US010370380B2

(12) United States Patent
Zhang et al.

(10) Patent No.: US 10,370,380 B2
(45) Date of Patent: Aug. 6, 2019

(54) OCTAHYDROPYRROLO[3,4-C]PYRROLE DERIVATIVES AND USES THEREOF

(71) Applicant: Sunshine Lake Pharma Co., Ltd., Dongguan, Guangdong (CN)

(72) Inventors: Yingjun Zhang, Dongguan (CN); Chuanfei Jin, Dongguan (CN); Ji Zhang, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/777,219

(22) PCT Filed: Nov. 23, 2016

(86) PCT No.: PCT/CN2016/106937
§ 371 (c)(1),
(2) Date: May 18, 2018

(87) PCT Pub. No.: WO2017/088759
PCT Pub. Date: Jun. 1, 2017

(65) Prior Publication Data
US 2018/0334460 A1    Nov. 22, 2018

(30) Foreign Application Priority Data

Nov. 23, 2015    (CN) .......................... 2015 1 0823712

(51) Int. Cl.
| | |
|---|---|
| C07D 487/04 | (2006.01) |
| A61K 31/423 | (2006.01) |
| A61K 31/428 | (2006.01) |
| A61K 31/4709 | (2006.01) |
| A61K 31/517 | (2006.01) |
| A61K 45/06 | (2006.01) |

(52) U.S. Cl.
CPC .......... *C07D 487/04* (2013.01); *A61K 31/423* (2013.01); *A61K 31/428* (2013.01); *A61K 31/4709* (2013.01); *A61K 31/517* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,470,710 B2 | 12/2008 | Branch | |
| 7,897,627 B2 | 3/2011 | Knust et al. | |
| 7,951,797 B2 | 5/2011 | Breslin et al. | |
| 8,093,255 B2 | 1/2012 | Alvaro | |
| 8,263,586 B2 | 9/2012 | Cox | |
| 8,362,009 B2 | 1/2013 | Bergman et al. | |
| 8,592,457 B2 | 11/2013 | Bergman | |
| 8,618,102 B2 | 12/2013 | Coleman | |
| 8,653,263 B2 | 2/2014 | Chai | |
| 8,680,275 B2 | 3/2014 | Branstetter | |
| 8,685,961 B2 | 4/2014 | Brashear | |
| 8,710,076 B2 | 4/2014 | Breslin | |
| 8,940,898 B2 | 1/2015 | Kuduk et al. | |
| 8,969,352 B2 | 3/2015 | Gelin et al. | |
| 9,062,044 B2 | 6/2015 | Branstetter | |
| 9,108,959 B2 | 8/2015 | Baxter | |
| 9,115,117 B2 | 8/2015 | Dvorak et al. | |
| 9,150,566 B2 | 10/2015 | Bolli et al. | |
| 9,156,819 B2 | 10/2015 | Kuduk | |
| 9,493,446 B2 | 11/2016 | Bolli et al. | |
| 9,546,152 B2 | 1/2017 | Kuduk | |
| 9,550,786 B2 | 1/2017 | Cooke | |
| 9,556,145 B2 | 1/2017 | Kuduk | |
| 9,556,190 B2 | 1/2017 | Kuduk et al. | |
| 9,586,934 B2 | 3/2017 | Kuduk | |
| 9,586,950 B2 | 3/2017 | Kuduk | |
| 9,586,962 B2 | 3/2017 | Letavic | |
| 9,617,246 B2 | 4/2017 | Kuduk et al. | |
| 9,624,197 B2 | 4/2017 | Kuduk | |
| 9,643,955 B2 | 5/2017 | Kuduk | |
| 9,676,751 B2 | 6/2017 | Kuduk | |
| 9,695,163 B2 | 7/2017 | Liverton et al. | |
| 9,725,434 B2 | 8/2017 | Kuduk et al. | |
| 9,732,075 B2 | 8/2017 | Boss et al. | |
| 9,732,077 B2 | 8/2017 | Kuduk | |
| 9,745,284 B2 | 8/2017 | Kuduk | |
| 9,765,057 B2 | 9/2017 | Kuduk | |
| 9,790,220 B2 | 10/2017 | Fieldhouse et al. | |
| 9,828,368 B2 | 11/2017 | Liverton et al. | |
| 9,914,721 B2 | 3/2018 | Boss et al. | |
| 2009/0022670 A1 | 1/2009 | Alvaro | |
| 2009/0105318 A1 | 4/2009 | Coleman | |
| 2009/0192143 A1 | 7/2009 | Cox | |
| 2010/0210667 A1 | 8/2010 | Alvaro | |
| 2010/0267730 A1 | 10/2010 | Alvaro | |
| 2011/0039857 A1 | 2/2011 | Aissaoui | |
| 2011/0257198 A1 | 10/2011 | Alvaro | |
| 2012/0208812 A1* | 8/2012 | Chai | .................... C07D 487/04 514/234.5 |
| 2014/0228377 A1 | 8/2014 | Abe | |
| 2016/0068514 A1 | 3/2016 | Kuduk | |
| 2016/0102073 A1 | 4/2016 | Kuduk | |
| 2016/0304490 A1 | 10/2016 | Kuduk et al. | |
| 2017/0233385 A1 | 8/2017 | He et al. | |

FOREIGN PATENT DOCUMENTS

| | | |
|---|---|---|
| CN | 104548097 A | 4/2015 |
| JP | 2014141480 A | 8/2014 |

(Continued)

OTHER PUBLICATIONS

Bibia Heidmann et al., Discovery of Highly Potent Dual Orexin Receptor Antagonists via a Scaffold-Hopping Approach, ChemMedChem, 2016, 11(19): 2132-2146.

(Continued)

*Primary Examiner* — Alicia L Otton
(74) *Attorney, Agent, or Firm* — Kam Wah Law

(57) ABSTRACT

The invention relates to octahydropyrrolo [3, 4-c] pyrrole derivatives and uses thereof. Compounds and pharmaceutical compositions comprising the compounds provided herein are used for antagonizing orexin receptors. The invention also relates to processes for preparing the compounds and pharmaceutical compositions, and uses thereof in treating or preventing a disease related to orexin receptors.

7 Claims, No Drawings

(56) References Cited

FOREIGN PATENT DOCUMENTS

| WO | 2009011775 A1 | | 1/2009 | |
|---|---|---|---|---|
| WO | 2010060470 A1 | | 6/2010 | |
| WO | 2010060471 A1 | | 6/2010 | |
| WO | 2010060472 A1 | | 6/2010 | |
| WO | WO 2011/050198 | * | 4/2011 | ........... C07D 487/04 |
| WO | 2012085852 A1 | | 6/2012 | |
| WO | 2012085857 A1 | | 6/2012 | |
| WO | 2013050938 A1 | | 4/2013 | |

OTHER PUBLICATIONS

International Search Report of PCT/CN2016/106937.
Written Opinion of PCT/CN2016/106937.

* cited by examiner

US 10,370,380 B2

OCTAHYDROPYRROLO[3,4-C]PYRROLE DERIVATIVES AND USES THEREOF

CROSS-REFERENCE TO RELATED APPLICATIONS

This is a U.S. national stage application of the International Patent Application No. PCT/CN2016/106937, filed 23 Nov. 2016, which claims priority to Chinese Patent Application No. 201510823712.8, filed 23 Nov. 2015, both of which are incorporated herein by reference in their entireties.

FIELD OF THE INVENTION

The present invention belongs to the field of pharmaceutical technology, and more specifically relates to octahydropyrrolo[3,4-c]pyrrole derivatives, compositions, pharmaceutical combinations and kits comprising the compounds, and using methods and uses thereof. More specifically, the compounds disclosed herein can be used as orexin receptor antagonists for treating, preventing or lessening a disease related to orexin receptors, and the pharmaceutical compositions, pharmaceutical combinations or kits disclosed herein have functions of prevention, treatment or lessening of a disease related to orexin receptors.

BACKGROUND OF THE INVENTION

Orexin, also known as hypocretin, orexin peptide, comprises orexin A and orexin B (or hypocretin-1 and hypocretin-2), which is a neuropeptide secreted by the hypothalamus, its main physiological functions are: 1. regulation of feeding, orexin can significantly promote eating, which shows a dose-dependent response with the food intake, and activates neurons regulating feeding; 2. regulation of energy metabolism, orexin can significantly increase the metabolic rate; 3. regulation of sleep-wake, orexin can inhibit rapid eye movement sleep and extend wake time, and it can promote sleep that the effect of orexin are blocked; 4. regulation of endocrine, orexin have a very significant effect on the endocrine of pituitary hormones; 5. relationship with a sense of reward, learning and memory; 6. promotion of gastric acid secretion 7. promotion of an increase in drinking water 8. elevation of blood pressure; 9. playing an important role in reward system and drug addiction mechanism, and the like. (Piper, et al., The novel brain neuropeptide, orexin-A, modulates the sleep-wake cycle of rats. *Eur. J. Neuroscience*, 2000, 12(2), 726-730; and Sakurai, T., et al., The neural circuit of orexin (hypocretin): Maintaining sleep and wakefulness. *Nature Review Neuroscience*, 2007, 8: 171181).

Orexin produces physiological effects by acting on orexin receptor (OXR). Orexin receptor is a G-protein coupled receptor, which has two types, called $OX_1$ receptor and $OX_2$ receptor respectively, wherein, $OX_1$ receptor is selective for orexin A, and $OX_2$ is non-selective for orexin A and orexin B (Sakurai T. et al., Orexins and orexin receptors: a family of hypothalamic neuropeptides and G protein-coupled receptors that regulate feeding behavior. *Cell*, 1998, 92(4): 573-585). $OX_1$ receptors and $OX_2$ receptors almost only exist in brain tissue, and are selectively expressed in the brain, wherein $OX_1$ receptor is expressed at high density in locus coeruleus, which is a nuclei originis of noradrenergic neurons, and $OX_2$ receptor is expressed at high density in tuberomammillary nucleus, which is a nuclei originis of histaminergic neurons. Expression of both $OX_1$ receptor and $OX_2$ receptor can be found in raphe nuclei, which are nuclei originis of serotonergic neurons, and found in ventral tegmental area, which are nuclei originis of dopaminergic neurons. Moreover, $OX_2$ receptor also can be found in brain stem cholinergic neurons, which are responsible for regulating rapid eye movement sleep, and have an impact on their nuclear activities. (Marcus, J. N. et al., Differential expression of orexin receptors 1 and 2 in the rat brain. *J. Comp. Neurol.*, 2001, 43 5(1): 6-25; and Trivedi, P. et al., Distribution of orexin receptor mRNA in the rat brain. *FEBS Lett.*, 1998, 438(1-2): 71-75).

Thus, orexin receptors have an important significance in pathology, and associated with a variety of diseases, such as a sleep disorder, depression, anxiety, a panic disorder, an obsessive-compulsive disorder, an affective disorder, depressive neurosis, anxiety neurosis, a mood disorder, a panic attack disorder, a behavior disorder, emotional disturbance, a post-traumatic stress disorder, sexual dysfunction, psychosis, schizophrenia, manic depression, a mental disorder, dementia, drug dependence, addiction, a cognitive disorder, Alzheimer's disease, Parkinson's disease, a movement disorder, an eating disorder, headache, migraine, pain, a digestive system disease, epilepsy, inflammation, a cardiovascular disease, diabetes, a metabolic disease, an immunity-related disease, an endocrine-related disease and high blood pressure, and so on.

SUMMARY OF THE INVENTION

This application is based on the discovery of the following questions and facts:

The drug related to orexin receptors in the current market is only the hypnotics of Suvorexant developed by Merck & Co., Inc. in America, which is an orexin receptor antagonist, but the drug had been rejected because of security problems. In view of the above, provided herein is a new compound having orexin receptor antagonistic activity, and the compound has a better pharmacological activity, a lower toxic and side effect and a higher security than the existing similar compounds. Meanwhile the compound also has superior physicochemical properties, pharmacokinetic properties and toxicological characteristics. Hence, it holds the promise of clinical application.

The following just summarizes some aspects of the invention, but are not limited to these. These aspects and other parts will be described more completely later. All references of this specification are incorporated herein by reference in their entirety. Where there are differences between disclosure of the present specification and cited references, the disclosure of the present specification controls.

Provided herein is a compound having an orexin receptor antagonistic activity, specifically the present invention relates to octahydropyrrolo[3,4-c]pyrrole derivatives and pharmaceutical composition thereof, the compound, pharmaceutical composition, pharmaceutical combination and kit can be used for preventing or treating a disease related to orexin receptors.

The compounds provided herein exhibit a superior antagonistic activity, having a good pharmacological efficacy, pharmacokinetic properties and/or low toxicological characteristics, such as a superior brain/plasma ratio, greater bioavailability, good metabolic stability, a lower toxic and side effect, a higher security, and so on. Meanwhile, the excellent properties of certain parameters of the present compounds, such as half-life, clearance rate, selectivity, bioavailability, chemical stability, metabolic stability, permeability of the membrane, solubility, etc., can prompt the decrease of side effects and the expand of therapeutic index or the improvement of tolerability.

Specifically, in one aspect, the present invention relates to a compound having Formula (I) or a stereoisomer, a tautomer, an N-oxide, a solvate, a metabolite, a pharmaceutically acceptable salt or a prodrug thereof,

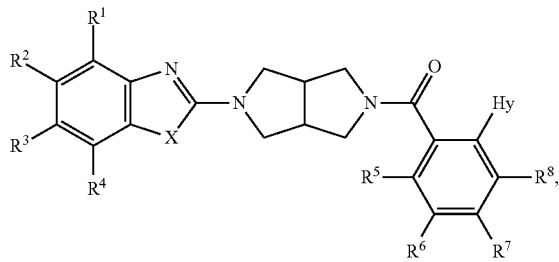

wherein X is —O—, —S—, —NH—, *—CR$^9$═N— or *—CR$^9$═CR$^{9a}$—, wherein * refers to an end attached to the benzene ring;

Hy is triazolyl, and wherein the triazolyl is optionally substituted by one or more substituents independently selected from halogen, oxo (═O), C$_{1-6}$ alkyl, C$_{1-6}$ haloalkyl, C$_{1-6}$ alkoxy and benzyl;

each R$^1$, R$^2$, R$^3$, R$^4$, R$^9$ and R$^{9a}$ is independently H, D, —CD$_3$, —CN, —NH$_2$, —OH, —NO$_2$, —COOH, —C(═O)NH$_2$, halogen, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, C$_{1-6}$ alkylamino, C$_{1-6}$ hydroxy-substituted alkyl, (C$_{1-6}$ alkyl)-C(═O)—, (C$_{1-6}$ alkoxy)-C(═O)—, (C$_{1-6}$ alkylamino)-C(═O)—, cycloalkyl, heterocyclyl, aryl or heteroaryl;

each of R$^5$ and R$^6$ is independently H, D, F, Cl, Br, I, —CN, —NH$_2$, —OH, —NO$_2$, —COOH, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, C$_{1-6}$ alkylamino, C$_{1-6}$ hydroxy-substituted alkyl, (C$_{1-6}$ alkyl)-C(═O)—, (C$_{1-6}$ alkoxy)-C(═O)—, (C$_{1-6}$ alkylamino)-C(═O)—, cycloalkyl, heterocyclyl, aryl or heteroaryl;

R$^7$ is H, D, F, Cl, Br, I, —CN, —NH$_2$, —OH, —NO$_2$, —COOH, C$_{1-6}$ alkyl, C$_{2-6}$ alkenyl, C$_{2-6}$ alkynyl, C$_{1-6}$ haloalkyl, C$_{2-6}$ alkoxy, C$_{1-6}$ haloalkoxy, C$_{1-6}$ alkylamino, C$_{1-6}$ hydroxy-substituted alkyl, (C$_{1-6}$ alkyl)-C(═O)—, (C$_{1-6}$ alkoxy)-C(═O)—, (C$_{1-6}$ alkylamino)-C(═O)—, cycloalkyl, heterocyclyl, aryl or heteroaryl; and R$^8$ is H, D, Cl, Br, I, —CN, —NH$_2$, —OH, —NO$_2$, —COOH, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, C$_{1-6}$ alkylamino, C$_{1-6}$ hydroxy-substituted alkyl, (C$_{1-6}$ alkyl)-C(═O)—, (C$_{1-6}$ alkoxy)-C(═O)—, (C$_{1-6}$ alkylamino)-C(═O)—, cycloalkyl, heterocyclyl, aryl or heteroaryl;

when X is —O—, at least one of R$^1$, R$^2$, R$^3$, R$^4$, R$^5$, R$^6$, R$^7$ and R$^8$ is not H.

In one embodiment, provided herein is a compound having Formula (II) or a stereoisomer, a tautomer, an N-oxide, a solvate, a metabolite, a pharmaceutically acceptable salt or a prodrug thereof,

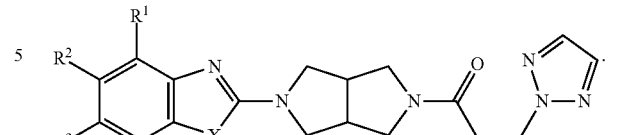

In one embodiment, provided herein is a compound having Formula (III) or a stereoisomer, a tautomer, an N-oxide, a solvate, a metabolite, a pharmaceutically acceptable salt or a prodrug thereof,

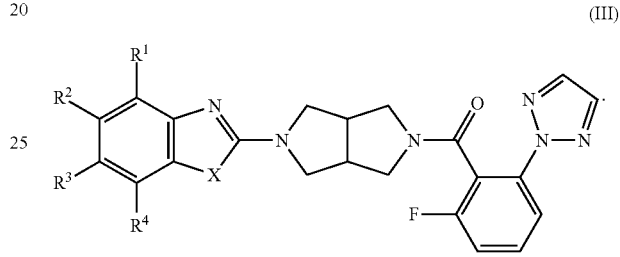

In one embodiment, provided herein is a compound having Formula (IV) or a stereoisomer, a tautomer, an N-oxide, a solvate, a metabolite, a pharmaceutically acceptable salt or a prodrug thereof,

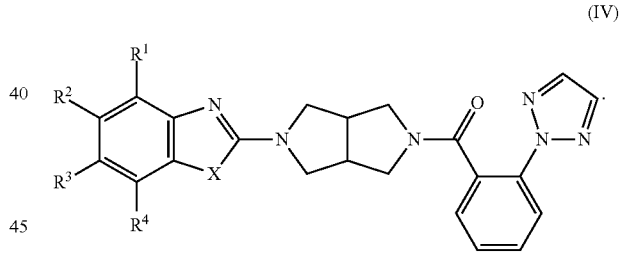

In one embodiment, each R$^1$, R$^2$, R$^3$, R$^4$, R$^9$ and R$^{9a}$ of Formula (I), (II), (III) or (IV) is independently H, D, —CD$_3$, —CN, —NH$_2$, —OH, —NO$_2$, —COOH, —C(═O)NH$_2$, halogen, C$_{1-4}$ alkyl, C$_{2-4}$ alkenyl, C$_{2-4}$ alkynyl, C$_{1-4}$ haloalkyl, C$_{1-4}$ alkoxy, C$_{1-4}$ haloalkoxy, C$_{1-4}$ alkylamino, C$_{1-4}$ hydroxy-substituted alkyl, (C$_{1-4}$ alkyl)-C(═O)—, (C$_{1-4}$ alkoxy)-C(═O)— or (C$_{1-4}$ alkylamino)-C(═O)—.

In one embodiment, each R$^5$ and R$^6$ of Formula (I) is independently H, D, F, Cl, Br, I, —CN, —NH$_2$, —OH, —NO$_2$, —COOH, C$_{1-4}$ alkyl, C$_{2-4}$ alkenyl, C$_{2-4}$ alkynyl, C$_{1-4}$ haloalkyl, C$_{1-4}$ alkoxy, C$_{1-4}$ haloalkoxy, C$_{1-4}$ alkylamino, C$_{1-4}$ hydroxy-substituted alkyl, (C$_{1-4}$ alkyl)-C(═O)—, (C$_{1-4}$ alkoxy)-C(═O)—, (C$_{1-4}$ alkylamino)-C(═O)—;

R$^7$ is H, D, F, Cl, Br, I, —CN, —NH$_2$, —OH, —NO$_2$, —COOH, C$_{1-4}$ alkyl, C$_{2-4}$ alkenyl, C$_{2-4}$ alkynyl, C$_{1-4}$ haloalkyl, C$_{2-4}$ alkoxy, C$_{1-4}$ haloalkoxy, C$_{1-4}$ alkylamino, C$_{1-4}$ hydroxy-substituted alkyl, (C$_{1-4}$ alkyl)-C(═O)—, (C$_{1-4}$ alkoxy)-C(═O)—, (C$_{1-4}$ alkylamino)-C(═O)—; and $R^8$ is H, D, Cl, Br, I, —CN, —NH$_2$, —OH, —NO$_2$, —COOH, C$_{1-4}$ alkyl, C$_{2-4}$ alkenyl, C$_{2-4}$ alkynyl, C$_{1-4}$ haloalkyl, C$_{1-4}$ alkoxy, C$_{1-4}$ haloalkoxy, C$_{1-4}$ alkylamino, C$_{1-4}$ hydroxy-substituted alkyl, (C$_{1-4}$ alkyl)-C(=O)—, (C$_{1-4}$ alkoxy)-C(=O)—, (C$_{1-4}$ alkylamino)-C(=O)—.

In one embodiment, each $R^1$, $R^2$, $R^3$, $R^4$, $R^9$ and $R^{9a}$ of Formula (I), (II), (III) or (IV) is independently H, D, —CD$_3$, —CN, —NH$_2$, —OH, —NO$_2$, —COOH, —C(=O)NH$_2$, F, Cl, Br, I, methyl, ethyl, n-propyl, isopropyl, —CF$_3$, —CH$_2$CF$_3$, —CF$_2$CF$_3$, methoxy, ethoxy, n-propyloxy, isopropyloxy, —NHCH$_3$, —N(CH$_3$)$_2$ or —CH$_2$OH.

In one embodiment, each of $R^5$ and $R^6$ of Formula (I) is independently H, D, F, Cl, Br, I, —CN, —NH$_2$, —OH, —NO$_2$, —COOH, methyl, ethyl, n-propyl, isopropyl, —CF$_3$, —CH$_2$CF$_3$, —CF$_2$CF$_3$, methoxy, ethoxy, n-propyloxy, isopropyloxy, —NHCH$_3$, —N(CH$_3$)$_2$ or —CH$_2$OH;

$R^7$ is H, D, F, Cl, Br, I, —CN, —NH$_2$, —OH, —NO$_2$, —COOH, methyl, ethyl, n-propyl, isopropyl, —CF$_3$, —CH$_2$CF$_3$, —CF$_2$CF$_3$, ethoxy, n-propyloxy, isopropyloxy, —NHCH$_3$, —N(CH$_3$)$_2$ or —CH$_2$OH; and $R^8$ is H, D, Cl, Br, I, —CN, —NH$_2$, —OH, —NO$_2$, —COOH, methyl, ethyl, n-propyl, isopropyl, —CF$_3$, —CH$_2$CF$_3$, —CF$_2$CF$_3$, methoxy, ethoxy, n-propyloxy, isopropyloxy, —NHCH$_3$, —N(CH$_3$)$_2$ or —CH$_2$OH.

In another aspect, provided herein is a pharmaceutical composition comprising the compound of the present invention.

In one embodiment, the pharmaceutical composition further comprising a pharmaceutically acceptable carrier, excipient, adjuvant or a combination thereof.

In one embodiment, wherein the pharmaceutical composition is tablet, injection, powder, capsule, elixir, suspension, syrup, pill or sheet.

In another aspect, provided herein is use of the compound or the pharmaceutical composition disclosed herein for preventing, treating or lessening a disease related to orexin receptors.

In one embodiment, the disease related to orexin receptors is a sleep disorder, depression, anxiety, a panic disorder, an obsessive-compulsive disorder, an affective disorder, depressive neurosis, anxiety neurosis, a mood disorder, a panic attack disorder, a behavior disorder, emotional disturbance, a post-traumatic stress disorder, sexual dysfunction, psychosis, schizophrenia, manic depression, mental disorders, dementia, drug dependence, addiction, cognitive disorders, Alzheimer's disease, Parkinson's disease, a movement disorder, an eating disorder, headache, migraine, pain, a digestive system disease, epilepsy, inflammation, a cardiovascular disease, diabetes, a metabolic disease, an immunity-related disease, an endocrine-related disease or high blood pressure.

In another aspect, provided herein is use of the compound or the pharmaceutical composition disclosed herein in the manufacture of a medicament for antagonizing orexin receptors.

In another aspect, provided herein is the compound or the pharmaceutical composition disclosed herein for use in preventing, treating or lessening a disease related to orexin receptors.

In some embodiments, wherein the disease related to orexin receptors is a sleep disorder, depression, anxiety, a panic disorder, an obsessive-compulsive disorder, an affective disorder, depressive neurosis, anxiety neurosis, a mood disorder, a panic attack disorder, a behavior disorder, emotional disturbance, a post-traumatic stress disorder, sexual dysfunction, psychosis, schizophrenia, manic depression, mental disorders, dementia, drug dependence, addiction, a cognitive disorder, Alzheimer's disease, Parkinson's disease, a movement disorder, an eating disorder, headache, migraine, pain, a digestive system disease, epilepsy, inflammation, a cardiovascular disease, diabetes, a metabolic disease, an immunity-related disease, an endocrine-related disease or high blood pressure.

In another aspect, provided herein is a method for preventing, treating or lessening a disease related to orexin receptors in a patient comprising administering to the patient therapeutically effective amount of the compound or the pharmaceutical composition disclosed herein.

In some embodiments, wherein the disease related to orexin receptors is a sleep disorder, depression, anxiety, a panic disorder, an obsessive-compulsive disorder, an affective disorder, depressive neurosis, anxiety neurosis, a mood disorder, a panic attack disorder, a behavior disorder, emotional disturbance, a post-traumatic stress disorder, sexual dysfunction, psychosis, schizophrenia, manic depression, mental disorders, dementia, drug dependence, addiction, a cognitive disorder, Alzheimer's disease, Parkinson's disease, a movement disorder, an eating disorder, headache, migraine, pain, a digestive system disease, epilepsy, inflammation, a cardiovascular disease, diabetes, a metabolic disease, an immunity-related disease, an endocrine-related disease or high blood pressure.

In another aspect, provided herein is use of the compound or the pharmaceutical composition disclosed herein. In the manufacture of a medicament for antagonizing one or more orexin receptors.

In another aspect, provided herein is pharmaceutical combination, wherein the pharmaceutical combination for use in preventing, treating or lessening a disease related to one or more orexin receptors, the compound disclosed herein as a first active agent; a medicament different from the compound disclosed herein as the second active agent, wherein the medicament different from the compound disclosed herein for use in preventing, treating or lessening a disease related to one or more orexin receptors.

In some embodiments, wherein the medicament different from the compound disclosed herein is adinazolan, allobarbital, alonimid, alprazolam, amitriptyline, amobarbital, amoxapine, bentazepam, tacitin, brotizolam, bupropion, buspirone, butabarbital, butalbital, capuride, carbocloral, chloral betaine, chloral hydrate, chlorodyne, clomipramine, clonazepam, domperidone, methaminodiazepoxide, cloretate, clozapine, cyprazepam, desipramine, dexclamo, diazepam, chloralsalicylamide, divalproic acid, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, orazepam, lormetazepam, maprotiline, mecloqualone, melatonin, methylphenobarbital, meprobamate, methaqualone, midaflur, midazolam, nefazodone, nisobamate, nitrazepam, nortriptyline, oxezepam, paraaldehyde, paroxetine, pentobarbital, perlapine, perphenazine, phenelzine, phenobarbital, Prazepam, promethazine, isopropylphenol, protriptyline, quazepam, reclazepam, rolipram, secobarbital, sertraline, suproclone, temazepam, thioridazine, tracazolate, tranylcypromine, trazodone, triazole benzodiazepine, trepipam, tricetamide, trichloroethyl phosphate, trifluoperazine, trimetozine, trimeprimine, uldazepam, venlafaxine, zaleplon, zolazepam, zolpidem and the salts and compositions thereof, and the like.

In another aspect, provided herein is a kit, wherein the kit is for use in preventing, treating or lessening a disease related to one or more orexin receptors, comprising a first container, wherein the first container is provided with the compound disclosed herein.

In some embodiments, wherein the kit further comprises a second container, wherein the second container is provided with a medicament different from the compound disclosed herein, wherein the medicament different from the compound disclosed herein is for use in preventing, treating or lessening a disease related to one or more orexin receptors.

In another aspect, provided herein is the method for preparing, separating, and purifying the compounds represented by Formula (I) to (IV).

Biological test results show that the compounds provided herein have a good antagonism for $OX_1$ receptor and better antagonism for $OX_2$ receptor, and show better pharmacokinetic properties in vivo of rat, dog and monkey, which can be used as a preferable orexin receptors antagonist.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limited in nature. These aspects and other aspects and embodiments are described more fully below.

SUMMARY OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limiting to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all scientific and technical terms used herein have the same meaning as is commonly understood by one skilled in the art to which this invention belongs. All patents and publications referred to herein are incorporated by reference in their entirety.

The grammatical articles "a", "an" and "the", as used herein, are intended to include "at least one" or "one or more" unless otherwise indicated herein or clearly contradicted by the context. Thus, the articles used herein refer to one or more than one (i.e. at least one) of the grammatical objects of the article. For example, "an embodiment" refers to one or more embodiments.

The term "optional" or "optionally" refers to that a subsequently described event or circumstance may but need not occur, and that the description includes instances where the event or circumstance occurs and instances in which it does not.

The term "optionally substituted" and "unsubstituted or substituted" can be used interchangeably herein, which means that the structure is unsubstituted or substituted by one or more substituents disclosed herein, wherein the substitution occurs at any valence allowable and reasonable site of structures or groups provided herein.

In general, the term "substituted" refers to the replacement of one or more hydrogen radicals in a given structure or group with the radical of a specified substituent. Unless otherwise indicated, a substituent may have a substituent at each substitutable and reasonable position of the group. When more than one position in a given structure can be substituted with more than one substituent selected from a specified group, the substituent may be either the same or different at each position. The substituents disclosed herein including, but not limited to D, F, Cl, Br, I, —$N_3$, —CN, —$NO_2$, —OH, —SH, —$NH_2$, alkyl, alkenyl, alkynyl, haloalkyl, alkoxy, alkylthio, alkylamino, cycloalkyl, heterocyclyl, aryl, heteroaryl, and the like.

The term "comprise" is an open expression, it means comprising the contents disclosed herein, but don't exclude other contents.

At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

The term "D" refers to a single deuterium atom.

The term "heteroatom" refers to oxygen (O), sulfur (S), nitrogen (N), phosphorus (P), or silicon (Si), including any oxidized form of nitrogen (N), sulfur (S), or phosphorus (P); the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "halogen" or "halo" are used interchangeably in this invention, and refers to Fluoro (F), Chloro (Cl), Bromo (Br), or Iodo (I).

The term "alkyl" or "alkyl group" refers to a saturated linear or branched-chain monovalent hydrocarbon group of 1-20 carbon atoms, wherein the alkyl group is optionally substituted with one or more substituents described herein. In one embodiment, the alkyl group contains 1-6 carbon atoms. In other embodiment, the alkyl group contains 1-4 carbon atoms. In still other embodiment, the alkyl group contains 1-3 carbon atoms. Some non-limiting examples of the alkyl group include, but are not limited to methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), and the like.

The term "alkenyl" refers to a linear or branched-chain monovalent hydrocarbon radical containing 2 to 12 carbon atoms and at least one carbon-carbon, sp2 double bond, and includes radicals having "cis" and "trans" orientations, or alternatively, "E" and "Z" orientations. The alkenyl radical may be optionally substituted with one or more substituents described herein.

The term "alkynyl" refers to a linear or branched monovalent hydrocarbon radical containing 2 to 12 carbon atoms and at least one carbon-carbon, sp triple bond, wherein the alkynyl radical may be optionally substituted with one or more substituents described herein.

The term "alkoxy" refers to an alkyl group, as previously defined, attached to the parent molecular moiety via an oxygen atom. Unless otherwise specified, the alkoxy group contains 1-12 carbon atoms. In one embodiment, the alkoxy group contains 1-6 carbon atoms. In other embodiment, the alkoxy group contains 1-4 carbon atoms. In still other embodiment, the alkoxy group contains 1-3 carbon atoms. The alkoxy group may be optionally substituted with one or more substituents disclosed herein.

Some non-limiting examples of the alkoxy group include, but are not limited to methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), and the like.

The term "haloalkyl" refers to an alkyl group substituted with one or more halogen atoms, wherein the alkyl group is as defined herein. Some non-limiting examples of such groups include, but are not limited to —CF$_3$, —CF$_2$CF$_3$, —CH$_2$CF$_2$CHF$_2$, and the like. In one embodiment, "haloalkyl" refers to a lower C$_{1-4}$ haloalkyl, wherein the "C$_{1-4}$ haloalkyl" includes fluorine-substituted C$_{1-4}$ alkyl, chlorine-substituted C$_{1-4}$ alkyl, bromine-substituted C$_{1-4}$ alkyl, iodine-substituted C$_{1-4}$ alkyl, and the like. Specifically, fluorine-substituted C$_{1-4}$ alkyl includes —CH$_2$F, —CHF$_2$, —CF$_3$, —CH$_2$CH$_2$F, —CH$_2$CHF$_2$, —CH$_2$CF$_3$, —CF$_2$CH$_2$F, —CF$_2$CHF$_2$, —CF$_2$CF$_3$, —CHFCF$_3$, —CHFCHF$_2$, —CHFCH$_2$F, —CH$_2$CH$_2$CF$_3$, —CH$_2$CF$_2$CHF$_2$ and the like. The haloalkyl is optionally substituted with one or more substituents described herein.

The term "haloalkoxy" refers to an alkoxy group substituted with one or more halogen atoms, wherein the alkoxy group is as defined herein. Some non-limiting examples of such groups include, but are not limited to —OCF$_3$, —OCF$_2$CF$_3$, —OCH$_2$CF$_2$CHF$_2$, and the like. The haloalkoxy is optionally substituted with one or more substituents described herein.

The term "alkylamino" embraces "N-alkylamino" and "N,N-dialkylamino", wherein an amino group is independently substituted with one or two alkyl radicals and wherein the alkyl group is as defined herein.

The term "hydroxy-substituted alkyl" refers to an alkyl group substituted with one or more hydroxy groups, wherein the alkyl group is as defined herein. Some non-limiting examples of such group include, but are not limited to hydroxymethyl, hydroxyethyl, 1,2-dihydroxyethyl, and the like.

The terms "carbocyclyl" and "carbocycle" as used interchangeably herein, refer to a monovalent or multivalent ring having 3 to 12 carbon atoms as a monocyclic, bicyclic or tricyclic ring system, which is saturated or contains one or more degrees of unsaturation, but an aromatic ring can not exist in the carbocyclyl group.

The terms "heterocyclyl" and "heterocycle" as used interchangeably herein refer to a monovalent or multivalent monocyclic, bicyclic or tricyclic ring containing 3-12 carbon atoms, wherein each one or more atoms in the ring is independently replaced with heteroatom, the heteroatom is as defined herein, and the ring may be saturated or contains one or more degrees of unsaturations, but an aromatic ring can not exist in the heterocyclyl ring.

The term "cycloalkyl" refers to a monovalent or multivalent saturated ring having 3 to 12 ring carbon atoms as a monocyclic, bicyclic, or tricyclic ring system.

The term "aryl" refers to a monovalent or multivalent monocyclic, bicyclic, or tricyclic carbocyclic ring system having a total of 6 to 14 ring members, preferably, 6 to 10 ring members, and more preferably 6 ring members, and wherein at least one ring in the system is aromatic. The aryl group is generally, but not necessarily bonded to the parent molecule through an aromatic ring of the aryl group. The terms "aryl" and "aromatic ring" can be used interchangeably herein. Examples of the aryl group may include phenyl, naphthyl, anthryl, and the like. The aryl radical is optionally substituted with one or more substituents described herein.

The term "heteroaryl" refers to a monovalent or multivalent monocyclic, bicyclic, or tricyclic ring system having a total of 5 to 14 ring members, preferably, 5 to 10 ring members, and more preferably 5 to 6 ring members, and wherein at least one ring in the system is aromatic, and at least one ring contains one or more heteroatoms. The heteroaryl group is generally, but not necessarily bonded to the parent molecule through an aromatic ring of the heteroaryl group. The term "heteroaryl" and "heteroaromatic ring" or "heteroaromatic compound" can be used interchangeably herein. The heteroaryl group is optionally substituted with one or more substituents disclosed herein.

The term "Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994, all of which are incorporated herein by reference. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, wherein (−) or l means that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); *Principles of Asymmetric Synthesis* (2$^{nd}$ Ed. Robert E. Gawley, Jeffrey Aube, Elsevier, Oxford, UK, 2012); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972); Chiral Separation Techniques: A Practical Approach (Subramanian, G. Ed., Wiley-VCH Verlag GmbH & Co. KGaA, Weinheim, Germany, 2007).

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The term "prodrug" refers to a compound that is transformed in vivo into a compound of Formula (I) to (IV). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_{1-24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, Nature Review Drug Discovery, 2008, 7, 255-270, and S. J. Hecker et al., Prodrugs of Phosphates and Phosphonates, Journal of Medicinal Chemistry, 2008, 51, 2328-2345, each of which is incorporated herein by reference.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in *J. Pharmaceutical Sciences*, 1977, 66: 1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts derived from appropriate bases include alkali metal, alkaline earth metal, ammonium and $N_+(C_{1-4}$ alkyl$)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "solvate" refers to an association or complex of one or more solvent molecules and a compound disclosed herein. Examples of solvents that form solvates include, but are not limited to, water, isopropanol, ethanol, methanol, DMSO, ethyl acetate, acetic acid, ethanolamine and the mixture thereof. The term "hydrate" refers to the complex where the solvent molecule is water.

The term "hydrate" can be used when said solvent is water. In one embodiment, one water molecule is associated with one molecule of the compounds disclosed herein, such as a hydrate. In another embodiment, more than one water molecule may be associated with one molecule of the compounds disclosed herein, such as a dihydrate. In still another embodiment, less than one water molecule may be associated with one molecule of the compounds disclosed herein, such as a hemihydrate. Furthermore, all the solvates of the invention retain the biological effectiveness of the non-hydrate form of the compounds disclosed herein.

As used herein, the term "therapeutically effective amount" or "therapeutically effective dose" refers to the amount of compound disclosed herein that can elicit the biological or medical response (such as reducing or inhibiting the activity of a enzyme or protein, or improving symptoms, lessening disorders, slowing or delaying the development of diseases and the like).

Description of Compounds of the Invention

Provided herein are octahydropyrrolo[3,4-c]pyrrole derivatives, pharmaceutically acceptable salts, pharmaceutical compositions and pharmaceutical preparations thereof, which have orexin receptor antagonist activities, and can be used as a orexin receptors antagonist for preventing or treating diseases related to orexin receptors, such as sleep disorders, psychiatry, neurology and neurodegenerative disorders, drug dependence, addiction, cognitive disorders, movement disorders, eating disorders, and the like.

In one aspect, the present invention relates to a compound having Formula (I) or a stereoisomer, a tautomer, an N-oxide, a solvate, a metabolite, a pharmaceutically acceptable salt or a prodrug thereof, (I)

wherein X is —O—, —S—, —NH—, *—CR$^9$═N— or *—CR$^9$═CR$^{9a}$—, wherein * refers to an end attached to the benzene ring;

Hy is triazolyl, and wherein the triazolyl is optionally substituted by one or more substituents independently selected from halogen, oxo (═O), $C_{1-6}$ alkyl, $C_{1-6}$ haloalkyl, $C_{1-6}$ alkoxy and benzyl;

R$^1$, R$^2$, R$^3$, R$^4$, R$^9$, R$^{9a}$, R$^5$, R$^6$, R$^7$ and R$^8$ are as defined herein; and when X is —O—, at least one of R$^1$, R$^2$, R$^3$, R$^4$, R$^5$, R$^6$, R$^7$ and $^8$ is not H.

In some embodiments, Hy of Formula (I) is one of the following sub-structures represented by Formulae i-1 to i-14:

(i-1)

(i-2)

(i-3)

(i-4)

(i-5)

(i-6)

(i-7)

(i-8)

(i-9)

(i-10)

(i-11)

(i-12)

-continued (i-13)

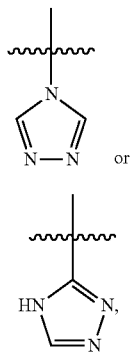

or (i-14)

wherein sub-structures represented by Formulae i-1 to i-14 is optionally substituted by one or more substituents independently selected from halogen, oxo (═O), $C_{1-6}$ alkyl, $C_{1-6}$ haloalkyl, $C_{1-6}$ alkoxy or benzyl.

In one embodiment, provided herein is a compound having Formula (II) or a stereoisomer, a tautomer, an N-oxide, a solvate, a metabolite, a pharmaceutically acceptable salt or a prodrug thereof, (II)

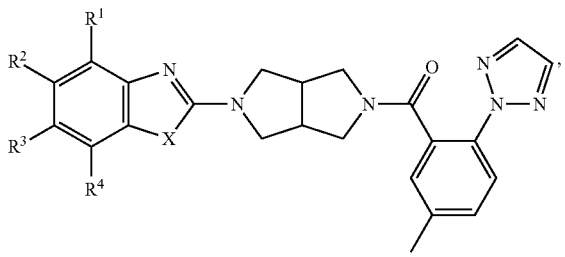

wherein X is —O—, —S—, —NH—, *—$CR^9$═N— or *—$CR^9$═$CR^{9a}$—, wherein * refers to an end attached to the benzene ring; and $R^1$, $R^2$, $R^3$, $R^4$, $R^9$ and $R^{9a}$ are as defined herein.

In one embodiment, provided herein is a compound having Formula (III) or a stereoisomer, a tautomer, an N-oxide, a solvate, a metabolite, a pharmaceutically acceptable salt or a prodrug thereof, (III)

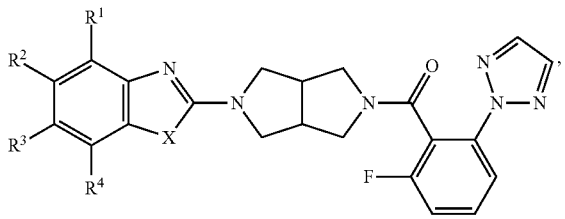

wherein X is —O—, —S—, —NH—, *—$CR^9$═N— or *—$CR^9$═$CR^{9a}$—, wherein * refers to an end attached to the benzene ring; and $R^1$, $R^2$, $R^3$, $R^4$, $R^9$ and $R^{9a}$ are as defined herein.

In one embodiment, provided herein is a compound having Formula (IV) or a stereoisomer, a tautomer, an N-oxide, a solvate, a metabolite, a pharmaceutically acceptable salt or a prodrug thereof, (IV)

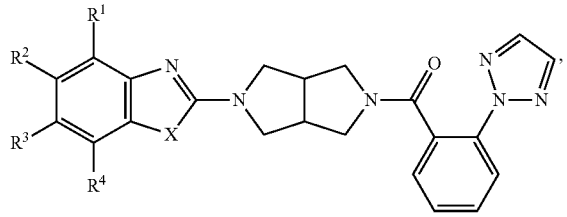

wherein X is —O—, —S—, —NH—, *—$CR^9$═N— or *—$CR^9$═$CR^{9a}$—, wherein * refers to an end attached to the benzene ring;

when X is —O—, at least one of $R^1$, $R^2$, $R^3$ and $R^4$ is not H; and $R^1$, $R^2$, $R^3$, $R^4$, $R^9$ and $R^{9a}$ are as defined herein.

In one embodiment, each $R^1$ of Formula (I), (II), (III) or (IV) is independently H, D, —$CD_3$, —CN, —$NH_2$, —OH, —$NO_2$, —COOH, —C(═O)$NH_2$, halogen, alkyl, alkenyl, alkynyl, haloalkyl, alkoxy, haloalkoxy, alkylamino, hydroxy-substituted alkyl, alkyl-C(═O)—, alkoxy-C(═O)—, alkylamino-C(═O)—, cycloalkyl, heterocyclyl, aryl or heteroaryl.

In one embodiment, each $R^2$ of Formula (I), (II), (III) or (IV) is independently H, D, —$CD_3$, —CN, —$NH_2$, —OH, —$NO_2$, —COOH, —C(═O)$NH_2$, halogen, alkyl, alkenyl, alkynyl, haloalkyl, alkoxy, haloalkoxy, alkylamino, hydroxy-substituted alkyl, alkyl-C(═O)—, alkoxy-C(═O)—, alkylamino-C(═O)—, cycloalkyl, heterocyclyl, aryl or heteroaryl.

In one embodiment, each $R^3$ of Formula (I), (II), (III) or (IV) is independently H, D, —$CD_3$, —CN, —$NH_2$, —OH, —$NO_2$, —COOH, —C(═O)$NH_2$, halogen, alkyl, alkenyl, alkynyl, haloalkyl, alkoxy, haloalkoxy, alkylamino, hydroxy-substituted alkyl, alkyl-C(═O)—, alkoxy-C(═O)—, alkylamino-C(═O)—, cycloalkyl, heterocyclyl, aryl or heteroaryl.

In one embodiment, each $R^4$ of Formula (I), (II), (III) or (IV) is independently H, D, —$CD_3$, —CN, —$NH_2$, —OH, —$NO_2$, —COOH, —C(═O)$NH_2$, halogen, alkyl, alkenyl, alkynyl, haloalkyl, alkoxy, haloalkoxy, alkylamino, hydroxy-substituted alkyl, alkyl-C(═O)—, alkoxy-C(═O)—, alkylamino-C(═O)—, cycloalkyl, heterocyclyl, aryl or heteroaryl.

In one embodiment, each $R^9$ and $R^{9a}$ of Formula (I), (II), (III) or (IV) is independently H, D, —$CD_3$, —CN, —$NH_2$, —OH, —$NO_2$, —COOH, —C(═O)$NH_2$, halogen, alkyl, alkenyl, alkynyl, haloalkyl, alkoxy, haloalkoxy, alkylamino, hydroxy-substituted alkyl, alkyl-C(═O)—, alkoxy-C(═O)—, alkylamino-C(═O)—, cycloalkyl, heterocyclyl, aryl or heteroaryl.

In one embodiment, $R^5$ of Formula (I) is H, D, F, Cl, Br, I, —CN, —$NH_2$, —OH, —$NO_2$, —COOH, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ hydroxy-substituted alkyl, ($C_{1-6}$ alkyl)-C(═O)—, ($C_{1-6}$ alkoxy)-C(═O)—, ($C_{1-6}$ alkylamino)-C(═O)—, cycloalkyl, heterocyclyl, aryl or heteroaryl.

In one embodiment, $R^6$ of Formula (I) is H, D, F, Cl, Br, I, —CN, —$NH_2$, —OH, —$NO_2$, —COOH, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ hydroxy-substituted alkyl, $(C_{1-6}$ alkyl)-C(=O)—, $(C_{1-6}$ alkoxy)-C(=O)—, $(C_{1-6}$ alkylamino)-C(=O)—, cycloalkyl, heterocyclyl, aryl or heteroaryl.

In one embodiment, $R^7$ of Formula (I) is H, D, F, Cl, Br, I, —CN, —NH$_2$, —OH, —NO$_2$, —COOH, $C_{1-6}$ alkyl, $C_{2-6}$ alkenyl, $C_{2-6}$ alkynyl, $C_{1-6}$ haloalkyl, $C_{2-6}$ alkoxy, $C_{1-6}$ haloalkoxy, $C_{1-6}$ alkylamino, $C_{1-6}$ hydroxy-substituted alkyl, $(C_{1-6}$ alkyl)-C(=O)—, $(C_{1-6}$ alkoxy)-C(=O)—, $(C_{1-6}$ alkylamino)-C(=O)—, cycloalkyl, heterocyclyl, aryl or heteroaryl.

In one embodiment, $R^8$ of Formula (I) is H, D, Cl, Br, I, —CN, —NH$_2$, —OH, —NO$_2$, —COOH, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ hydroxy-substituted alkyl, $(C_{1-6}$ alkyl)-C(=O)—, $(C_{1-6}$ alkoxy)-C(=O)—, $(C_{1-6}$ alkylamino)-C(=O)—, cycloalkyl, heterocyclyl, aryl or heteroaryl.

In one embodiment, R' of Formula (I), (II), (III) or (IV) is H, D, —CD$_3$, —CN, —NH$_2$, —OH, —NO$_2$, —COOH, —C(=O)NH$_2$, halogen, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ hydroxy-substituted alkyl, $(C_{1-6}$ alkyl)-C(=O)—, $(C_{1-6}$ alkoxy)-C(=O)— or $(C_{1-6}$ alkylamino)-C(=O)—.

In one embodiment, $R^2$ of Formula (I), (II), (III) or (IV) is H, D, —CD$_3$, —CN, —NH$_2$, —OH, —NO$_2$, —COOH, —C(=O)NH$_2$, halogen, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ hydroxy-substituted alkyl, $(C_{1-6}$ alkyl)-C(=O)—, $(C_{1-6}$ alkoxy)-C(=O)— or $(C_{1-6}$ alkylamino)-C(=O)—.

In one embodiment, $R^3$ of Formula (I), (II), (III) or (IV) is H, D, —CD$_3$, —CN, —NH$_2$, —OH, —NO$_2$, —COOH, —C(=O)NH$_3$, halogen, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ hydroxy-substituted alkyl, $(C_{1-6}$ alkyl)-C(=O)—, $(C_{1-6}$ alkoxy)-C(=O)— or $(C_{1-6}$ alkylamino)-C(=O)—.

In one embodiment, $R^4$ of Formula (I), (II), (III) or (IV) is H, D, —CD$_3$, —CN, —NH$_2$, —OH, —NO$_2$, —COOH, —C(=O)NH$_2$, halogen, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ hydroxy-substituted alkyl, $(C_{1-6}$ alkyl)-C(=O)—, $(C_{1-6}$ alkoxy)-C(=O)— or $(C_{1-6}$ alkylamino)-C(=O)—.

In one embodiment, each $R^9$ and $R^{9a}$ of Formula (I), (II), (III) or (IV) is independently H, D, —CD$_3$, —CN, —NH$_2$, —OH, —NO$_2$, —COOH, —C(=O)NH$_2$, halogen, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ hydroxy-substituted alkyl, $(C_{1-6}$ alkyl)-C(=O)—, $(C_{1-6}$ alkoxy)-C(=O)— or $(C_{1-6}$ alkylamino)-C(=O)—.

In one embodiment, $R^1$ of Formula (I), (II), (III) or (IV) is H, D, —CD$_3$, —CN, —NH$_2$, —OH, —NO$_2$, —COOH, —C(=O)NH$_2$, halogen, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ haloalkoxy, $C_{1-4}$ alkylamino, $C_{1-4}$ hydroxy-substituted alkyl, $(C_{1-4}$ alkyl)-C(=O)—, $(C_{1-4}$ alkoxy)-C(=O)— or $(C_{1-4}$ alkylamino)-C(=O)—.

In one embodiment, $R^2$ of Formula (I), (II), (III) or (IV) is H, D, —CD$_3$, —CN, —NH$_2$, —OH, —NO$_2$, —COOH, —C(=O)NH$_2$, halogen, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ haloalkoxy, $C_{1-4}$ alkylamino, $C_{1-4}$ hydroxy-substituted alkyl, $(C_{1-4}$ alkyl)-C(=O)—, $(C_{1-4}$ alkoxy)-C(=O)— or $(C_{1-4}$ alkylamino)-C(=O)—.

In one embodiment, $R^3$ of Formula (I), (II), (III) or (IV) is H, D, —CD$_3$, —CN, —NH$_2$, —OH, —NO$_2$, —COOH, —C(=O)NH$_2$, halogen, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ haloalkoxy, $C_{1-4}$ alkylamino, $C_{1-4}$ hydroxy-substituted alkyl, $(C_{1-4}$ alkyl)-C(=O)—, $(C_{1-4}$ alkoxy)-C(=O)— or $(C_{1-4}$ alkylamino)-C(=O)—.

In one embodiment, $R^4$ of Formula (I), (II), (III) or (IV) is H, D, —CD$_3$, —CN, —NH$_2$, —OH, —NO$_2$, —COOH, —C(=O)NH$_2$, halogen, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ haloalkoxy, $C_{1-4}$ alkylamino, $C_{1-4}$ hydroxy-substituted alkyl, $(C_{1-4}$ alkyl)-C(=O)—, $(C_{1-4}$ alkoxy)-C(=O)— or $(C_{1-4}$ alkylamino)-C(=O)—.

In one embodiment, $R^5$ of Formula (I) is H, D, Cl, Br, I, —CN, —NH$_2$, —OH, —NO$_2$, —COOH, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ haloalkoxy, $C_{1-4}$ alkylamino, $C_{1-4}$ hydroxy-substituted alkyl, $(C_{1-4}$ alkyl)-C(=O)—, $(C_{1-4}$ alkoxy)-C(=O)— or $(C_{1-4}$ alkylamino)-C(=O)—.

In one embodiment, $R^6$ of Formula (I) is H, D, F, Cl, Br, I, —CN, —NH$_2$, —OH, —NO$_2$, —COOH, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ haloalkoxy, $C_{1-4}$ alkylamino, $C_{1-4}$ hydroxy-substituted alkyl, $(C_{1-4}$ alkyl)-C(=O)—, $(C_{1-4}$ alkoxy)-C(=O)— or $(C_{1-4}$ alkylamino)-C(=O)—.

In one embodiment, $R^7$ of Formula (I) is H, D, F, Cl, Br, I, —CN, —NH$_2$, —OH, —NO$_2$, —COOH, $C_{1-4}$ alkyl, $C_{2-4}$ alkenyl, $C_{2-4}$ alkynyl, $C_{1-4}$ haloalkyl, $C_{2-4}$ alkoxy, $C_{1-4}$ haloalkoxy, $C_{1-4}$ alkylamino, $C_{1-4}$ hydroxy-substituted alkyl, $(C_{1-4}$ alkyl)-C(=O)—, $(C_{1-4}$ alkoxy)-C(=O)— or $(C_{1-4}$ alkylamino)-C(=O)—.

In one embodiment, $R^8$ of Formula (I) is H, D, Cl, Br, I, —CN, —NH$_2$, —OH, —NO$_2$, —COOH, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ haloalkoxy, $C_{1-4}$ alkylamino, $C_{1-4}$ hydroxy-substituted alkyl, $(C_{1-4}$ alkyl)-C(=O)—, $(C_{1-4}$ alkoxy)-C(=O)— or $(C_{1-4}$ alkylamino)-C(=O)—.

In one embodiment, each of $R^9$ and $R^{9a}$ of Formula (I), (II), (III) or (IV) is independently is H, D, —CD$_3$, —CN, —NH$_2$, —OH, —NO$_2$, —COOH, —C(=O)NH$_2$, halogen, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ haloalkoxy, $C_{1-4}$ alkylamino, $C_{1-4}$ hydroxy-substituted alkyl, $(C_{1-4}$ alkyl)-C(=O)—, $(C_{1-4}$ alkoxy)-C(=O)— or $(C_{1-4}$ alkylamino)-C(=O)—.

In one embodiment, IV of Formula (I), (II), (III) or (IV) is H, D, —CD$_3$, —CN, —NH$_2$, —OH, —NO$_2$, —COOH, —C(=O)NH$_2$, F, Cl, Br, I, methyl, ethyl, n-propyl, isopropyl, —CF$_3$, —CH$_2$CF$_3$, —CF$_2$CF$_3$, methoxy, ethoxy, n-propyloxy, isopropyloxy, —NHCH$_3$, —N(CH$_3$)$_2$ or —CH$_2$OH.

In one embodiment, $R^2$ of Formula (I), (II), (III) or (IV) is H, D, —CD$_3$, —CN, —NH$_2$, —OH, —NO$_2$, —COOH, —C(=O)NH$_2$, F, Cl, Br, I, methyl, ethyl, n-propyl, isopropyl, —CF$_3$, —CH$_2$CF$_3$, —CF$_2$CF$_3$, methoxy, ethoxy, n-propyloxy, isopropyloxy, —NHCH$_3$, —N(CH$_3$)$_2$ or —CH$_2$OH.

In one embodiment, $R^3$ of Formula (I), (II), (III) or (IV) is H, D, —CD$_3$, —CN, —NH$_2$, —OH, —NO$_2$, —COOH, —C(=O)NH$_2$, F, Cl, Br, I, methyl, ethyl, n-propyl, isopropyl, —CF$_3$, —CH$_2$CF$_3$, —CF$_2$CF$_3$, methoxy, ethoxy, n-propyloxy, isopropyloxy, —NHCH$_3$, —N(CH$_3$)$_2$ or —CH$_2$OH.

In one embodiment, $R^4$ of Formula (I), (II), (III) or (IV) is H, D, —CD$_3$, —CN, —NH$_2$, —OH, —NO$_2$, —COOH, —C(=O)NH$_2$, F, Cl, Br, I, methyl, ethyl, n-propyl, isopropyl, —CF$_3$, —CH$_2$CF$_3$, —CF$_2$CF$_3$, methoxy, ethoxy, n-propyloxy, isopropyloxy, —NHCH$_3$, —N(CH$_3$)$_2$ or —CH$_2$OH.

In one embodiment, $R^5$ of Formula (I) is H, D, F, Cl, Br, I, —CN, —NH$_2$, —OH, —NO$_2$, —COOH, methyl, ethyl, n-propyl, isopropyl, —CF₃, —CH₂CF₃, —CF₂CF₃, methoxy, ethoxy, n-propyloxy, isopropyloxy, —NHCH₃, —N(CH₃)₂ or —CH₂OH.

In one embodiment, R⁶ of Formula (I) is H, D, F, Cl, Br, I, —CN, —NH₂, —OH, —NO₂, —COOH, methyl, ethyl, n-propyl, isopropyl, —CF₃, —CH₂CF₃, —CF₂CF₃, methoxy, ethoxy, n-propyloxy, isopropyloxy, —NHCH₃, —N(CH₃)₂ or —CH₂OH.

In one embodiment, R⁷ of Formula (I) is H, D, F, Cl, Br, I, —CN, —NH₂, —OH, —NO₂, —COOH, methyl, ethyl, n-propyl, isopropyl, —CF₃, —CH₂CF₃, —CF₂CF₃, ethoxy, n-propyloxy, isopropyloxy, —NHCH₃, —N(CH₃)₂ or —CH₂OH.

In one embodiment, R⁸ of Formula (I) is H, D, Cl, Br, I, —CN, —NH₂, —OH, —NO₂, —COOH, methyl, ethyl, n-propyl, isopropyl, —CF₃, —CH₂CF₃, —CF₂CF₃, methoxy, ethoxy, n-propyloxy, isopropyloxy, —NHCH₃, —N(CH₃)₂ or —CH₂OH.

In one embodiment, each R⁹ and R⁹ᵃ of Formula (I), (II), (III) or (IV) is independently H, D, —CD₃, —CN, —NH₂, —OH, —NO₂, —COOH, —C(=O)NH₂, F, Cl, Br, I, methyl, ethyl, n-propyl, isopropyl, —CF₃, —CH₂CF₃, —CF₂CF₃, methoxy, ethoxy, n-propyloxy, isopropyloxy, —NHCH₃, —N(CH₃)₂ or —CH₂OH.

In yet another embodiment, provided herein is a compound having one of the following structures or a stereoisomer, a tautomer, an N-oxide, a solvate, a metabolite, a pharmaceutically acceptable salt or a prodrug thereof, (1)

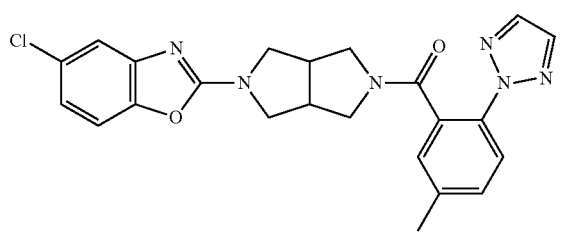

(2)

(3)

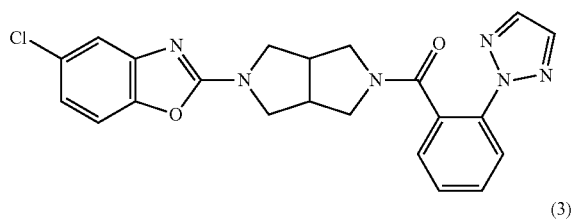

(4)

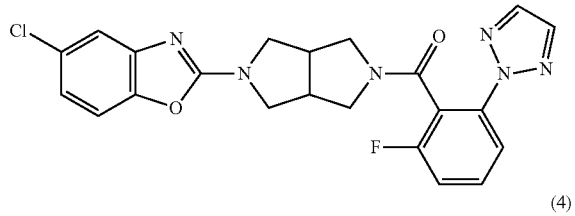

(5)

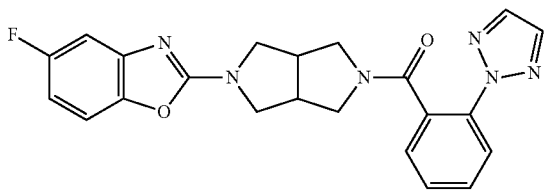

(6)

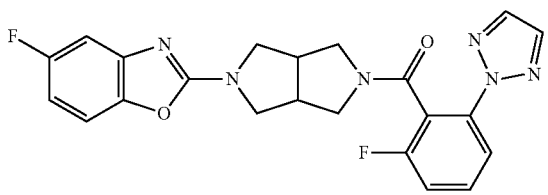

(7)

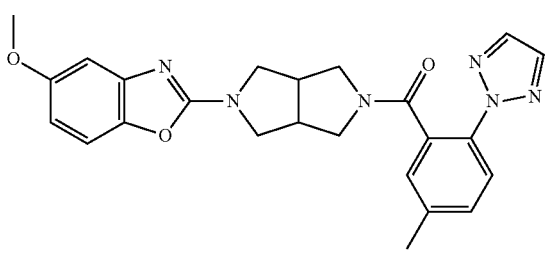

(8)

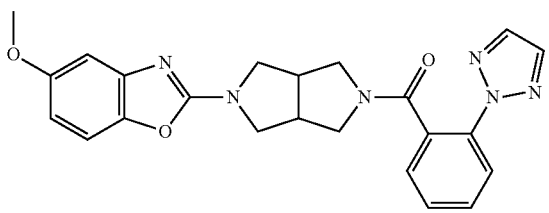

(9)

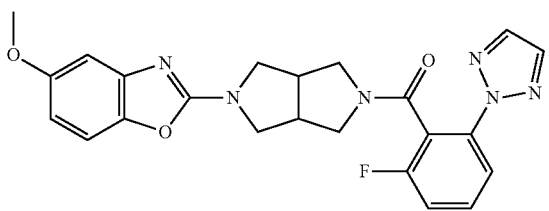

(10)

(11)

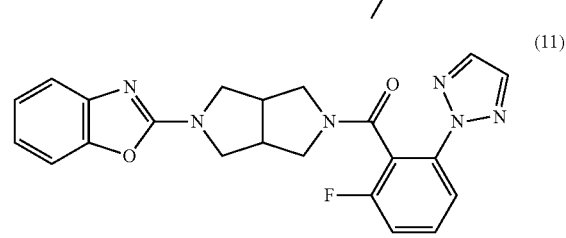

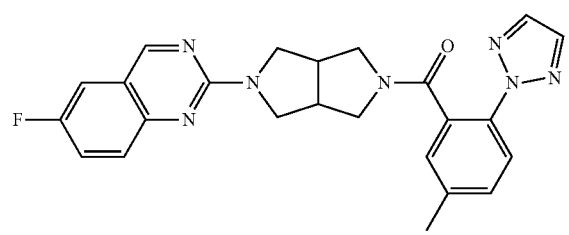
(12)
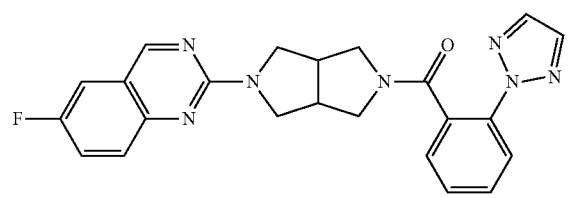
(13)
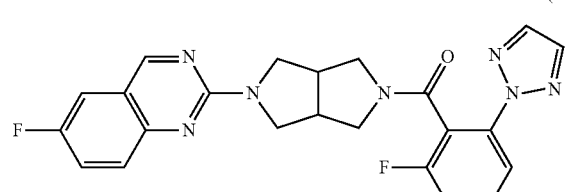
(14)
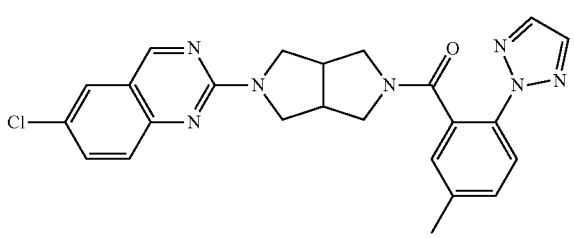
(15)
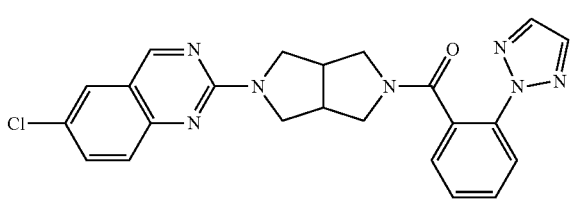
(16)
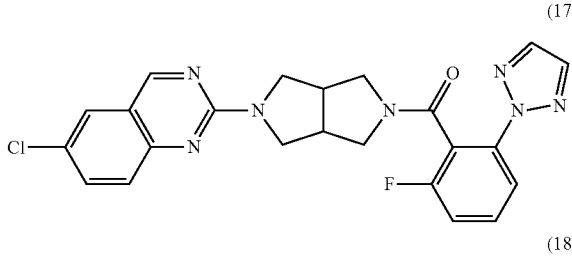
(17)
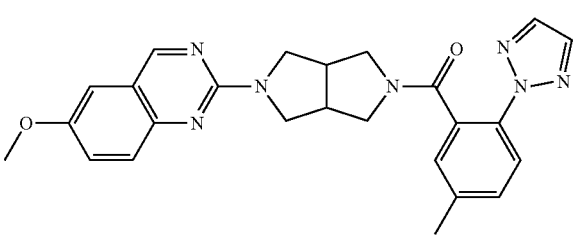
(18)
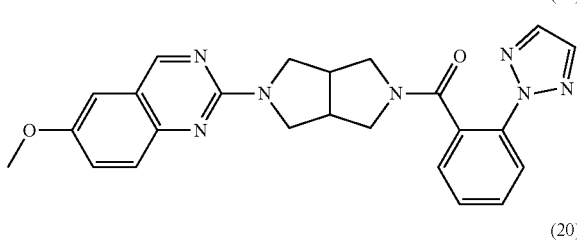
(19)
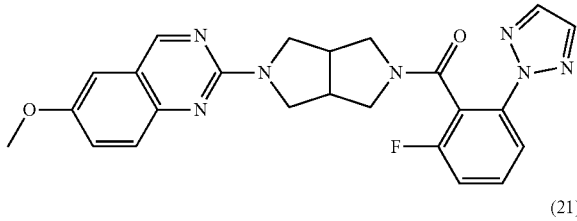
(20)
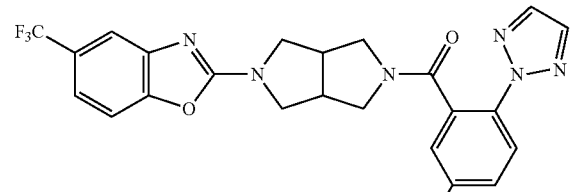
(21)
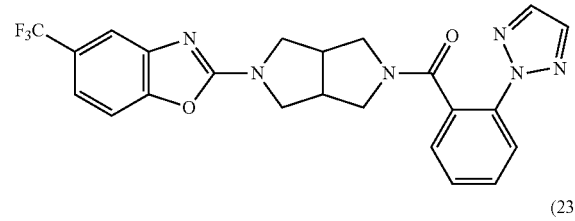
(22)
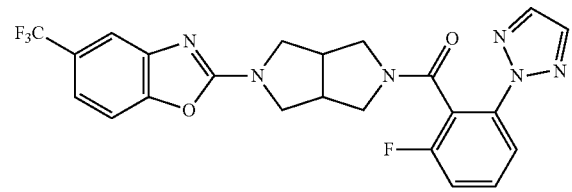
(23)
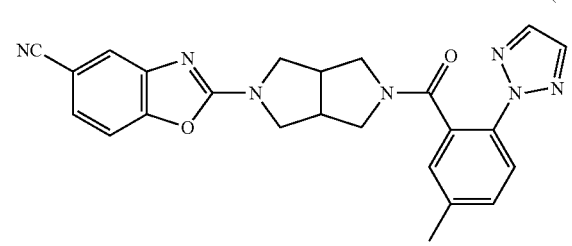
(24)
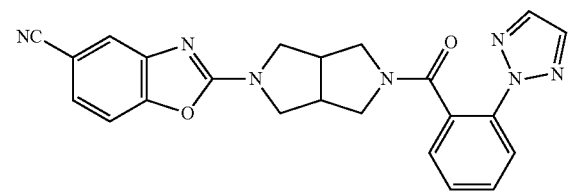
(25)

(26)
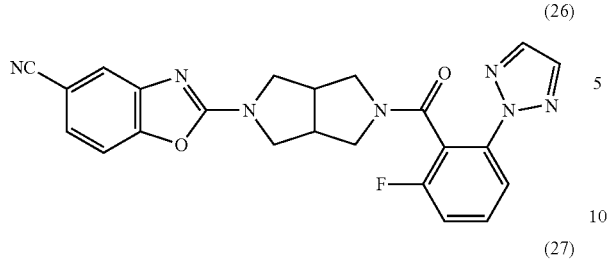
(27)
(28)
(29)
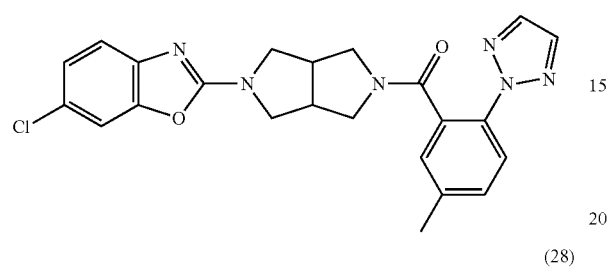
(30)
(31)
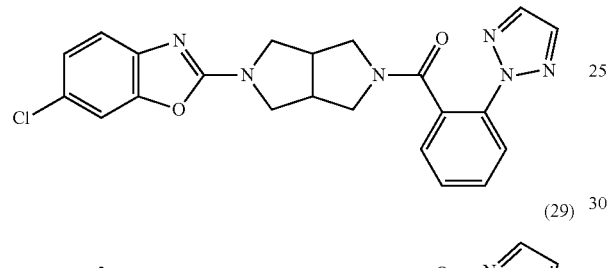
(32)
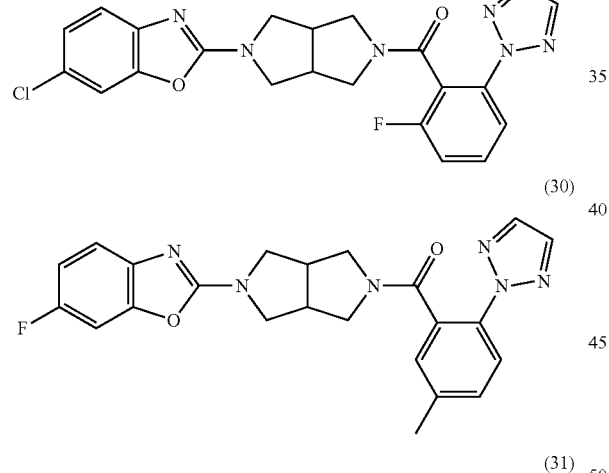
(33)
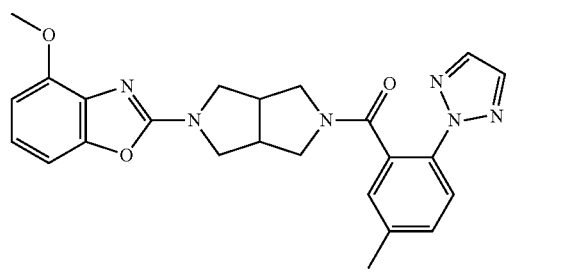
(34)
(35)
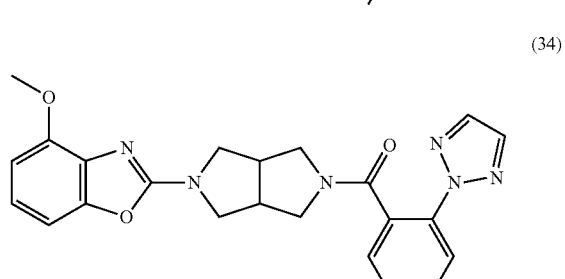
(36)
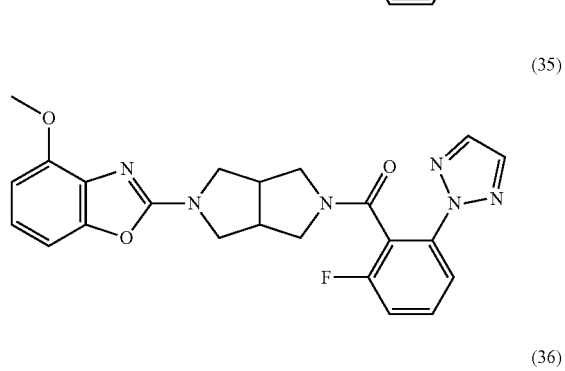
(37)
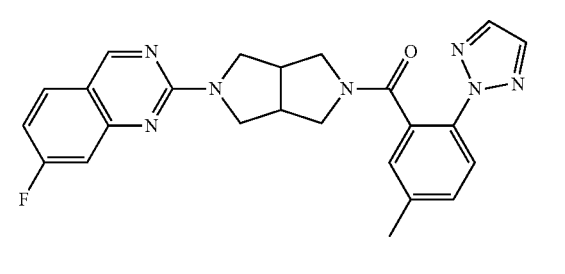
(38)
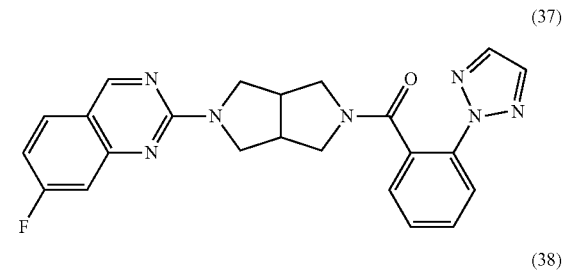
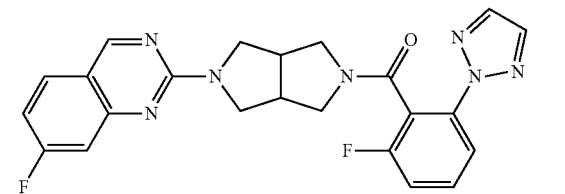

(39)
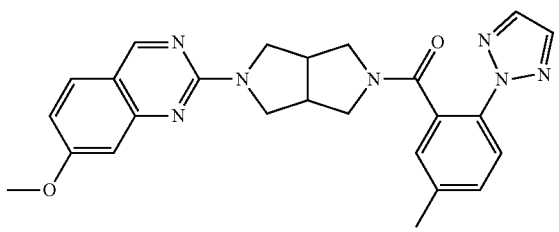

(40)
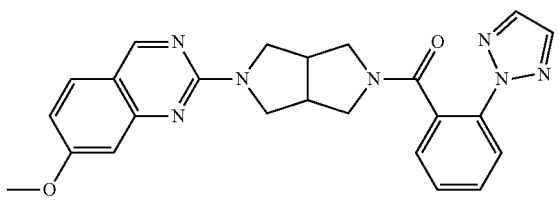

(41)
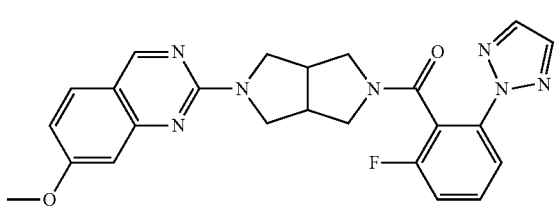

(42)
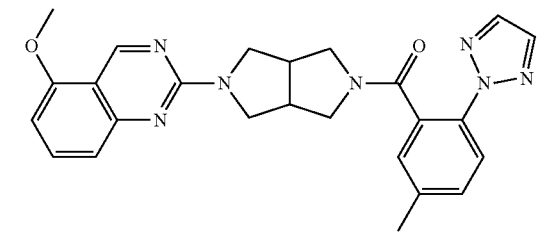

(43)
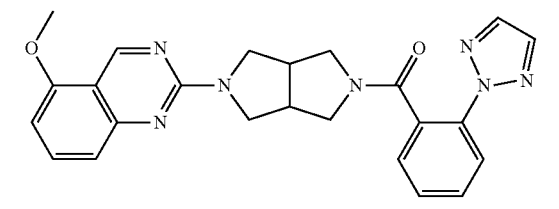

(44)
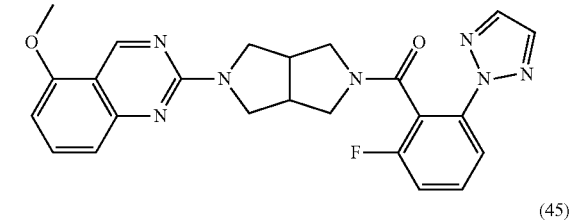

(45)
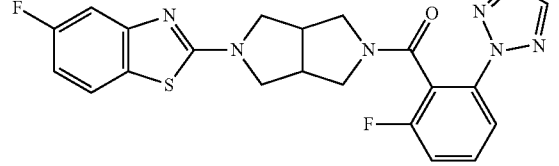

(46)
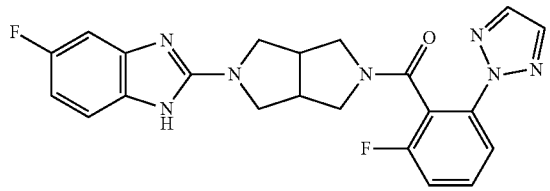

(47)
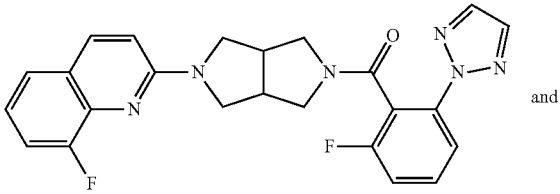

and

(48)
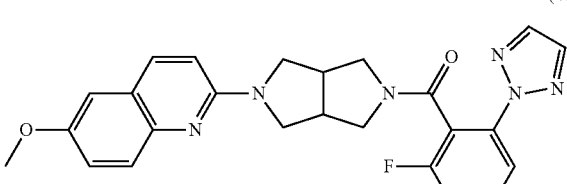

Unless otherwise stated, all suitable isotope changes, stereoisomers, tautomers, solvates, metabolites, salts and pharmaceutically acceptable prodrugs of the compounds disclosed herein are within the scope of the invention.

The compounds shown in Formula (I) to (IV) may exist in different tautomeric forms, and all of these tautomers are contemplated within the scope of the present invention.

N-Oxides of the compounds disclosed herein are also within the scope of the invention. N-Oxides of the compounds disclosed herein may be prepared by oxidation of the corresponding nitrogen base using a conventional oxidizing agent (such as hydrogen peroxide) in the presence of an acid such as acetic acid at an elevated temperature, or by reaction with a peracid such as peracetic acid in a suitable solvent, e.g. DCM, ethyl acetate or methyl acetate, or in chloroform or DCM with 3-chloroperoxybenzoic acid.

Moreover, when compounds disclosed herein form hydrates or solvates, which are within the scope of the invention. Similarly, the pharmaceutical acceptable salts of hydratas and solvates of compounds disclosed herein are also within the scope of the invention.

The compounds of Formula (I) to (IV) can exist in the form of salts. In some embodiments, the salt is a pharmaceutically acceptable salt. The pharmaceutically acceptable salts of the present invention can be synthesized from a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985);

and in "Handbook of Pharmaceutical Salts: Properties, Selection, and Use" by Stahl and Wermuth (Wiley-VCH, Weinheim, Germany, 2002).

Compounds of the present invention are basic, thus pharmaceutically acceptable acid addition salts can be formed generally by processing a suitable acid. The suitable acid includes pharmaceutically acceptable inorganic acid and organic acid. Representative pharmaceutically acceptable acid addition salts include hydrochloride, hydrobromide, nitrate, methylnitrate, sulfate, hydrosulfate, sulfamate, phosphate, acetate, glycolate, phenyl acetate, propionate, butyrate, isobutyrate, valerate, maleate, hydroxymaleate, acrylate, fumarate, malate, tartrate, citrate, salicylate, para-amino salicylate, glycollate, lactate, enantate, phthalate, oxalate, succinate, benzoate, acetoxybenzoate, chlorobenzoate, methylbenzoate, binitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, mesylate, ethyl sulfate, 2-hydroxyesilate, benzene sulfonate, para-amino benzene sulfonate, para-methylbenzene sulfonate and naphthalene-2-sulfonate, and the like.

Any formula given herein is also intended to represent isotopically unenriched forms as well as isotopically enriched forms of the compounds. Isotopically enriched compounds have the structure represented by the general formula of the present invention, but for the fact that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine and chlorine, such as $^{2}H$, $^{3}H$, $^{11}C$, $^{13}C$, $^{14}C$, $^{15}N$, $^{17}O$, $^{18}O$, $^{18}F$, $^{3}P$, $^{32}P$, $^{35}S$, $^{36}Cl$ and $^{125}I$.

In another aspect, the compounds of the invention include isotopically enriched compounds as defined herein, for example, wherein radioisotopes exist, such as $^{3}H$, $^{14}C$ and $^{18}F$, or wherein non-radioactive isotopes exist, such as $^{2}H$ and $^{13}C$. Such isotopically enriched compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. $^{18}F$-enriched compounds are particularly desirable for PET or SPECT studies. Isotopically-enriched compounds of Formula (I) to (IV) can generally be prepared by conventional techniques known to those skilled in the art or by processes analogous to those described in the accompanying Examples and Preparations using an appropriate isotopically-labeled reagent in place of the non-labeled reagent previously employed.

In another aspect, the present invention relates to intermediates useful for the preparation of compounds represented by Formula (I) to (IV).

In another aspect, the present invention relates to methods for preparing, separating, and purifying the compounds represented by Formula (I) to (IV).

Pharmaceutical Composition of the Compound of the Invention and Preparations and Administration In one aspect, provided herein is a pharmaceutical composition including compounds of Formula (I) to (IV) or a stereoisomer, a tautomer, an N-oxide, a solvate, a metabolite, a pharmaceutically acceptable salt or a prodrug thereof. Optionally, the pharmaceutical compositions further comprise at least a pharmaceutically acceptable carrier, an adjuvant, or an excipient, and optionally other therapeutic and/or prophylactic ingredients.

Suitable carriers, adjuvants and excipients are well known to those skilled in the art and described in detail in such as Ansel H. C. et al., Ansel's Pharmaceutical Dosage Forms and Drug Delivery Systems (2004) Lippincott, Williams & Wilkins, Philadelphia; Gennaro A. R. et al., Remington: The Science and Practice of Pharmacy (2000) Lippincott, Williams & Wilkins, Philadelphia; and Rowe R. C., Handbook of Pharmaceutical Excipients (2005) Pharmaceutical Press, Chicago.

"Pharmaceutically acceptable excipient" as used herein means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions are avoided. In addition, each excipient must of course be of sufficiently high purity to render it pharmaceutically acceptable.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. One skilled in the art will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The compound of the invention will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable prodrugs, salts, esters, salts of such esters, or any other adduct or derivative which upon administration to a patient in need thereof is capable of providing, directly or indirectly, a compound as otherwise described herein, or a metabolite or residue thereof.

In one embodiment, the compounds disclosed herein can be prepared to oral dosage forms. In one embodiment, the compounds disclosed herein can be prepared to inhalation dosage forms. In one embodiment, the compounds disclosed herein can be prepared to dosage forms of nasal administration. In one embodiment, the compounds disclosed herein can be prepared to transdermal dosage forms. In one embodiment, the compounds disclosed herein can be prepared to dosage forms of topical administration.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxy groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Provided herein is a pharmaceutical composition which can be prepared to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In one embodiment, the invention is directed to a dosage form adapted for administration to a patient by inhalation as a dry powder. Dry powder compositions for delivery to the lung by inhalation typically comprise a compound disclosed herein or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling Generally, the size-reduced (eg micronised) compound can be defined by a $D_{50}$ value of about 1 to 10 microns (for example as measured using laser diffraction).

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in *Pharmaceutical Research*, 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or oil such as liquid paraffin or a vegetable oil such as *arachis* oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

The compounds disclosed herein can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

The pharmaceutical compositions provided herein may be formulated as immediate or modified release dosage forms, including delayed-, sustained-, pulsed-, controlled, targeted-, and programmed-release forms.

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

The pharmaceutical compositions provided herein may be co-formulated with other active ingredients which do not impair the desired therapeutic action, or with substances that supplement the desired action.

In one embodiment, the therapeutic methods disclosed herein comprise administrating to a patient in need of the treatment a safe and effective amount of the compound of the invention or the pharmaceutical composition containing the compound of the invention. Each example disclosed herein comprises treating the above disorders or diseases by administrating to a patient in need of the treatment a safe and effective amount of the compound of the invention or the pharmaceutical composition containing the compound of the invention.

In one embodiment, the compound of the invention or the pharmaceutical composition thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. In one embodiment, the compound of the invention or the pharmaceutical composition thereof may be administered orally. In one embodiment, the compound of the invention or the pharmaceutical composition thereof may be administered by inhalation. In a further embodiment, the compound of the invention or the pharmaceutical composition thereof may be administered intranasally.

In one embodiment, the compound of the invention or the pharmaceutical composition thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the compound of the invention or the pharmaceutical composition thereof depend on the pharmacokinetic properties of that compound, such as absorption, distribution, and half-life, which can be determined by the skilled artisan. In addition, suitable dosing regimens, including the duration such regimens are administered, for the compound of the invention or the pharmaceutical composition thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The compounds of the present invention may be administered either simultaneously with, or before or after, one or more other therapeutic agents. The compounds of the present invention may be administered separately, by the same or different route of administration, or together in the same pharmaceutical composition as the other agents.

Compounds provided herein can used in combination with sedative, hypnotic, anxiolytic, antipsychotic, antianxiety agent, cyclopyrrolidone, imidazopyridine, pyrazolopyrimidines, minor tranquilizer, melatonin agonist and antagonist, melatoninergic agent, benzodiazepine, barbiturate, 5HT-2 antagonist, and the like. For example: adinazolan, allobarbital, alonimid, alprazolam, amitriptyline, amobarbital, amoxapine, bentazepam, tacitin, brotizolam, bupropion, buspirone, butabarbital, butalbital, capuride, carbocloral, chloral betaine, chloral hydrate, chlorodyne, clomipramine, clonazepam, domperidone, methaminodiazepoxide, cloretate, clozapine, cyprazepam, desipramine, dexclamo, diazepam, chloralsalicylamide, divalproic acid, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, orazepam, lormetazepam, maprotiline, mecloqualone, melatonin, methylphenobarbital, meprobamate, methaqualone, midaflur, midazolam, nefazodone, nisobamate, nitrazepam, nortriptyline, oxezepam, paraaldehyde, paroxetine, pentobarbital, perlapine, perphenazine, phenelzine, phenobarbital, Prazepam, promethazine, isopropylphenol, protriptyline, quazepam, reclazepam, rolipram, secobarbital, sertraline, suproclone, temazepam, thioridazine, tracazolate, tranylcypromine, trazodone, triazole benzodiazepine, trepipam, tricetamide, trichloroethyl phosphate, trifluoperazine, trimetozine, trimeprimine, uldazepam, venlafaxine, zaleplon, zolazepam, zolpidem and the salts and compositions thereof, and the like. Alternatively, physical methods such as light therapy or electrical stimulation can be used during administration of compounds disclosed herein.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Use of the Compounds and Pharmaceutical Compositions

Compounds or pharmaceutical compositions disclosed herein are efficient as orexin receptors antagonists for treating or preventing a disease related to orexin receptors and may be used in preparation of a medicament antagonizing orexin receptors.

All diseases related to orexin receptors are selectable from all types of sleep disorders, all types of psychiatry, neurology and neurodegenerative disorders, all types of syndromes related pressure, all types of addiction (especially psychoactive substance use, abuse, seeking and reinstatement), all types of cognitive dysfunction in health populations and psychiatric patients or nervous system patients, all types of eating or drinking disorder, and the like.

In one embodiment, the disease related to orexin receptors comprises sleep disorders, depression, anxiety, panic disorders, obsessive-compulsive disorders, affective disorders, depressive neurosis, anxiety neurosis, mood disorders, panic attack disorders, behavior disorders, emotional disturbance, post-traumatic stress disorders, sexual dysfunction, psychosis, schizophrenia, manic depression, mental disorders, dementia, drug dependence, addiction, cognitive disorders, Alzheimer's disease, Parkinson's disease, movement disorders, eating disorders, headache, migraine, pain, digestive system disease, epilepsy, inflammation, cardiovascular disease, diabetes, metabolic disease, immunity-related diseases, endocrine-related diseases or high blood pressure.

In one embodiment, the disease related to orexin receptors is selective from sleep disorders, which comprises all types of anhypnia, narcolepsy and other excessive sleepiness, parasomnia, sleep-related myodystonia, restless leg syndrome, sleep apnea syndrome, circadian rhythm disorders, jet lag syndrome, shift work syndrome, agrypnia related to delayed or advanced sleep phase syndrome or mental disease, and the like.

In one embodiment, the disease related to orexin receptors is selectable from psychiatry, neurology and neurodegenerative disorders, which comprises depression, anxiety disorders, panic disorders, obsessive-compulsive disorders, affective disorders, depressive neurosis, anxiety neurosis, mood disorders, panic attack disorders, post-traumatic stress disorders, sexual dysfunction, psychosis, Parkinson's disease, dementia or mental retardation, and the like.

In some embodiment, the disease related to orexin receptors is selectable from cognitive dysfunction, which comprises all types of instant or chronic attention, learning and memory function decline in normal, health, young, adult or old population, or all types of instant or chronic attention, learning and memory function decline in patients of psychosis, neurosis, cardiovascular and immune system diseases, and the like.

It should be understood that any of above symptoms or diseases is promoted or accelerated under certain environmental conditions such as pressure or fear (wherein, pressure may be generated from social sources such as social pressure or physical sources such as physical pressure, which comprises pressure generated by fear), and compounds disclosed herein particularly useful in the treatment of symptoms and diseases adjusted by these environmental conditions.

Besides being useful for human treatment, the compounds of the present invention and the compositions thereof are also useful for veterinary treatment of animals such as companion animals, exotic animals and mammals of farm animals. In other embodiments, the animals disclosed herein include horses, dogs, and cats. As used herein, the compounds disclosed herein include the pharmaceutically acceptable derivatives thereof.

General Synthetic Procedures

The invention is described by the following examples. But it is to be understood that the invention is not limited to those embodiments thereof, the examples are meant only to suggest a method of practicing the present invention.

Generally, the compounds disclosed herein may be prepared by methods described herein, wherein the substituents are as defined for Formula (I) to (IV), except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Tianjin Fuchen Reagent Chemical Factory, Wuhan XinHuaYuan Technology Development Co., Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Glassware was oven dried and/or heat dried.

Column chromatography was conducted using a silica gel column. Silica gel (300-400 mesh) was purchased from Qingdao Ocean Chemical Factory.

$^1$H NMR spectra were recorded using a Bruker 400 MHz or 600 MHz spectrometer. 1H NMR spectra were obtained by using $CDCl_3$, DMSO-$d_6$, $CD_3OD$ or acetone-$d_6$ as solvents (reported in ppm), and TMS (0 ppm) or chloroform (7.26 ppm) as the reference standard. When peak multiplicities were reported, the following abbreviations were used: s (singlet), d (doublet), t (triplet), m (multiplet), br (broadened), dd (doublet of doublets), and dt (doublet of triplets). Coupling constants, when given, were reported in Hertz (Hz).

Low-resolution mass spectral (MS) data were determined on an Agilent 6120 Quadrupole HPLC-MS spectrometer equipped with an Agilent Zorbax SB-$C_{18}$ (2.1×30 mm, 3.5 μm). The flow rate was 0.6 mL/min. The mobile phases consisted of a combination of A (0.1% formic acid in $CH_3CN$) and B (0.1% formic acid in $H_2O$) in gradient mode (5% to 95%), and an ESI source was used, the peak of HPLC was recorded with UV-Vis detection at 210/254 nm.

Purification of compound was detected on Agilent 1260 pre-HPLC or Calesep pump 250 pre-HPLC with UV at 210 nm/254 nm (NOVASEP, 50/80 mm DAC).

The following abbreviations are used throughout the specification:

Boc tert-butoxycarbonyl
$CH_2Cl_2$, DCM dichloromethane
$Cs_2CO_3$ cesium carbonate
$CDCl_3$ chloroform-d
CuI cuprous iodide
DMF N,N-dimethylformamide
DMSO dimethylsulfoxide
$Et_3N$, TEA triethylamine
EtOAc, EA ethyl acetate
EtOH ethyl alcohol
g gram
h hour, hours
KOH potassium hydroxide
$K_2CO_3$ potassium carbonate
MeCN, $CH_3CN$ acetonitrile
$Na_2CO_3$ sodium carbonate
NaOH sodium hydroxide
$Na_2SO_4$ sodium sulfate
$MgSO_4$ magnesium sulfate
mL, ml milliliter
PE petroleum ether (60-90° C.)
RT, rt, r.t. room temperature The following Schemes describe the procedures for preparation of compounds of the present invention. Unless defined otherwise, $R^1$, $R^2$, $R^3$, $R^4$, $R^5$, $R^6$, $R^7$ and $R^8$ are as defined herein.

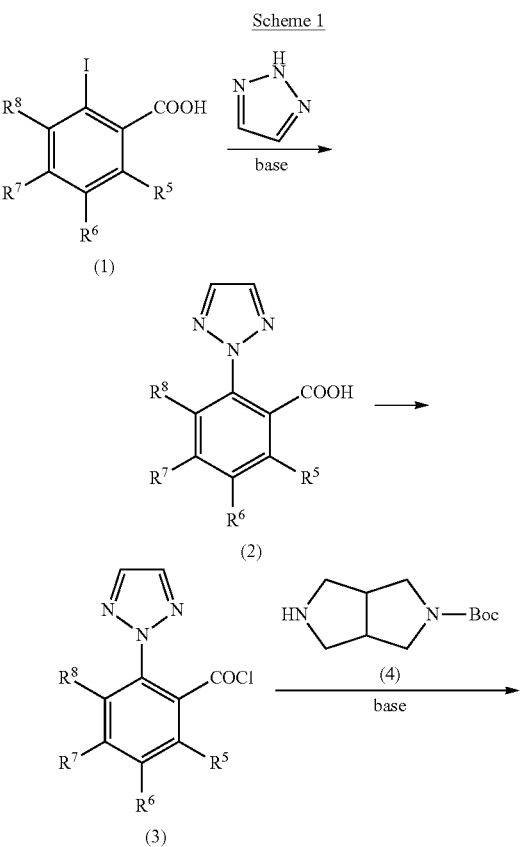

Scheme 1

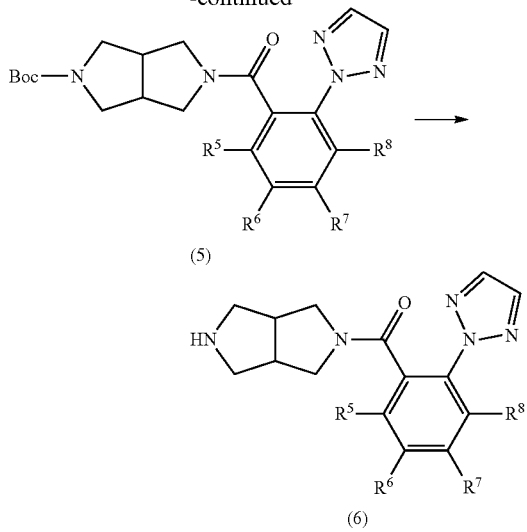

First, optionally substituted o-iodobenzoic acid (1) can react with 2H-1,2,3-triazole catalyzed by a catalyst (such as CuI) in the presence of a suitable base under a heating condition to give compound (2), compound (2) can react with a chlorinating agent under a heating condition to give compound (3), and then compound (3) can react with 2-Boc-hexahydropyrrolo[3,4-c]pyrrole (4) in the presence of a suitable base to give compound (5), and the Boc protecting group of compound (5) can be removed under a suitable condition (such as in the presence of an acid or under a heating condition) to give a corresponding intermediate compound (6).

Optionally substituted o-aminophenol (7) can react with potassium ethylxanthate through cyclization and acidification to give compound (8), which can react with a chlorinating agent under a heating condition to give compound (9), and finally compound (9) can be condensed with the above intermediate compound (6) to give the title compound (10).

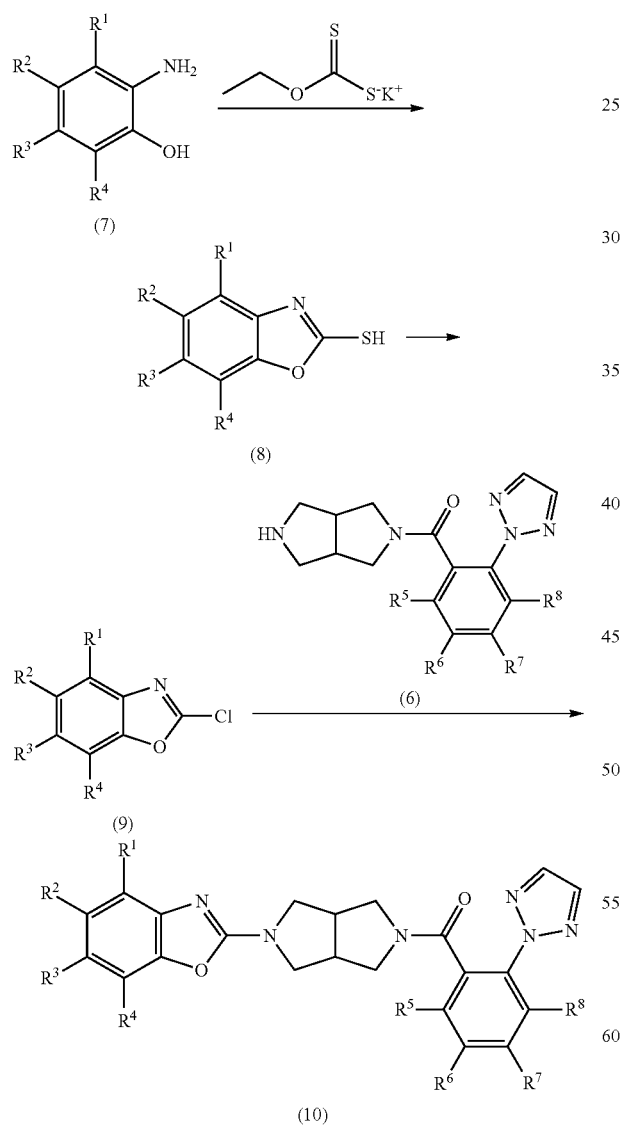

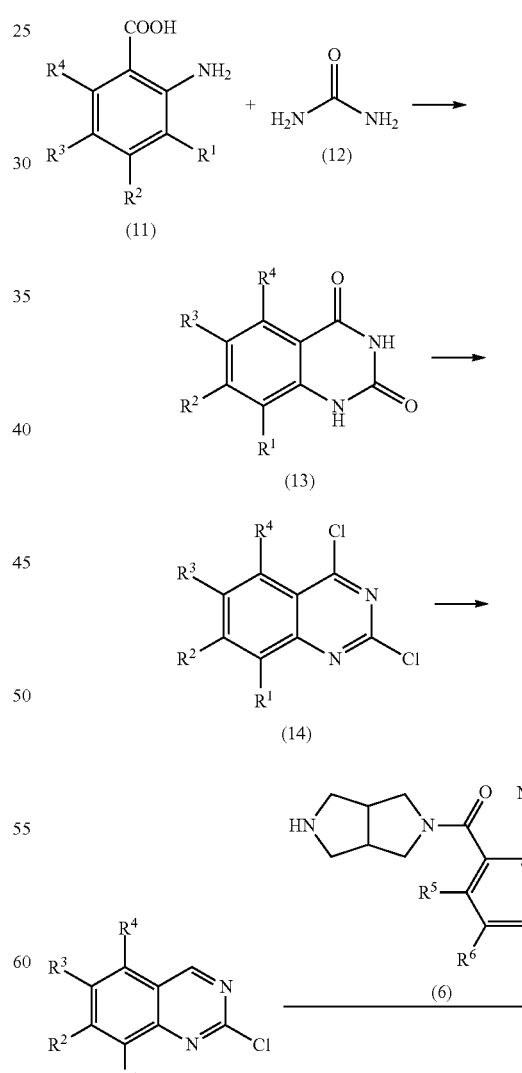

Compounds (10) of the present invention can be prepared by the general synthetic procedure illustrated in Scheme 1, and the details are described in the specific examples:

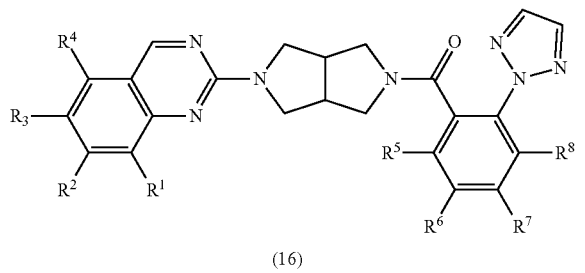

(16)

Compound (16) disclosed herein can prepared by the general synthetic procedure illustrated in Scheme 2, and the details are described in the specific examples:

First, optionally substituted o-aminobenzoic acid (11) can react with urea (12), through cyclization under a heating condition to give compound (13), which can react with a chlorinating agent under a heating condition to give 2,4-dichloroquinazoline compound (14), then compound (14) can react to give compound (15) under a suitable condition, and finally compound (15) can be condensed with the intermediate compound (6) to give the title compound (16).

Scheme 3

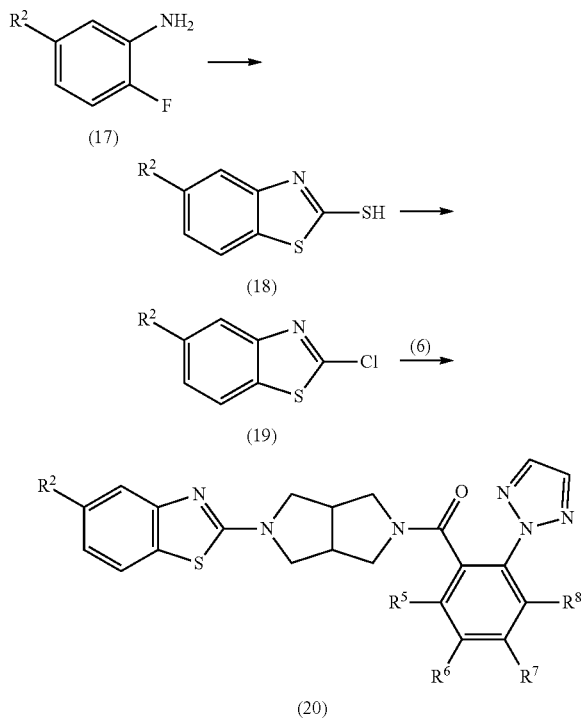

Compound (20) disclosed herein can prepared by the general synthetic procedure illustrated in Scheme 3, and the details are described in the specific examples: optionally substituted 2-fluoroaniline (17) and potassium ethylxanthate can react through cyclization and acidification to obtain compound (18), and then compound (18) can react with chlorinated reagent under a heating condition to get compound (19), at last, compound (19) can condense with intermediate (6) to obtain the target compound (20).

Scheme 4

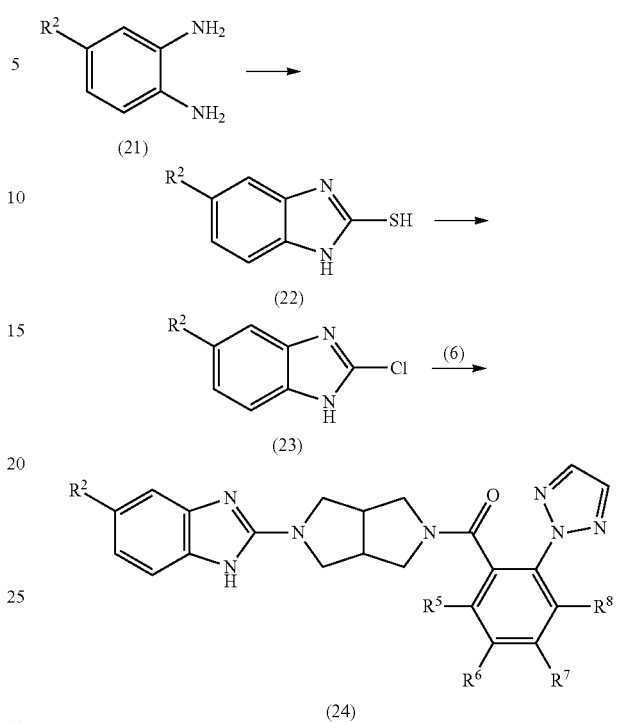

Compound (24) disclosed herein can prepared by the general synthetic procedure illustrated in Scheme 4, and the details are described in the specific examples: optionally substituted o-phenylenediamine (21) and N,N'-carbonyldiimidazole can react through cyclization and acidification to obtain compound (22), and then compound (22) can react with chlorinated reagent under a heating condition to get compound (23), at last, compound (23) can condense with intermediate (6) to obtain the target compound (24).

Scheme 5

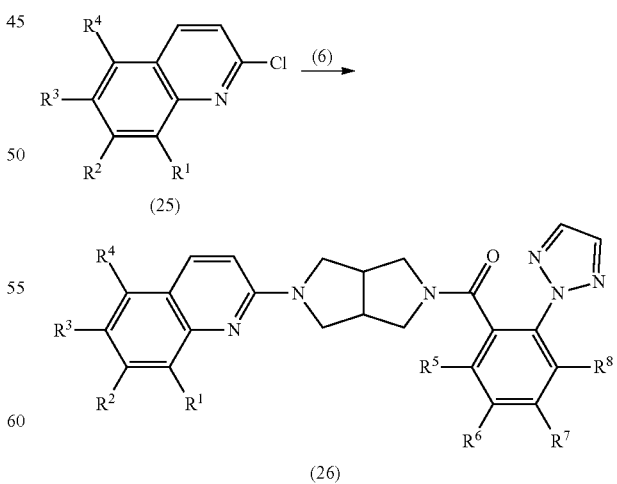

Compound (26) disclosed herein can prepared by the general synthetic procedure illustrated in Scheme 5, and the details are described in the specific examples: chloroquinoline (25) with various substituents can condense with compound (6) to obtain the target compound (26).

Compounds and pharmaceutical compositions provided herein and the application thereof are further illustrated through examples.

EXAMPLE

Example 1

(5-(5-chlorobenzo[d]oxazol-2-yl)hexahydropyrrolo[3,4-c]pyrrol-2(1H)-yl)(5-methyl-2-(2H-1,2,3-triazol-2-yl)phenyl)methanone

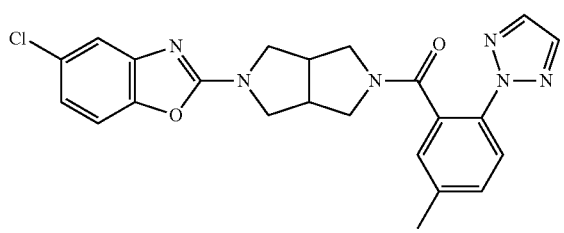 [SMILES: Cc1ccc(-n2nccn2)c(C(=O)N2CC3CN(c4nc5cc(Cl)ccc5o4)CC3C2)c1]

Step 1) Synthesis of 5-methyl-2-(2H-1,2,3-triazol-2-yl)benzoic Acid

To a solution of N,N-dimethylformamide (30 mL) were added sequentially 2H-1,2,3-triazole (3.45 g, 50 mmol), 2-iodo-5-methyl benzoic acid (5.24 g, 20 mmol), cesium carbonate (11.72 g, 36 mmol), trans-N,N'-dimethyl-1,2-cyclohexanediamine (0.51 g, 3.6 mmol) and cuprous iodide (0.38 g, 2 mmol). The reaction was heated to 100° C. under $N_2$. After reaction for 4 hours, the reaction mixture was cooled to rt, diluted with water (60 mL) and extracted with ethyl acetate (200 mL×2). The aqueous layer was acidified to pH 1 to 2 with concentrated hydrochloric acid, and then extracted with ethyl acetate (200 mL×2). The combined organic layers were dried over anhydrous sodium sulfate, and filtered. The filtrate was concentrated in vacuo and the residue was purified by silica gel column chromatography (DCM/methanol (v/v)=50/1) to give the title compound as a yellow solid (2.76 g, 68%).

MS (ESI, neg. ion) m/z: 202.1 [M−H]$^-$;
$^1$H NMR (CD$_3$OD, 600 MHz) δ (ppm): 7.88 (s, 2H), 7.66 (d, 1H), 7.59 (d, J=8.2 Hz, 1H), 7.50-7.48 (dd, J=8.1 Hz, 1.1 Hz, 1H), 2.45 (s, 3H); and
$^{13}$C NMR (CD$_3$OD, 151 MHz) δ (ppm): 169.8, 140.7, 137.5, 136.7, 133.5, 131.5, 129.3, 126.0, 21.0.

Step 2) Synthesis of 5-methyl-2-(2H-1,2,3-triazol-2-yl)benzoyl Chloride

To a solution of 5-methyl-2-(2H-1,2,3-triazol-2-yl)benzoic acid (2.03 g, 10 mmol) in anhydrous DCM (20 mL) were added sulfoxide chloride (15 mL, 206 mmol) and pyridine (0.15 mL, 2 mmol) slowly. The reaction was heated to reflux for 3 hours, and then cooled. The solvent was removed in vacuo to give a product, which was used directly in the next step.

Step 3) Synthesis of 5-(5-methyl-2-(2H-1,2,3-triazol-2-yl)benzoyl)hexahydropyrrolo[3,4-c]pyrrol-2(1H)-tert-butyl Formate To a solution of 2-Boc-hexahydropyrrolo[3,4-c]pyrrole (0.99 g, 4.66 mmol) in anhydrous DCM (20 mL) were added slowly triethylamine (5.0 mL, 36 mmol) and a solution of 5-methyl-2-(2H-1,2,3-triazol-2-yl)benzoyl chloride (1.25 g, 5.64 mmol) in DCM (15 mL) in an ice-water bath. The reaction mixture was stirred for 10 min in the ice-water bath, and then the mixture was reacted at rt for 12 hours. To the reaction was added DCM (50 mL), and then washed with water (50 mL) and saturated aqueous NaCl solution (50 mL) successively. The organic layer was dried over sodium sulfate, filtered, and the filtrate was concentrated in vacuo, the residue was purified by silica gel chromatography (PE/EtOAc (v/v)=1/1.2) to give the title compound as yellow thick oil (1.79 g, 96.7%).

MS (ESI, pos. ion) m/z: 398.1 [M+H]$^+$; and
$^1$H NMR (CDCl$_3$, 600 MHz) δ (ppm): 7.84 (d, J=7.4 Hz, 1H), 7.77 (s, 2H), 7.30 (d, J=8.0 Hz, 1H), 7.20 (s, 1H), 3.78-3.76 (m, 1H), 3.64-3.53 (m, 2H), 3.45-3.38 (m, 1H), 3.27-3.25 (m, 2H), 3.16-3.07 (m, 1H), 2.93-2.87 (m, 2H), 2.76 (s, 1H), 2.39 (s, 3H), 1.45 (s, 9H).

Step 4) Synthesis of hexahydropyrrolo[3,4-c]pyrrol-2(1H)-yl)(5-methyl-2-(2H-1,2,3-triazol-2-yl) phenyl)methanone To a solution of 5-(5-methyl-2-(2H-1,2,3-triazol-2-yl)benzoyl)hexahydropyrrolo[3,4-c]pyrrol-2(1H)-tert-butyl formate (1.79 g, 4.5 mmol) in anhydrous DCM (15 mL) was added a solution of hydrogen chloride in ethyl acetate (15 mL, 3 M). The reaction was reacted at rt for 1 hour, then water (30 mL) and potassium carbonate (0.83 g, 6.0 mmol) were added slowly. The resulting mixture was stirred for 0.5 hour, then concentrated in vacuo, the thick oil was purified by silica gel column chromatography (DCM/Methanol (v/v)=10/1) to give the title compound as a yellow oil (1.28 g, 95.6%).

MS (ESI, pos. ion) m/z: 298.4 [M+H]$^+$; and
$^1$H NMR (CDCl$_3$, 600 MHz) δ (ppm): 7.81-7.79 (m, 3H), 7.30 (d, J=7.9 Hz, 1H), 7.17 (s, 1H), 3.72-3.64 (m, 2H), 3.37 (s, 1H), 3.35-3.31 (m, 1H), 3.21-3.18 (m, 1H), 3.09-3.06 (m, 1H), 2.97-2.95 (m, 2H), 2.85-2.77 (m, 2H), 2.38 (s, 3H).

Step 5) Synthesis of 5-chlorobenzo[d]oxazole-2-thiol

To ethanol (100 mL) were added sequentially 2-amino-4-chlorophenol (6.02 g, 41.94 mmol) and ethyl potassium xanthate (7.07 g, 44.09 mmol), the reaction was heated gradually to reflux and stirred for 7 hours, and then concentrated in vacuo. The thick oil was dissolved in water (150 mL), and extracted with ethyl acetate (100 mL). The aqueous layer was adjusted to pH 4 to 5 with aqueous hydrochloric acid solution (1 M), and white solid precipitated out. Filtered under vacuum, the solid was dried to give the title compound as a white solid (7.02 g, 90.2%).

MS (ESI, pos. ion) m/z: 186.1 [M+H]$^+$; and
$^1$H NMR (DMSO-d$_6$, 600 MHz) δ (ppm): 13.99 (s, 1H), 7.52 (d, J=8.2 Hz, 1H), 7.31-7.28 (m, 2H)

Step 6) Synthesis of 2,5-dichlorobenzo[d]oxazole

A mixture of 5-chlorobenzo[d]oxazole-2-thiol (3.01 g, 16.22 mmol), sulfoxide chloride (20 mL, 272.6 mmol) and N,N-dimethylformamide (0.10 mL, 1.3 mmol) was heated to reflux and stirred for 3 hours The reaction mixture was cooled and the solvent was removed in vacuo. The resulting product was used directly in the next step.

Step 7) Synthesis of (5-(5-chlorobenzo[d]oxazol-2-yl)hexahydropyrrolo[3,4-c]pyrrol-2(1H)-yl)(5-methyl-2-(2H-1,2,3-triazol-2-yl)phenyl)methanone To acetonitrile (40 mL) were added (2,5-chlorobenzo[d]oxazole (0.62 g, 3.30 mmol), (hexahydropyrrolo[3,4-c]pyrrol-2(1H)-yl)(5-methyl-2-(2H-1,2,3-triazol-2-yl)phenyl)methanone (0.65 g, 2.20 mmol) and potassium carbonate (1.54 g, 11.03 mmol). The reaction was heated to reflux and stirred for 10 hours under $N_2$, and then cooled and the solvent was removed in vacuo. The resulting thick oil was dissolved in DCM (30 mL), and extracted sequentially with water (30 mL) and saturated aqueous NaCl solution (30 mL). The organic layer was dried over sodium sulfate, filtered, and the filtrate was concentrated in vacuo, the residue was purified by silica gel chromatography (PE/EtOAc (v/v)=1/2) to give the title compound as a yellow solid (0.498 g, 50.36%).

MS (ESI, pos. ion) m/z: 449.2 [M+H]$^+$; and $^1$H NMR (DMSO-d$_6$, 400 MHz) δ (ppm): 7.97 (s, 2H), 7.75 (d, J=8.3 Hz, 1H), 7.42 (t, J=9.1 Hz, 2H), 7.33 (d, J=11.0 Hz, 2H), 7.02 (d, J=8.4 Hz, 1H), 3.92-3.79 (m, 1H), 3.76-3.60 (m, 2H), 3.58-3.39 (m, 4H), 3.04 (d, J=30.9 Hz, 3H), 2.38 (s, 3H).

Example 2

(2-(2H-1,2,3-triazol-2-yl)phenyl)(5-(5-chlorobenzo[d]oxazol-2-yl) hexahydropyrrolo[3,4-c]pyrrol-2(1H)-yl)methanone

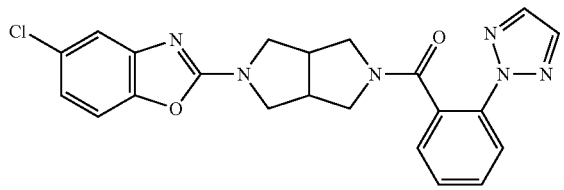 [SMILES: O=C(c1ccccc1-n1nccn1)N1CC2CN(c3nc4cc(Cl)ccc4o3)CC2C1]

Step 1) Synthesis of 2-(2H-1,2,3-triazol-2-yl)benzoic Acid 2H-1,2,3-Triazole (0.7 g, 10.08 mmol) was reacted with 2-iodobenzoic acid (1 g, 4.03 mmol), cesium carbonate (2.36 g, 7.2 mmol), trans-N,N'-dimethyl-1,2-hexanediamine (0.103 g, 0.752 mmol) and cuprous iodide (0.077 g, 0.403 mmol) in N,N-dimethyl formamide (18 mL) according to the procedure as described in step 1 of example 1, and the crude product was purified by silica gel chromatography (DCM/Methanol (v/v)=30/1) to give the title compound as a yellow solid (0.511 g, 67%).

MS (ESI, neg. ion) m/z: 188.1 [M−H]$^-$;

$^1$H NMR (DMSO-d$_6$, 600 MHz) δ (ppm): 13.06 (s 1H), 8.08 (s, 2H), 7.78-7.75 (m, 2H), 7.72-7.68 (m, 1H), 7.60-7.57 (m, 1H); and $^{13}$C NMR (DMSO-d$_6$, 151 MHz) δ (ppm): 167.7, 137.5, 136.3, 131.7, 129.6, 128.9, 128.5, 124.4.

Step 2) Synthesis of 2-(2H-1,2,3-triazol-2-yl)benzoyl Chloride

To a solution of 2-(2H-1,2,3-triazol-2-yl)benzoic acid (0.37 g, 1.96 mmol) in anhydrous DCM (20 mL) were added slowly sulfoxide chloride (6 mL, 82.7 mmol) and pyridine (0.04 mL, 0.5 mmol). The reaction was heated to reflux and stirred for 3 hours, and then cooled and the solvent was removed in vacuo to give a product, which was used directly in the next step.

Step 3) Synthesis of 5-(2-(2H-1,2,3-triazol-2-yl)benzoyl)hexahydropyrrolo[3,4-c]pyrrol-2(1H)-tert-butyl Formate 2-(2H-1,2,3-Triazol-2-yl)benzoyl chloride (1.12 g, 5.39 mmol) was reacted with 2-Boc-hexahydropyrrol[3,4-c]pyrrole (0.96 g, 4.52 mmol) and triethylamine (2.55 mL, 18.1 mmol) in anhydrous DCM (30 mL) according to the procedure as described in step 3 of example 1, and the crude product was purified by silica gel chromatography (PE/EtOAc (v/v)=1/1) to give the title compound as orange-yellow thick oil (1.33 g, 76.6%).

MS (ESI, pos. ion) m/z: 384.3 [M+H]$^+$; and $^1$H NMR (CDCl$_3$, 400 MHz) δ (ppm): 8.00 (d, J=8.1 Hz, 1H), 7.81 (s, 2H), 7.55-7.50 (m, 1H), 7.45-7.42 (m, 2H), 3.83-3.79 (m, 1H), 3.64-3.56 (m, 2H), 3.48-3.39 (m, 1H), 3.36-3.27 (m, 2H), 3.20-3.13 (m, 1H), 2.98-2.90 (m, 2H), 2.82-2.78 (m, 1H), 1.46 (s, 9H).

Step 4) Synthesis of (2-(2H-1,2,3-triazol-2-yl)phenyl)hexahydropyrrolo[3,4-c]pyrrol-2(1H)-yl) methanone 5-(2-(2H-1,2,3-Triazol-2-yl)benzoyl)hexahydropyrrol[3,4-c]pyrrole-2(1H)-tert-butyl formate (1.31 g, 3.42 mmol) was reacted with a solution of hydrogen chloride in ethyl acetate (10 mL, 35 mmol) in anhydrous DCM (20 mL) according to the procedure as described in step 4 of example 1, and the crude product was purified by silica gel chromatography (DCM/Methanol (v/v)=15/1) to give the title compound as orange-yellow thick oil (0.94 g, 97.1%).

MS (ESI, pos. ion) m/z: 284.2 [M+H]$^+$; and $^1$H NMR (CDCl$_3$, 400 MHz) δ (ppm): 7.97 (d, J=8.1 Hz, 1H), 7.83 (s, 2H), 7.54-7.50 (m, 1H), 7.44-7.38 (m, 2H), 3.79-3.67 (m, 2H), 3.31-3.26 (m, 2H), 3.15 (dd, J=11.2 Hz, 7.3 Hz, 1H), 3.08 (dd, J=11.4 Hz, 3.4 Hz, 1H), 2.95 (d, J=8.4 Hz, 2H), 2.83-2.75 (m, 2H).

Step 5) Synthesis of (2-(2H-1,2,3-triazol-2-yl)phenyl)(5-(5-chlorobenzo[d]oxazol-2-yl) hexahydropyrrolo[3,4-c]pyrrol-2(1H)-yl)methanone 2,5-Dichlorobenzo[d]oxazole (0.31 g, 1.65 mmol) was reacted with (2-(2H-1,2,3-triazol-2-yl)phenyl)(hexahydropyrrolo[3,4-c]pyrrol-2(1H)-yl)methanone (0.31 g, 1.10 mmol) and potassium carbonate (0.76 g, 5.50 mmol) in acetonitrile (20 mL) according to the procedure as described in step 7 of example 1, and the crude product was purified by silica gel chromatography (PE/EtOAc (v/v)=1/3) to give the title compound as a pale yellow solid (0.255 g, 53.2%).

MS (ESI, pos. ion) m/z: 435.5 [M+H]$^+$; and $^1$H NMR (CDCl$_3$, 400 MHz) δ (ppm): 7.96 (d, J=8.1 Hz, 1H), 7.72 (s, 2H), 7.53-7.49 (m, 1H), 7.43-7.36 (m, 2H), 7.30 (d, J=1.9 Hz, 1H), 7.14 (d, J=8.4 Hz, 1H), 6.97 (dd, J=8.4 Hz, 2.0 Hz, 1H), 3.93-3.84 (m, 2H), 3.77-3.70 (m, 2H), 3.64-3.57 (m, 1H), 3.52-3.44 (m, 2H), 3.12-2.99 (m, 3H).

Example 3

(5-(5-chlorobenzo[d]oxazol-2-yl)hexahydropyrrolo[3,4-c]pyrrol-2(1H)-yl)(2-fluoro-6-(2H-1,2,3-triazol-2-yl)phenyl)methanone

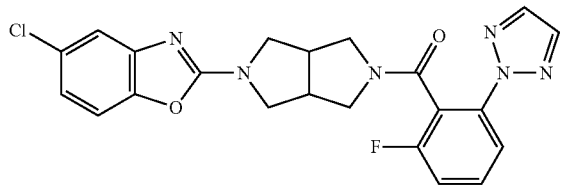 [SMILES: O=C(c1c(F)cccc1-n1nccn1)N1CC2CN(c3nc4cc(Cl)ccc4o3)CC2C1]

Step 1) Synthesis of 2-fluoro-6-(2H-1,2,3-triazol-2-yl)benzoic Acid 2H-1,2,3-Triazole (1.947 g, 28.19 mmol) was reacted with 2-fluoro-6-iodobenzoic acid (3 g, 11.28 mmol), cesium carbonate (6.616 g, 20.31 mmol), trans-N,N'-dimethyl-1,2-hexanediamine (0.289 g, 2.03 mmol) and cuprous iodide (0.215 g, 1.13 mmol) in N,N-dimethyl formamide (12 mL) according to the procedure as described in step 1 of example 1, and the crude product was purified by silica gel chromatography (DCM/Methanol (v/v)=100/1) to give the title compound as a yellow solid (1.503 g, 64.33%).

MS (ESI, pos. ion) m/z: 208.2 [M+H]$^+$; and $^1$H NMR (DMSO-d$_6$, 600 MHz) δ (ppm): 8.15 (s, 2H), 7.79 (d, J=8.22 Hz, 1H), 7.70-7.65 (m, 1H), 7.44 (t, J=8.75 Hz, 1H).

Step 2) Synthesis of 2-fluoro-6-(2H-1,2,3-triazol-2-yl)benzoyl Chloride

To a solution of 2-fluoro-6-(2H-1,2,3-triazol-2-yl)benzoic acid (1.026 g, 4.953 mmol) in anhydrous DCM (20 mL) were added slowly sulfoxide chloride (11 mL, 150 mmol) and pyridine (0.08 mL, 1 mmol). The reaction was heated to reflux and stirred for 3 hours, and then cooled and the solvent was removed in vacuo to give a product, which was used directly in the next step.

Step 3) Synthesis of 5-(2-fluoro-6-(2H-1,2,3-triazol-2-yl)benzoyl)hexahydropyrrolo[3,4-c]pyrrol-2(1H)-tert-butyl Formate 2-Fluoro-6-(2H-1,2,3-triazol-2-yl)benzoyl chloride (1.11 g, 4.92 mmol) was reacted with 2-Boc-hexahydropyrrol[3,4-c]pyrrole (0.87 g, 4.10 mmol) and triethylamine (2.35 mL, 16.7 mmol) in anhydrous DCM (30 mL) according to the procedure as described in step 3 of example 1, and the crude product was purified by silica gel chromatography (PE/EtOAc (v/v)=1/1) to give the title compound as orange-yellow thick oil (1.45 g, 88.15%).

MS (ESI, pos. ion) m/z: 346.3 [M+H-56]$^+$; and $^1$H NMR (CDCl$_3$, 400 MHz) δ (ppm): 7.84-7.78 (m, 3H), 7.50-7.44 (m, 1H), 7.13 (td, J=8.4 Hz, 2.7 Hz, 1H), 3.86-3.64 (m, 3H), 3.58-3.54 (m, 1H), 3.51-3.47 (m, 1H), 3.40-3.37 (m, 1H), 3.32-3.15 (m, 2H), 2.95-2.82 (m, 2H), 1.45 (s, 9H).

Step 4) Synthesis of (2-fluoro-6-(2H-1,2,3-triazol-2-yl)phenyl)hexahydropyrrolo[3,4-c]pyrrol-2(1H)-yl)methanone 5-(2-Fluoro-6-(2H-1,2,3-triazol-2-yl)benzoyl)hexahydropyrrol[3,4-c]pyrrole-2(1H)-tert-butyl formate (1.41 g, 3.51 mmol) was reacted with a solution of hydrogen chloride in ethyl acetate (10 mL, 35 mmol) in anhydrous DCM (10 mL) according to the procedure as described in step 4 of example 1, and the crude product was purified by silica gel chromatography (DCM/Methanol (v/v)=20/1) to give the title compound as yellow thick oil (0.977 g, 92.27%).

MS (ESI, pos. ion) m/z: 302.4 [M+H]$^+$; and $^1$H NMR (CDCl$_3$, 400 MHz) δ (ppm): 7.87-7.79 (m, 3H), 7.51-7.45 (m, 1H), 7.15 (t, J=8.4 Hz, 1H), 3.77-3.59 (m, 3H), 3.25-3.08 (m, 3H), 3.03-2.91 (m, 2H), 2.90-2.74 (m, 2H).

Step 5) Synthesis of (5-(5-chlorobenzo[d]oxazol-2-yl)hexahydropyrrolo[3,4-c]pyrrol-2(1H)-yl)(2-fluoro-6-(2H-1,2,3-triazol-2-yl)phenyl)methanone 2,5-Dichlorobenzo[d]oxazole (0.226 g, 1.202 mmol) was reacted with (2-fluoro-6-(2H-1,2,3-triazol-2-yl)phenyl)([3,4-c]pyrrol-2(1H)-yl)methanone (0.241 g, 0.8 mmol) and potassium carbonate (0.55 g, 4.0 mmol) in acetonitrile (20 mL) according to the procedure as described in step 7 of example 1, and the crude product was purified by silica gel chromatography (PE/EtOAc (v/v)=1/2) to give the title compound as a pale yellow solid (0.279 g, 77.13%).

MS (ESI, pos. ion) m/z: 453.3 [M+H]$^+$; and $^1$H NMR (CDCl$_3$, 600 MHz) δ (ppm): 7.86-7.73 (m, 3H), 7.49-7.46 (m, 1H), 7.31 (s, 1H), 7.16-7.12 (m, 2H), 6.98 (d, J=8.3 Hz, 1H), 4.00-3.78 (m, 4H), 3.75-3.72 (m, 1H), 3.70-3.61 (m, 2H), 3.31-3.26 (m, 1H), 3.18-3.07 (m, 2H).

Example 4

(5-(5-fluorobenzo[d]oxazol-2-yl)hexahydropyrrolo[3,4-c]pyrrol-2(1H)-yl)(5-methyl-2-(2H-1,2,3-triazol-2-yl)phenyl)methanone

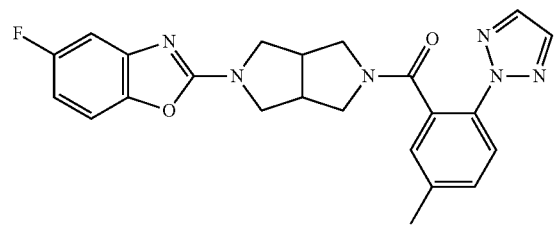 [SMILES: Cc1ccc(-n2nccn2)c(C(=O)N2CC3CN(c4nc5cc(F)ccc5o4)CC3C2)c1]

Step 1) Synthesis of 5-fluorobenzo[d]oxazole-2-thiol

2-Amino-4-fluorophenol (5.085 g, 40.0 mmol) was reacted with ethyl potassium xanthate (6.733 g, 42.0 mmol) in ethanol (100 mL) according to the procedure as described in step 5 of example 1 to give the title compound as a white solid (6.165 g, 91.1%).

MS (ESI, pos. ion) m/z: 170.1 [M+H]$^+$; and $^1$H NMR (DMSO-d$_6$, 600 MHz) δ (ppm): 13.96 (s, 1H), 7.53 (dd, J=8.9 Hz, 4.2 Hz, 1H), 7.13 (dd, J=8.1 Hz, 2.6 Hz, 1H), 7.10 (ddd, J=9.9 Hz, 9.0 Hz, 2.6 Hz, 1H).

Step 2) Synthesis of 2-chloro-5-fluorobenzo[d]oxazole

A mixture of 5-fluorobenzo[d]oxazole-2-thiol (2.538 g, 15.0 mmol), sulfoxide chloride (20 mL, 272.6 mmol) and N,N-dimethylformamide (0.05 mL, 0.65 mmol) was heated to reflux and stirred for 3 hours, and then cooled, and the solvent was removed in vacuo. The resulting product was used directly in the next step.

Step 3) Synthesis of (5-(5-fluorobenzo[d]oxazol-2-yl)hexahydropyrrolo[3,4-c]pyrrol-2(1H)-yl)(5-methyl-2-(2H-1,2,3-triazol-2-yl)phenyl)methanone 2-Chloro-5-fluorobenzo[d]oxazole (0.257 g, 1.5 mmol) was reacted with (hexahydropyrrolo[3,4-c]pyrrol-2(1H)-yl)(5-methyl-2-(2H-1,2,3-triazol-2-yl)phenyl)methanone (0.297 g, 1.0 mmol) and potassium carbonate (0.69 g, 5.0 mmol) in acetonitrile (20 mL) according to the procedure as described in step 7 of example 1, and the crude product was purified by silica gel chromatography (PE/EtOAc (v/v)=1/2) to give the title compound as a pale yellow solid (0.280 g, 64.7%).

MS (ESI, pos. ion) m/z: 433.3 [M+H]$^+$; and $^1$H NMR (CDCl$_3$, 600 MHz) δ (ppm): 7.87 (dd, J=8.4 Hz, 4.0 Hz, 1H), 7.72 (s, 2H), 7.35-7.28 (m, 2H), 7.18 (s, 1H), 7.16-7.13 (m, 1H), 6.92-6.87 (m, 1H), 3.92-3.83 (m, 2H), 3.73-3.70 (m, 2H), 3.61-3.58 (m, 1H), 3.51-3.48 (m, 1H), 3.46-3.41 (m, 1H), 3.14-3.09 (m, 1H), 3.03-2.98 (m, 2H), 2.38 (s, 3H).

Example 5

(2-(2H-1,2,3-triazol-2-yl)phenyl)(5-(5-fluorobenzo[d]oxazol-2-yl) hexahydropyrrolo[3,4-c]pyrrol-2(1H)-yl)methanone

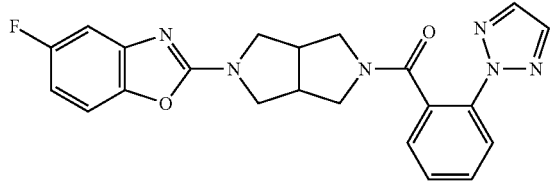 [SMILES: O=C(c1ccccc1-n1nccn1)N1CC2CN(c3nc4cc(F)ccc4o3)CC2C1]

2-Chloro-5-fluorobenzo[d]oxazole (0.257 g, 1.5 mmol) was reacted with (2-(2H-1,2,3-triazol-2-yl)phenyl)(hexahydropyrrolo[3,4-c]pyrrol-2(1H)-yl)methanone (0.283 g, 1.0 mmol) and potassium carbonate (0.69 g, 5.0 mmol) in acetonitrile (20 mL) according to the procedure as described in step 7 of example 1, and the crude product was purified by silica gel chromatography (PE/EtOAc (v/v)=1/3) to give the title compound as a pale yellow solid (0.264 g, 63.2%).

MS (ESI, pos. ion) m/z: 419.3 [M+H]$^+$; and $^1$H NMR (CDCl$_3$, 400 MHz) δ (ppm): 7.90 (dd, J=8.1 Hz, 4.2 Hz, 1H), 7.71 (s, 2H), 7.41-7.38 (m, 1H), 7.36-7.33 (m, 2H), 7.28 (d, J=2.0 Hz, 1H), 7.16 (d, J=8.2 Hz, 1H), 6.94 (dd, J=8.2 Hz, 2.0 Hz, 1H), 3.95-3.86 (m, 2H), 3.76-3.69 (m, 2H), 3.65-3.59 (m, 1H), 3.54-3.47 (m, 2H), 3.10-2.97 (m, 3H).

Example 6

(2-fluoro-6-(2H-1,2,3-triazol-2-yl)phenyl)(5-(5-fluorobenzo[d]oxazol-2-yl) hexahydropyrrolo[3,4-c]pyrrol-2(1H)-yl)methanone

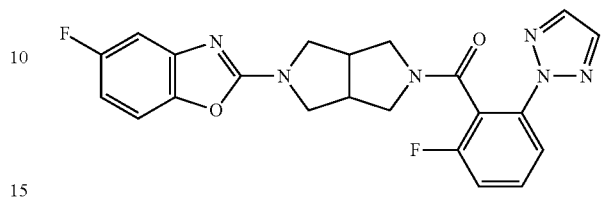

2-Chloro-5-fluorobenzo[d]oxazole (0.257 g, 1.5 mmol) was reacted with (2-fluoro-6-(2H-1,2,3-triazol-2-yl)phenyl)(hexahydropyrrolo[3,4-c]pyrrol-2(1H)-yl)methanone (0.301 g, 1.0 mmol) and potassium carbonate (0.69 g, 5.0 mmol) in acetonitrile (20 mL) according to the procedure as described in step 7 of example 1, and the crude product was purified by silica gel chromatography (PE/EtOAc (v/v)=1/2) to give the title compound as a yellow solid (0.259 g, 59.4%).

MS (ESI, pos. ion) m/z: 437.3 [M+H]$^+$; and $^1$H NMR (CDCl$_3$, 600 MHz) δ (ppm): 7.88-7.70 (m, 3H), 7.52-7.47 (m, 1H), 7.33-7.29 (m, 1H), 7.19-7.15 (m, 2H), 7.03-6.99 (m, 1H), 4.02-3.88 (m, 2H), 3.86-3.76 (m, 2H), 3.72-3.68 (m, 1H), 3.65-3.57 (m, 2H), 3.21-3.16 (m, 1H), 3.14-2.99 (m, 2H).

Example 7

(5-(5-methoxybenzo[d]oxazol-2-yl)hexahydropyrrolo[3,4-c]pyrrol-2(1H)-yl)(5-methyl-2-(2H-1,2,3-triazol-2-yl)phenyl)methanone

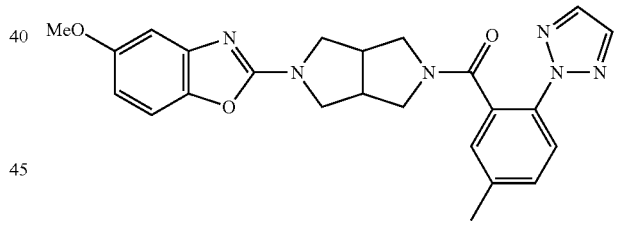

Step 1) Synthesis of 5-methoxybenzo[d]oxazole-2-thiol

2-Amino-4-methoxyphenol (5.566 g, 40.0 mmol) was reacted with ethyl potassium xanthate (6.733 g, 42.0 mmol) in ethanol (100 mL) according to the procedure as described in step 5 of example 1 to give the title compound as an off-white solid (6.487 g, 89.5%).

MS (ESI, pos. ion) m/z: 182.1 [M+H]$^+$; and $^1$H NMR (CDCl$_3$, 400 MHz) δ (ppm): 10.20 (s, 1H), 7.23 (d, J=8.9 Hz, 1H), 6.78 (dd, J=8.9 Hz, 2.4 Hz, 1H), 6.71 (d, J=2.4 Hz, 1H), 3.81 (s, 3H).

Step 2) Synthesis of 2-chloro-5-methoxybenzo[d]oxazole

A mixture of 5-methoxybenzo[d]oxazole-2-thiol (2.718 g, 15.0 mmol), sulfoxide chloride (20 mL, 272.6 mmol) and N,N-dimethylformamide (0.05 mL, 0.65 mmol) was heated gradually to reflux and stirred for 3 hours, and then cooled and the solvent was removed in vacuo. The resulting product was used directly in the next step.

Step 3) Synthesis of (5-(5-methoxybenzo[d]oxazol-2-yl)hexahydropyrrolo[3,4-c]pyrrol-2(1H)-yl)(5-methyl-2-(2H-1,2,3-triazol-2-yl)phenyl)methanone 2-Chloro-5-methoxybenzo[d]oxazole (0.275 g, 1.5 mmol) was reacted with (hexahydropyrrolo[3,4-c]pyrrol-2(1H)-yl)(5-methyl-2-(2H-1,2,3-triazol-2-yl)phenyl)methanone (0.297 g, 1.0 mmol) and potassium carbonate (0.69 g, 5.0 mmol) in acetonitrile (20 mL) according to the procedure as described in step 7 of example 1, and the crude product was purified by silica gel chromatography (PE/EtOAc (v/v)=1/3) to give the title compound as a pale yellow solid (0.303 g, 68.2%).

MS (ESI, pos. ion) m/z: 445.3 [M+H]$^+$; and $^1$H NMR (CDCl$_3$, 600 MHz) δ (ppm): 7.81 (d, J=8.0 Hz, 1H), 7.74 (s, 2H), 7.67 (d, J=7.6 Hz, 1H), 7.25 (d, J=8.6 Hz, 1H), 7.19 (s, 1H), 6.79 (dd, J=8.6 Hz, 2.2 Hz, 1H), 6.73 (d, J=2.2 Hz, 1H), 3.92-3.84 (m, 2H), 3.80 (s, 3H), 3.75-3.72 (m, 2H), 3.62-3.57 (m, 1H), 3.50-3.46 (m, 1H), 3.44-3.40 (m, 1H), 3.17-3.11 (m, 1H), 3.05-2.99 (m, 2H), 2.36 (s, 3H).

Example 8

(2-(2H-1,2,3-triazol-2-yl)phenyl)(5-(5-methoxybenzo[d]oxazol-2-yl) hexahydropyrrolo[3,4-c]pyrrol-2(1H)-yl)methanone

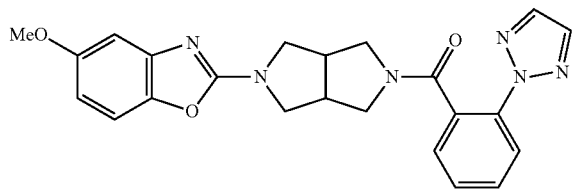 [SMILES: COc1ccc2oc(N3CC4CN(C(=O)c5ccccc5-n5nccn5)CC4C3)nc2c1]

2-Chloro-5-methoxybenzo[d]oxazole (0.275 g, 1.5 mmol) was reacted with (2-(2H-1,2,3-triazol-2-yl)phenyl)(hexahydropyrrolo[3,4-c]pyrrol-2(1H)-yl)methanone (0.283 g, 1.0 mmol) and potassium carbonate (0.69 g, 5.0 mmol) in acetonitrile (20 mL) according to the procedure as described in step 7 of example 1, and the crude product was purified by silica gel chromatography (PE/EtOAc (v/v)=1/2) to give the title compound as a yellow solid (0.316 g, 73.4%).

MS (ESI, pos. ion) m/z: 431.3 [M+H]$^+$; and $^1$H NMR (CDCl$_3$, 400 MHz) δ (ppm): 7.93 (dd, J=8.0 Hz, 4.1 Hz, 1H), 7.72 (s, 2H), 7.43-7.39 (m, 1H), 7.37-7.35 (m, 2H), 7.24 (d, J=8.6 Hz, 1H), 6.77 (dd, J=8.6 Hz, 2.5 Hz, 1H), 6.70 (d, J=2.5 Hz, 1H), 3.97-3.87 (m, 2H), 3.82 (s, 3H), 3.74-3.68 (m, 2H), 3.65-3.58 (m, 1H), 3.55-3.47 (m, 2H), 3.11-2.98 (m, 3H).

Example 9

(2-fluoro-6-(2H-1,2,3-triazol-2-yl)phenyl)(5-(5-methoxybenzo[d]oxazol-2-yl) hexahydropyrrolo[3,4-c]pyrrol-2(1H)-yl)methanone

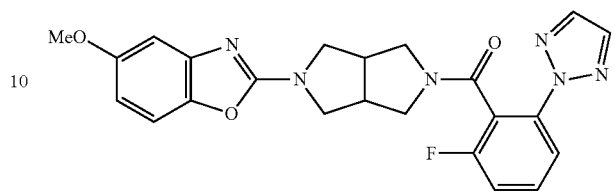

2-Chloro-5-methoxybenzo[d]oxazole (0.275 g, 1.5 mmol) was reacted with (2-fluoro-6-(2H-1,2,3-triazol-2-yl)phenyl)(hexahydropyrrolo[3,4-c]pyrrol-2(1H)-yl)methanone (0.301 g, 1.0 mmol) and potassium carbonate (0.69 g, 5.0 mmol) in acetonitrile (20 mL) according to the procedure as described in step 7 of example 1, and the crude product was purified by silica gel chromatography (PE/EtOAc (v/v)=1/3) to give the title compound as a pale yellow solid (0.321 g, 71.6%).

MS (ESI, pos. ion) m/z: 449.3 [M+H]$^+$; and $^1$H NMR (CDCl$_3$, 600 MHz) δ (ppm): 7.87-7.77 (m, 3H), 7.51-7.46 (m, 1H), 7.24 (d, J=8.6 Hz, 1H), 7.15-7.12 (m, 1H), 6.78 (dd, J=8.6 Hz, 2.2 Hz, 1H), 6.71 (d, J=2.2 Hz, 1H), 3.98-3.85 (m, 2H), 3.85-3.74 (m, 5H), 3.73-3.68 (m, 1H), 3.65-3.58 (m, 2H), 3.23-3.17 (m, 1H), 3.16-2.98 (m, 2H).

Example 10

(5-(benzo[d]oxazol-2-yl)hexahydropyrrolo[3,4-c]pyrrol-2(1H)-yl)(5-methyl-2-(2H-1,2,3-triazol-2-yl)phenyl)methanone

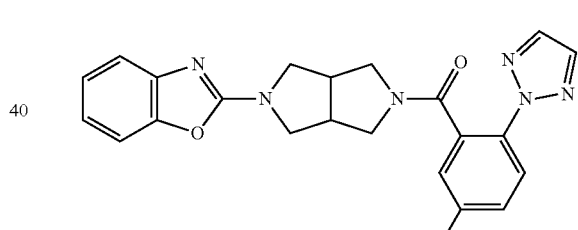

Step 1) Synthesis of benzo[d]oxazole-2-thiol

2-Aminophenol (4.365 g, 40.0 mmol) was reacted with ethyl potassium xanthate (6.733 g, 42.0 mmol) in ethanol (100 mL) according to the procedure as described in step 5 of example 1 to give the title compound as an off white solid (5.449 g, 90.1%).

MS (ESI, pos. ion) m/z: 152.1 [M+H]$^+$; and $^1$H NMR (CDCl$_3$, 400 MHz) δ (ppm): 10.24 (s, 1H), 7.77-7.73 (m, 2H), 7.18 (d, J=8.2 Hz, 1H), 7.02 (dt, J=8.0 Hz, 3.6 Hz, 1H).

Step 2) Synthesis of 2-chlorobenzo[d]oxazole

A mixture of benzo[d]oxazole-2-thiol (2.268 g, 15.0 mmol), sulfoxide chloride (20 mL, 272.6 mmol) and N,N-dimethylformamide (0.05 mL, 0.65 mmol) was heated to reflux for 3 hours, and then cooled and the solvent was removed in vacuo. The resulting product was used directly in the next step.

Step 3) Synthesis of (5-(benzo[d]oxazol-2-yl)hexahydropyrrolo[3,4-c]pyrrol-2(1H)-yl)(5-methyl-2-(2H-1,2,3-triazol-2-yl)phenyl)methanone 2-Chlorobenzo[d]oxazole (0.230 g, 1.5 mmol) was reacted with (hexahydropyrrolo[3,4-c]pyrrol-2(1H)-yl)(5-methyl-2-(2H-1,2,3-triazol-2-yl)phenyl)methanone (0.297 g, 1.0 mmol) and potassium carbonate (0.69 g, 5.0 mmol) in acetonitrile (20 mL) according to the procedure as described in step 7 of example 1, and the crude product was purified by silica gel chromatography (PE/EtOAc (v/v)=1/2) to give the title compound as a white solid (0.305 g, 73.6%).

MS (ESI, pos. ion) m/z: 415.3 [M+H]$^+$; and
$^1$H NMR (CDCl$_3$, 600 MHz) δ (ppm): 7.80 (d, J=8.0 Hz, 1H), 7.77-7.74 (m, 2H), 7.72 (s, 2H), 7.68 (d, J=7.6 Hz, 1H), 7.19 (s, 1H), 7.16 (d, J=8.1 Hz, 1H), 7.05-7.00 (m, 1H), 3.91-3.84 (m, 2H), 3.74-3.70 (m, 2H), 3.62-3.56 (m, 1H), 3.51-3.47 (m, 1H), 3.45-3.40 (m, 1H), 3.17-3.12 (m, 1H), 3.05-2.98 (m, 2H), 2.37 (s, 3H).

Example 11

(5-(benzo[d]oxazol-2-yl)hexahydropyrrolo[3,4-c]pyrrol-2(1H)-yl)(2-fluoro-6-(2H-1,2,3-triazol-2-yl)phenyl)methanone

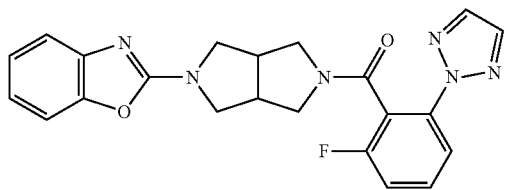 [SMILES: O=C(c1c(F)cccc1-n1nccn1)N1CC2CN(c3nc4ccccc4o3)CC2C1]

2-Chlorobenzo[d]oxazole (0.230 g, 1.5 mmol) was reacted with (2-fluoro-6-(2H-1,2,3-triazol-2-yl)phenyl)(hexahydropyrrolo[3,4-c]pyrrol-2(1H)-yl)methanone (0.301 g, 1.0 mmol) and potassium carbonate (0.69 g, 5.0 mmol) in acetonitrile (20 mL) according to the procedure as described in step 7 of example 1, and the crude product was purified by silica gel chromatography (PE/EtOAc (v/v)=1/2) to give the title compound as a pale yellow solid (0.290 g, 69.4%).

MS (ESI, pos. ion) m/z: 419.3 [M+H]$^+$; and
$^1$H NMR (CDCl$_3$, 600 MHz) δ (ppm): 7.82-7.77 (m, 3H), 7.74-7.70 (m, 2H), 7.51-7.46 (m, 1H), 7.18 (d, J=8.3 Hz, 1H), 7.14-7.11 (m, 1H), 7.05-7.02 (m, 1H), 3.99-3.79 (m, 4H), 3.75-3.71 (m, 1H), 3.69-3.61 (m, 2H), 3.30-3.26 (m, 1H), 3.17-3.07 (m, 2H).

Example 12

(5-(6-fluoroquinazolin-2-yl)hexahydropyrrolo[3,4-c]pyrrol-2(1H)-yl)(5-methyl-2-(2H-1,2,3-triazol-2-yl)phenyl)methanone

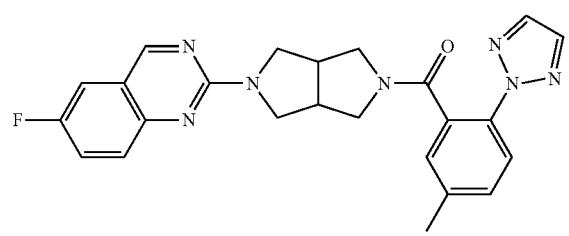 [SMILES: Cc1ccc(-n2nccn2)c(C(=O)N2CC3CN(c4ncc5cc(F)ccc5n4)CC3C2)c1]

Step 1) Synthesis of 6-fluoroquinazoline-2,4(1H,3H)-dione

To a 200 mL of sealing tube were added sequentially urea (29.0 g, 482.9 mmol) and 2-amino-5-fluoro benzoic acid (5.0 g, 32.2 mmol), the mixture was heated gradually to 160° C. under vigorous stirring, after reaction for 4 hours, and then the mixture was heated to 180° C. for 4 hours, then cooled to rt gradually. To the resulting mixture was added water (150 mL), the mixture was stirred at rt for 1 hour and filtered under vacuum. The residue was washed with a large amount of water until the filtrate become colorless, then washed with acetone (20 mL) and methanol (70 mL) successively, and then dried to give the title compound as a brick red solid (5.041 g, 86.8%).

MS (ESI, neg. ion) m/z: 179.1 [M−H]$^-$; and
$^1$H NMR (DMSO-d$_6$, 600 MHz) δ (ppm): 11.29 (s, 2H), 7.57 (dd, J=8.4 Hz, 2.7 Hz, 1H), 7.53 (td, J=8.7 Hz, 2.8 Hz, 1H), 7.19 (dd, J=8.8 Hz, 4.3 Hz, 1H).

Step 2) Synthesis of 2,4-dichloro-6-fluoroquinazoline

To phosphorus oxychloride (46.0 mL, 502.5 mmol) was added phosphorous pentachloride (12.5 g, 60.0 mmol), then 6-fluoroquinazoline-2,4(1H,3H)-dione (3.6 g, 20.0 mmol) was added slowly with stirring. The reaction mixture was heated to reflux and stirred for 9 hours, and then cooled and the solvent was removed in vacuo. To an ice water mixture (400 mL) was added the residue, the mixture was stirred for 0.5 hour and extracted with DCM (250 mL×3). The combined DCM layers were dried over sodium sulfate, filtered, and the filtrate was concentrated in vacuo, the residue was purified by silica gel chromatography (PE/EtOAc (v/v)=30/1) to give the title compound as a white solid (3.735 g, 86.0%).

MS (ESI, pos. ion) m/z: 216.9 [M+H]$^+$; and
$^1$H NMR (CDCl$_3$, 400 MHz) δ (ppm): 8.03 (dd, J=9.2 Hz, 4.9 Hz, 1H), 7.86 (dd, J=8.1 Hz, 2.7 Hz, 1H), 7.79-7.73 (m, 1H).

Step 3) Synthesis of 2-chloro-6-fluoroquinazoline

To zinc powder (1.65 g, 25.23 mmol) was added diluted hydrochloric acid (3 mL, 1 M). The mixture was stirred at rt for 10 min to activating zinc powder, and then washed with water to neutral, and then saturated aqueous NaCl (15 ml) and aqueous ammonia (6 mL, 25-28%) were added sequentially, then a solution of 2,4-dichloro-6-fluoroquinazoline (2.17 g, 10 mmol) in DCM (15 mL) was added slowly with stirring. The reaction mixture was heated gradually to reflux and stirred for 4 hours, and then cooled to rt and filtered by suction. The filter cake was washed with DCM (20 mL×3). The combined filtrates were dried over sodium sulfate, filtered, and the filtrate was concentrated in vacuo. The residue was purified by silica gel chromatography (PE/EtOAc (v/v)=15/1) to give the title compound as a pale yellow solid (1.133 g, 62.08%).

MS (ESI, pos. ion) m/z: 183.1 [M+H]$^+$; and
$^1$H NMR (CDCl$_3$, 400 MHz) δ (ppm): 9.28 (s, 1H), 8.02 (dd, J=9.2 Hz, 4.8 Hz, 1H), 7.73 (td, J=8.8 Hz, 2.7 Hz, 1H), 7.58 (dd, J=7.5 Hz, 2.7 Hz, 1H).

Step 4) Synthesis of (5-(6-fluoroquinazolin-2-yl)hexahydropyrrolo[3,4-c]pyrrol-2(1H)-yl)(5-methyl-2-(2H-1,2,3-triazol-2-yl)phenyl)methanone 2-Chloro-6-fluoroquinazoline (0.151 g, 0.827 mmol) was reacted with (hexahydropyrrolo[3,4-c]pyrrol-2(1H)-yl)(5- methyl-2-(2H-1,2,3-triazol-2-yl)phenyl)methanone (0.271 g, 0.911 mmol) and potassium carbonate (0.343 g, 2.48 mmol) in acetonitrile (30 mL) according to the procedure as described in step 7 of example 1, and the crude product was purified by silica gel chromatography (PE/EtOAc (v/v)=1/1) to give the title compound as a yellow solid (0.295 g, 80.4%).

MS (ESI, pos. ion) m/z: 444.5 [M+H]$^+$; and
$^1$H NMR (CDCl$_3$, 600 MHz) β (ppm): 8.95 (s, 1H), 7.81 (d, J=8.2 Hz, 1H), 7.68 (s, 2H), 7.59-7.56 (m, 1H), 7.43 (td, J=8.8 Hz, 2.6 Hz, 1H), 7.29-7.25 (m, 2H), 7.21 (s, 1H), 3.97-3.93 (m, 1H), 3.90-3.85 (m, 1H), 3.73-3.65 (m, 3H), 3.58-3.56 (m, 1H), 3.38-3.34 (m, 1H), 3.08-2.96 (m, 3H), 2.38 (s, 3H).

Example 13

(2-(2H-1,2,3-triazol-2-yl)phenyl)(5-(6-fluoroquinazolin-2-yl)hexahydropyrrolo [3,4-c]pyrrol-2(1H)-yl)methanone

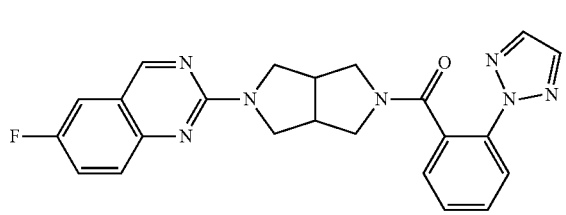 [SMILES: O=C(c1ccccc1-n1nccn1)N1CC2CN(c3ncc4cc(F)ccc4n3)CC2C1]

2-Chloro-6-fluoroquinazoline (0.142 g, 0.778 mmol) was reacted with (2-(2H-1,2,3-triazol-2-yl)phenyl)(hexahydropyrrolo[3,4-c]pyrrol-2(1H)-yl)methanone (0.201 g, 0.709 mmol) and triethylamine (0.3 mL, 2 mmol) in acetonitrile (10 mL) according to the procedure as described in step 7 of example 1, and the crude product was purified by silica gel chromatography (PE/EtOAc (v/v)=1/1) to give the title compound as a yellow solid (0.205 g, 67.3%).

MS (ESI, pos. ion) m/z: 430.5 [M+H]$^+$; and
$^1$H NMR (CDCl$_3$, 600 MHz) δ (ppm): 8.95 (s, 1H), 7.95 (d, J=8.0 Hz, 1H), 7.70 (s, 2H), 7.58 (dd, J=8.0 Hz, 4.2 Hz, 1H), 7.53-7.47 (m, 1H), 7.46-7.37 (m, 3H), 7.28 (dd, J=7.9 Hz, 2.4 Hz, 1H), 3.95 (dd, J=11.4 Hz, 7.8 Hz, 1H), 3.92-3.84 (m, 1H), 3.73-3.67 (m, 3H), 3.62-3.56 (m, 1H), 3.40 (s, 1H), 3.11-2.92 (m, 3H).

Example 14

(2-fluoro-6-(2H-1,2,3-triazol-2-yl)phenyl)(5-(6-fluoroquinazolin-2-yl) hexahydropyrrolo[3,4-c]pyrrol-2(1H)-yl)methanone

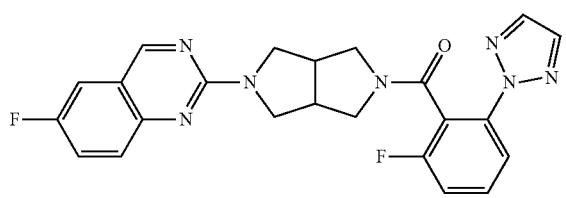 [SMILES: O=C(c1c(F)cccc1-n1nccn1)N1CC2CN(c3ncc4cc(F)ccc4n3)CC2C1]

2-Chloro-6-fluoroquinazoline (0.250 g, 1.37 mmol) was reacted with (2-fluoro-6-(2H-1,2,3-triazol-2-yl)phenyl)(hexahydropyrrolo[3,4-c]pyrrol-2(1H)-yl)methanone (0.358 g, 1.19 mmol) and triethylamine (0.9 mL, 6 mmol) in acetonitrile (10 mL) according to the procedure as described in step 7 of example 1, and the crude product was purified by silica gel chromatography (PE/EtOAc (v/v)=1/1) to give the title compound as a pale yellow solid (0.401 g, 75.4%).

MS (ESI, pos. ion) m/z: 448.5 [M+H]$^+$; and
$^1$H NMR (CDCl$_3$, 600 MHz) δ (ppm): 8.97 (d, J=1.8 Hz, 1H), 7.90-7.77 (m, 2H), 7.69 (s, 1H), 7.59 (d, J=4.3 Hz, 1H), 7.53-7.38 (m, 2H), 7.29 (dd, J=7.6 Hz, 2.5 Hz, 1H), 7.14 (dd, J=17.9 Hz, 8.8 Hz, 1H), 4.04-3.88 (m, 2H), 3.87-3.78 (m, 2H), 3.77-3.66 (m, 2H), 3.65-3.55 (m, 1H), 3.37-3.25 (m, 1H), 3.21-3.01 (m, 2H).

Example 15

(5-(6-chloroquinazolin-2-yl)hexahydropyrrolo[3,4-c]pyrrol-2(1H)-yl)(5-methyl-2-(2H-1,2,3-triazol-2-yl)phenyl)methanone

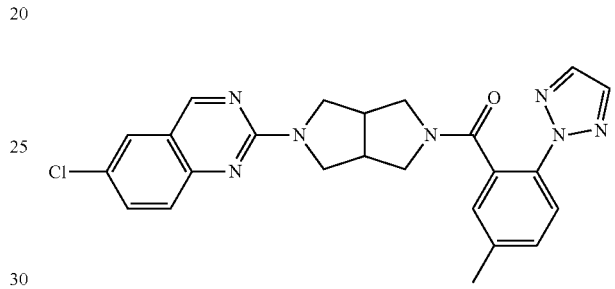

Step 1) Synthesis of 6-chloroquinazoline-2,4(1H,3H)-dione

2-Amino-5-chlorobenzoic acid (3.432 g, 20.0 mmol) was reacted with urea (18.016 g, 300.0 mmol) in a 100 mL of sealing tube according to the procedure as described in step 1 of example 12 to give the title compound as a gray solid (3.272 g, 83.2%).

MS (ESI, neg. ion) m/z: 195.1 [M−H]$^-$; and
$^1$H NMR (DMSO-d$_6$, 600 MHz) δ (ppm): 11.34 (s, 2H), 7.81 (d, J=2.5 Hz, 1H), 7.67 (dd, J=8.7 Hz, 2.5 Hz, 1H), 7.18 (d, J=8.7H, 1H).

Step 2) Synthesis of 2,4,6-trichloroquinazoline

6-Chloroquinazoline-2,4(1H,3H)-dione (2.66 g, 13.51 mmol) was reacted with phosphorous pentachloride (2.66 g, 13.51 mmol) in phosphorus oxychloride (30.9 mL, 338 mmol) according to the procedure as described in step 2 of example 12, and the crude product was purified by silica gel chromatography (PE/EtOAc (v/v)=50/1) to give the title compound as a white solid (0.881 g, 27.9%).

MS (ESI, pos. ion) m/z: 232.9 [M+1-1]$^+$; and
$^1$H NMR (DMSO-d$_6$, 600 MHz) δ (ppm): 8.02 (d, J=2.5 Hz, 1H), 7.86 (dd, J=8.7 Hz, 2.5 Hz, 1H), 7.64 (d, J=8.7H, 1H).

Step 3) Synthesis of 2,6-dichlorofluoroquinazoline 2,4,6-Trichloroquinazoline (2.335 g, 10 mmol) was reacted with zinc powder (1.65 g, 25.23 mmol)(activation according to the procedure as described in step 3 of example 12) in a solution of saturated aqueous NaCl solution (15 mL), aqueous ammonia (6 mL, 25-28%) and DCM (15 mL) according to the procedure as described in step 3 of example 12, and the crude product was purified by silica gel chromatography (PE/EtOAc (v/v)=15/1) to give the title compound as a white solid (0.906 g, 45.5%).

MS (ESI, pos. ion) m/z: 198.9 [M+1-1]⁺; and

¹H NMR (CDCl₃, 400 MHz) δ (ppm): 9.30 (s, 1H), 8.00 (d, J=2.4 Hz, 1H), 7.74 (dd, J=8.6 Hz, 2.4 Hz, 1H), 7.50 (d, J=8.6 Hz, 1H).

Step 4) Synthesis of (5-(6-chloroquinazolin-2-yl)hexahydropyrrolo[3,4-c]pyrrol-2(1H)-yl) (5-methyl-2-(2H-1,2,3-triazol-2-yl)phenyl)methanone 2,6-Dichloroquinazoline (0.199 g, 1.0 mmol) was reacted with (hexahydropyrrolo[3,4-c]pyrrol-2(1H)-yl)(5-methyl-2-(2H-1,2,3-triazol-2-yl)phenyl)methanone (0.297 g, 1.0 mmol) and potassium carbonate (0.346 g, 2.5 mmol) in acetonitrile (30 mL) according to the procedure as described in step 7 of example 1, and the crude product was purified by silica gel chromatography (PE/EtOAc (v/v)=1/1) to give the title compound as a pale yellow solid (0.374 g, 81.3%).

MS (ESI, pos. ion) m/z: 460.4 [M+H]⁺; and

¹H NMR (CDCl₃, 600 MHz) δ (ppm): 8.99 (s, 1H), 7.80 (d, J=8.2 Hz, 1H), 7.69 (s, 2H), 7.66 (d, J=2.6 Hz, 1H), 7.61-7.57 (m, 1H), 7.49-7.45 (m, 1H), 7.32 (d, J=8.6 Hz, 1H), 7.21 (s, 1H), 3.99-3.94 (m, 1H), 3.91-3.85 (m, 1H), 3.73-3.66 (m, 3H), 3.58-3.55 (m, 1H), 3.38-3.32 (m, 1H), 3.09-2.98 (m, 3H), 2.37 (s, 3H).

Example 16

(2-(2H-1,2,3-triazol-2-yl)phenyl)(5-(6-chloroquinazolin-2-yl)hexahydropyrrolo [3,4-c]pyrrol-2(1H)-yl)methanone

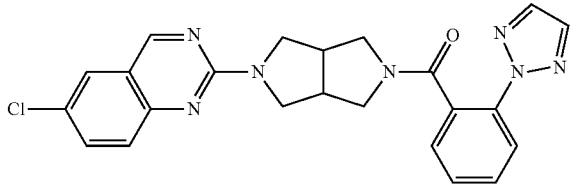 [SMILES: O=C(c1ccccc1-n1nccn1)N1CC2CN(c3ncc4cc(Cl)ccc4n3)CC2C1]

2,6-Dichloroquinazoline (0.199 g, 1.0 mmol) was reacted with (2-(2H-1,2,3-triazol-2-yl)phenyl)(hexahydropyrrolo[3,4-c]pyrrol-2(1H)-yl)methanone (0.283 g, 1.0 mmol) and potassium carbonate (0.346 g, 2.5 mmol) in acetonitrile (30 mL) according to the procedure as described in step 7 of example 1, and the crude product was purified by silica gel chromatography (PE/EtOAc (v/v)=1/1) to give the title compound as a yellow solid (0.310 g, 69.5%).

MS (ESI, pos. ion) m/z: 446.4 [M+H]⁺; and

¹H NMR (CDCl₃, 400 MHz) δ (ppm): 8.99 (s, 1H), 7.94 (d, J=8.1 Hz, 1H), 7.70 (s, 2H), 7.65 (d, J=2.5 Hz, 1H), 7.55-7.50 (m, 1H), 7.49-7.46 (m, 1H), 7.45-7.42 (m, 2H), 7.34 (d, J=8.5 Hz, 1H), 3.95-3.87 (m, 2H), 3.78-3.72 (m, 2H), 3.66-3.58 (m, 1H), 3.54-3.44 (m, 1H), 3.38 (s, 1H), 3.11-2.99 (m, 3H).

Example 17

(5-(6-chloroquinazolin-2-yl)hexahydropyrrolo[3,4-c]pyrrol-2(1H)-yl)(2-fluoro-6-(2H-1,2,3-triazol-2-yl)phenyl)methanone

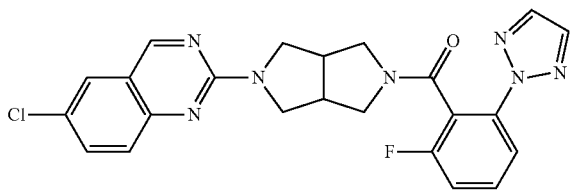 [SMILES: O=C(c1c(F)cccc1-n1nccn1)N1CC2CN(c3ncc4cc(Cl)ccc4n3)CC2C1]

2,6-Dichloroquinazoline (0.199 g, 1.0 mmol) was reacted with (2-fluoro-6-(2H-1,2,3-triazol-2-yl)phenyl)(hexahydropyrrolo[3,4-c]pyrrol-2(1H)-yl)methanone (0.301 g, 1.0 mmol) and potassium carbonate (0.346 g, 2.5 mmol) in acetonitrile (10 mL) according to the procedure as described in step 7 of example 1, and the crude product was purified by silica gel chromatography (PE/EtOAc (v/v)=1/1) to give the title compound as a yellow solid (0.367 g, 79.2%).

MS (ESI, pos. ion) m/z: 464.3 [M+H]⁺; and

¹H NMR (CDCl₃, 600 MHz) δ (ppm): 8.97 (s, 1H), 7.84-7.78 (m, 3H), 7.65 (d, J=2.6 Hz, 1H), 7.50-7.44 (m, 2H), 7.43-7.42 (m, 1H), 7.15-7.12 (m, 1H), 4.00-3.87 (m, 2H), 3.85-3.77 (m, 2H), 3.76-3.66 (m, 2H), 3.64-3.55 (m, 1H), 3.38-3.27 (m, 1H), 3.20-3.01 (m, 2H).

Example 18

(5-(6-methoxyquinazolin-2-yl)hexahydropyrrolo[3,4-c]pyrrol-2(1H)-yl)(5-methyl-2-(2H-1,2,3-triazol-2-yl)phenyl)methanone

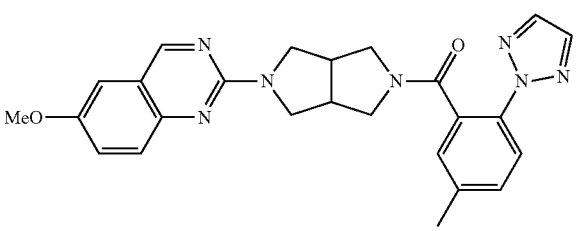 [SMILES: COc1ccc2nc(N3CC4CN(C(=O)c5cc(C)ccc5-n5nccn5)CC4C3)ncc2c1]

Step 1) Synthesis of 6-methoxyquinazoline-2,4(1H,3H)-dione

2-Amino-5-methoxybenzoic acid (2.51 g, 15.0 mmol) was reacted with urea (13.51 g, 225.0 mmol) in a 200 mL sealing tube according to the procedure as described in step 1 of example 12 to give the title compound as a gray solid (2.30 g, 79.7%).

MS (ESI, neg. ion) m/z: 191.0 [M−H]⁻; and

¹H NMR (DMSO-d₆, 400 MHz) δ (ppm): 11.24 (s, 1H), 11.06 (s, 1H), 7.36 (d, J=2.9 Hz, 1H), 7.32 (dd, J=8.8 Hz, 2.9 Hz, 1H), 7.16 (d, J=8.8 Hz, 1H), 3.82 (s, 3H).

Step 2) Synthesis of 2,4-dichloro-6-methoxyquinazoline

6-Methoxyquinazolin-2,4(1H,3H)-dione (1.84 g, 9.57 mmol) was reacted with phosphorous pentachloride (5.97 g, 28.65 mmol) in phosphorus oxychloride (21.9 mL, 239 mmol) according to the procedure as described in step 2 of example 12, and the crude product was purified by silica gel chromatography (PE/EtOAc (v/v)=10/1) to give the title compound as a white solid (1.78 g, 81.2%).

MS (ESI, pos. ion) m/z: 229.1 [M+H]$^+$; and
$^1$H NMR (CDCl$_3$, 400 MHz) δ (ppm): 7.89 (d, J=9.2 Hz, 1H), 7.61 (dd, J=9.2 Hz, 2.8 Hz, 1H), 7.40 (d, J=2.7 Hz, 1H), 3.99 (s, 3H).

Step 3) Synthesis of 2-chloro-6-methoxyquinazoline 2,4-Dichloro-6-methoxyquinazoline (2.291 g, 10 mmol) was reacted with zinc powder (1.65 g, 25.23 mmol)(activation according to the procedure as described in step 3 of example 12) in a solution of saturated aqueous NaCl solution (15 mL), aqueous ammonia (6 mL, 25-28%) and DCM (15 mL) according to the procedure as described in step 3 of example 12, and the crude product was purified by silica gel chromatography (PE/EtOAc (v/v)=15/1) to give the title compound as a white solid (0.792 g, 40.7%).

MS (ESI, pos. ion) m/z: 195.1 [M+H]$^+$; and
$^1$H NMR (CDCl$_3$, 400 MHz) δ (ppm): 9.33 (s, 1H), 7.88 (d, J=9.0 Hz, 1H), 7.45 (dd, J=9.0 Hz, 2.8 Hz, 1H), 7.28 (d, J=2.9 Hz, 1H), 3.84 (s, 3H).

Step 4) Synthesis of (5-(6-methoxyquinazolin-2-yl) hexahydropyrrolo[3,4-c]pyrrol-2(1H)-yl)(5-methyl-2-(2H-1,2,3-triazol-2-yl)phenyl)methanone 2-Chloro-6-methoxyquinazoline (0.195 g, 1.0 mmol) was reacted with (hexahydropyrrolo[3,4-c]pyrrol-2(1H)-yl)(5-methyl-2-(2H-1,2,3-triazol-2-yl)phenyl)methanone (0.297 g, 1.0 mmol) and potassium carbonate (0.346 g, 2.5 mmol) in acetonitrile (30 mL) according to the procedure as described in step 7 of example 1, and the crude product was purified by silica gel chromatography (PE/EtOAc (v/v)=1/1) to give the title compound as an orange-yellow solid (0.358 g, 78.7%).

MS (ESI, pos. ion) m/z: 456.3 [M+H]$^+$; and
$^1$H NMR (CDCl$_3$, 600 MHz) δ (ppm): 8.98 (s, 1H), 7.80 (d, J=8.2 Hz, 1H), 7.71 (s, 2H), 7.67 (d, J=8.9 Hz, 1H), 7.60-7.57 (m, 1H), 7.40 (dd, J=8.9 Hz, 2.7 Hz, 1H), 7.25 (d, J=2.7 Hz, 1H), 7.21 (s, 1H), 3.99-3.94 (m, 1H), 3.91-3.86 (m, 1H), 3.83 (s, 3H), 3.74-3.67 (m, 3H), 3.57-3.53 (m, 1H), 3.36-3.31 (m, 1H), 3.09-2.97 (m, 3H), 2.37 (s, 3H).

Example 19

(2-(2H-1,2,3-triazol-2-yl)phenyl)(5-(6-methoxyquinazolin-2-yl) hexahydropyrrolo[3,4-c]pyrrol-2(1H)-yl)methanone

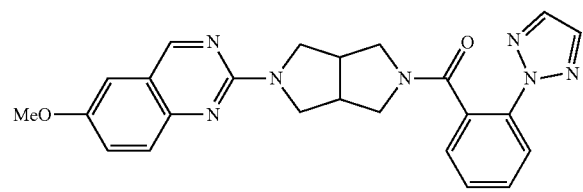 [SMILES: COc1ccc2nc(N3CC4CN(C(=O)c5ccccc5-n5nccn5)CC4C3)ncc2c1]

2-Chloro-6-methoxyquinazoline (0.195 g, 1.0 mmol) was reacted with (2-(2H-1,2,3-triazol-2-yl)phenyl)(hexahydropyrrolo[3,4-c]pyrrol-2(1H)-yl)methanone (0.283 g, 1.0 mmol) and potassium carbonate (0.346 g, 2.5 mmol) in acetonitrile (30 mL) according to the procedure as described in step 7 of example 1, and the crude product was purified by silica gel chromatography (PE/EtOAc (v/v)=1/1) to give the title compound as an orange-yellow solid (0.337 g, 76.3%).

MS (ESI, pos. ion) m/z: 442.3 [M+H]$^+$; and
$^1$H NMR (CDCl$_3$, 400 MHz) δ (ppm): 8.99 (s, 1H), 7.97 (d, J=8.0 Hz, 1H), 7.71 (s, 2H), 7.68 (d, J=9.0 Hz, 1H), 7.56-7.50 (m, 1H), 7.46-7.42 (m, 2H), 7.41-7.38 (m, 1H), 7.26 (d, J=2.8 Hz, 1H), 3.95-3.85 (m, 2H), 3.84 (s, 3H), 3.76-3.70 (m, 2H), 3.63-3.57 (m, 1H), 3.52-3.44 (m, 1H), 3.39 (s, 1H), 3.12-2.99 (m, 3H).

Example 20

(2-fluoro-6-(2H-1,2,3-triazol-2-yl)phenyl)(5-(6-methoxyquinazolin-2-yl) hexahydropyrrolo[3,4-c]pyrrol-2(1H)-yl)methanone

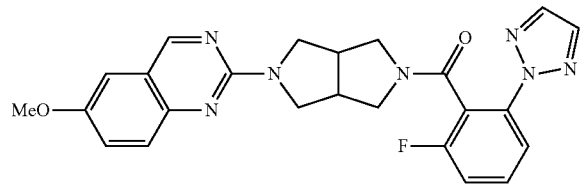 [SMILES: COc1ccc2nc(N3CC4CN(C(=O)c5c(F)cccc5-n5nccn5)CC4C3)ncc2c1]

2-Chloro-6-methoxyquinazoline (0.195 g, 1.0 mmol) was reacted with (2-fluoro-6-(2H-1,2,3-triazol-2-yl)phenyl)(hexahydropyrrolo[3,4-c]pyrrol-2(1H)-yl)methanone (0.301 g, 1.0 mmol) and potassium carbonate (0.346 g, 2.5 mmol) in acetonitrile (12 mL) according to the procedure as described in step 7 of example 1, and the crude product was purified by silica gel chromatography (PE/EtOAc (v/v)=1/1) to give the title compound as a pale yellow solid (0.300 g, 65.3%).

MS (ESI, pos. ion) m/z: 460.3 [M+H]$^+$; and
$^1$H NMR (CDCl$_3$, 600 MHz) δ (ppm): 8.98 (s, 1H), 7.84-7.78 (m, 3H), 7.69 (d, J=8.9 Hz, 1H), 7.50-7.44 (m, 1H), 7.42-7.39 (m, 1H), 7.25 (d, J=2.9 Hz, 1H), 7.15-7.12 (m, 1H), 4.04-3.88 (m, 2H), 3.87-3.78 (m, 5H), 3.77-3.66 (m, 2H), 3.65-3.55 (m, 1H), 3.37-3.25 (m, 1H), 3.21-3.01 (m, 2H).

Compounds of Examples 21 to 35 can be prepared from corresponding materials according to the procedure as described in Example 1, wherein the materials are commercially available or obtainable through simple process known to those skilled in the art.

Example 21

(5-methyl-2-(2H-1,2,3-triazol-2-yl)phenyl)(5-(5-trifluoromethylbenzo[d]oxazol-2-yl)hexahydropyrrolo[3,4-c]pyrrol-2(1H)-yl)methanone

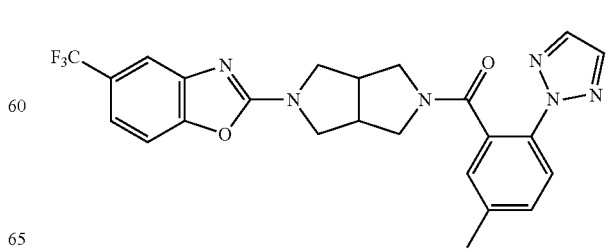

MS (ESI, pos. ion) m/z: 483.4 [M+H]$^+$.

Example 22

(2-(2H-1,2,3-triazol-2-yl)phenyl)(5-(5-trifluoromethylbenzo[d]oxazol-2-yl) hexahydropyrrolo[3,4-c]pyrrol-2(1H)-yl)methanone

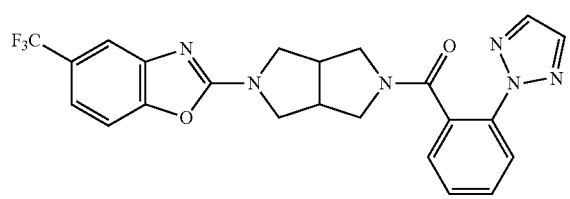 [SMILES: O=C(c1ccccc1-n1nccn1)N1CC2CN(c3nc4cc(C(F)(F)F)ccc4o3)CC2C1]

MS (ESI, pos. ion) m/z: 469.3 [M+H]$^+$.

Example 23

(2-fluoro-6-(2H-1,2,3-triazol-2-yl)phenyl)(5-(5-trifluoromethylbenzo[d]oxazol-2-yl)hexahydropyrrolo[3,4-c]pyrrol-2(1H)-yl)methanone

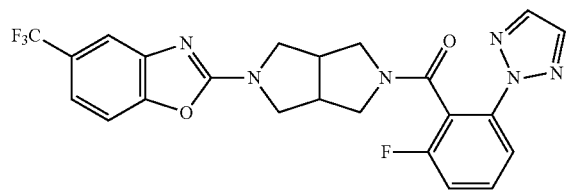 [SMILES: O=C(c1c(F)cccc1-n1nccn1)N1CC2CN(c3nc4cc(C(F)(F)F)ccc4o3)CC2C1]

MS (ESI, pos. ion) m/z: 487.1 [M+H]$^+$.

Example 24

2-(5-(5-methyl-2-(2H-1,2,3-triazol-2-yl)benzoyl)hexahydropyrrolo[3,4-c]pyrrol-2(1H)-yl)benzo[d]oxazole-5-carbonitrile

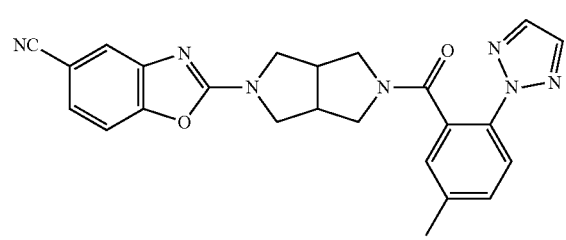 [SMILES: Cc1ccc(-n2nccn2)c(C(=O)N2CC3CN(c4nc5cc(C#N)ccc5o4)CC3C2)c1]

MS (ESI, pos. ion) m/z: 440.5 [M+H]$^+$.

Example 25

2-(5-(2-(2H-1,2,3-triazol-2-yl)benzoyl)hexahydropyrrolo[3,4-c]pyrrol-2(1H)-yl)benzo[d]oxazole-5-carbonitrile

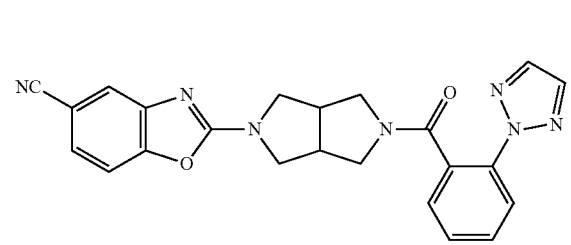 [SMILES: N#Cc1ccc2oc(N3CC4CN(C(=O)c5ccccc5-n5nccn5)CC4C3)nc2c1]

MS (ESI, pos. ion) m/z: 426.6 [M+H]$^+$.

Example 26

2-(5-(2-fluoro-6-(2H-1,2,3-triazol-2-yl)benzoyl)hexahydropyrrolo[3,4-c]pyrrol-2(1H)-yl)benzo[d]oxazole-5-carbonitrile

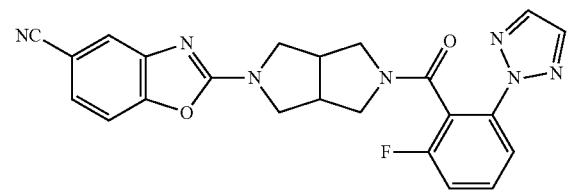 [SMILES: N#Cc1ccc2oc(N3CC4CN(C(=O)c5c(F)cccc5-n5nccn5)CC4C3)nc2c1]

MS (ESI, pos. ion) m/z: 444.1 [M+H]$^+$.

Example 27

(5-(6-chlorobenzo[d]oxazol-2-yl)hexahydropyrrolo[3,4-c]pyrrol-2(1H)-yl)(5-methyl-2-(2H-1,2,3-triazol-2-yl)phenyl)methanone

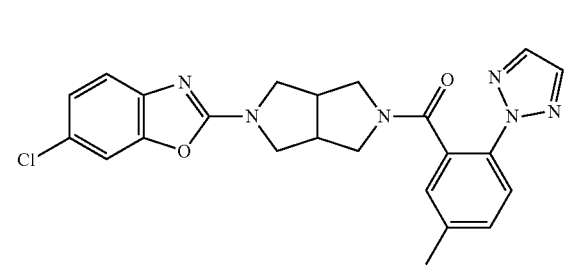 [SMILES: Cc1ccc(-n2nccn2)c(C(=O)N2CC3CN(c4nc5ccc(Cl)cc5o4)CC3C2)c1]

MS (ESI, pos. ion) m/z: 449.9 [M+H]$^+$.

Example 28

(2-(2H-1,2,3-triazol-2-yl)phenyl)(5-(6-chlorobenzo[d]oxazol-2-yl) hexahydropyrrolo[3,4-c]pyrrol-2(1H)-yl)methanone

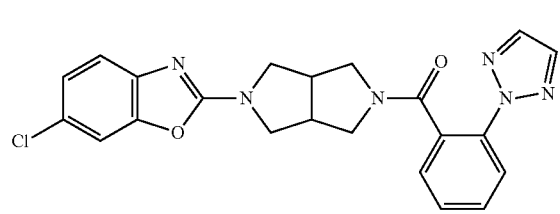 [SMILES: O=C(c1ccccc1-n1nccn1)N1CC2CN(c3nc4ccc(Cl)cc4o3)CC2C1]

MS (ESI, pos. ion) m/z: 435.8 [M+H]$^+$.

Example 29

(5-(6-chlorobenzo[d]oxazol-2-yl)hexahydropyrrolo[3,4-c]pyrrol-2(1H)-yl)(2-fluoro-6-(2H-1,2,3-triazol-2-yl)phenyl)methanone

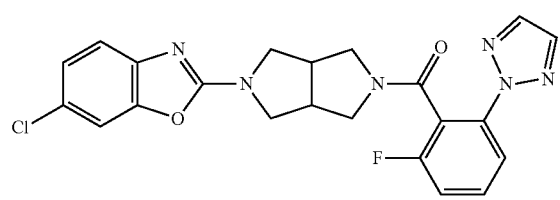 [SMILES: O=C(c1c(F)cccc1-n1nccn1)N1CC2CN(c3nc4ccc(Cl)cc4o3)CC2C1]

MS (ESI, pos. ion) m/z: 453.7 [M+H]$^+$.

Example 30

(5-(6-fluorobenzo[d]oxazol-2-yl)hexahydropyrrolo[3,4-c]pyrrol-2(1H)-yl)(5-methyl-2-(2H-1,2,3-triazol-2-yl)phenyl)methanone

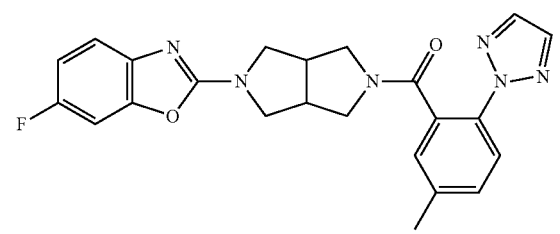 [SMILES: Cc1ccc(-n2nccn2)c(C(=O)N2CC3CN(c4nc5ccc(F)cc5o4)CC3C2)c1]

MS (ESI, pos. ion) m/z: 433.4 [M+H]$^+$.

Example 31

(2-(2H-1,2,3-triazol-2-yl)phenyl)(5-(6-fluorobenzo[d]oxazol-2-yl) hexahydropyrrolo[3,4-c]pyrrol-2(1H)-yl)methanone

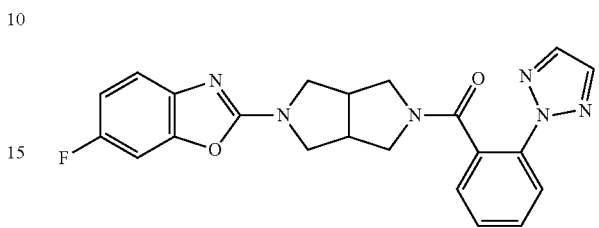

MS (ESI, pos. ion) m/z: 419.5 [M+H]$^+$.

Example 32

(2-fluoro-6-(2H-1,2,3-triazol-2-yl)phenyl)(5-(6-fluorobenzo[d]oxazol-2-yl) hexahydropyrrolo[3,4-c]pyrrol-2(1H)-yl)methanone

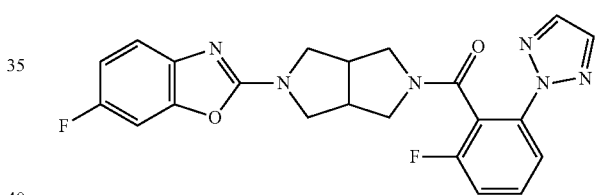

MS (ESI, pos. ion) m/z: 437.1 [M+H]$^+$.

Example 33

(5-(4-methoxybenzo[d]oxazol-2-yl)hexahydropyrrolo[3,4-c]pyrrol-2(1H)-yl) (5-methyl-2-(2H-1,2,3-triazol-2-yl)phenyl)methanone

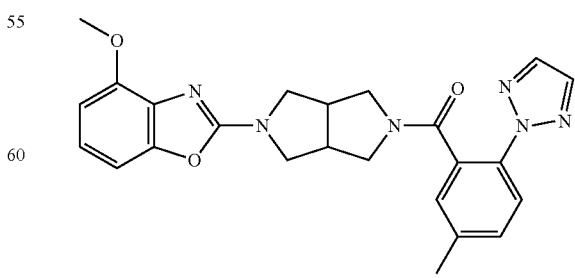

MS (ESI, pos. ion) m/z: 445.3 [M+H]$^+$.

Example 34

(2-(2H-1,2,3-triazol-2-yl)phenyl)(5-(4-methoxybenzo[d]oxazol-2-yl) hexahydropyrrolo[3,4-c]pyrrol-2(1H)-yl)methanone

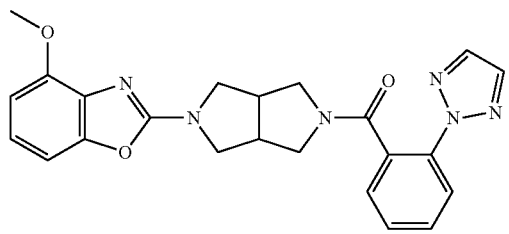 [SMILES: COc1cccc2oc(N3CC4CN(C(=O)c5ccccc5-n5nccn5)CC4C3)nc12]

MS (ESI, pos. ion) m/z: 431.5 [M+H]$^+$.

Example 35

(2-fluoro-6-(2H-1,2,3-triazol-2-yl)phenyl)(5-(4-methoxybenzo[d]oxazol-2-yl) hexahydropyrrolo[3,4-c]pyrrol-2(1H)-yl)methanone

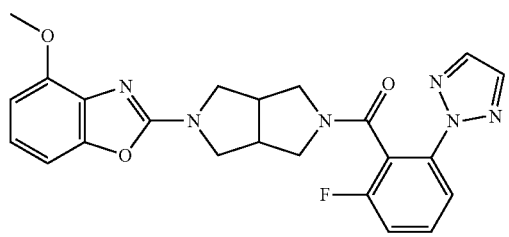 [SMILES: COc1cccc2oc(N3CC4CN(C(=O)c5c(F)cccc5-n5nccn5)CC4C3)nc12]

MS (ESI, pos. ion) m/z: 449.6 [M+H]$^+$.

Compounds of Examples 36 to 45 can be prepared from corresponding materials according to the procedure as described in Example 12, wherein the materials are commercially available or obtainable through simple process known to those skilled in the art.

Example 36

(5-(7-fluoroquinazolin-2-yl)hexahydropyrrolo[3,4-c]pyrrol-2(1H)-yl)(5-methyl-2-(2H-1,2,3-triazol-2-yl)phenyl)methanone

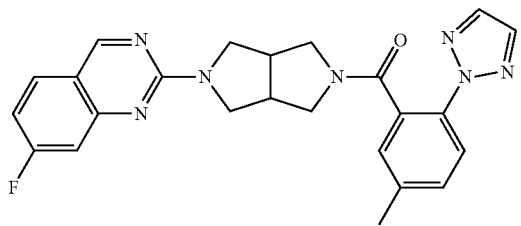 [SMILES: Cc1ccc(-n2nccn2)c(C(=O)N2CC3CN(c4ncc5ccc(F)cc5n4)CC3C2)c1]

MS (ESI, pos. ion) m/z: 444.5 [M+H]$^+$.

Example 37

(2-(2H-1,2,3-triazol-2-yl)phenyl)(5-(7-fluoroquinazolin-2-yl) hexahydropyrrolo[3,4-c]pyrrol-2(1H)-yl)methanone

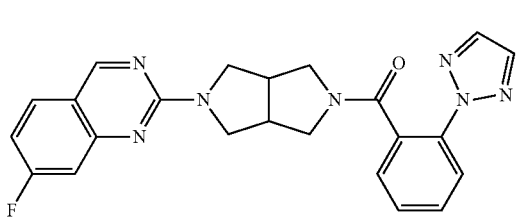 [SMILES: O=C(c1ccccc1-n1nccn1)N1CC2CN(c3ncc4ccc(F)cc4n3)CC2C1]

MS (ESI, pos. ion) m/z: 430.1 [M+H]$^+$.

Example 38

(2-fluoro-6-(2H-1,2,3-triazol-2-yl)phenyl)(5-(7-fluoroquinazolin-2-yl) hexahydropyrrolo[3,4-c]pyrrol-2(1H)-yl)methanone

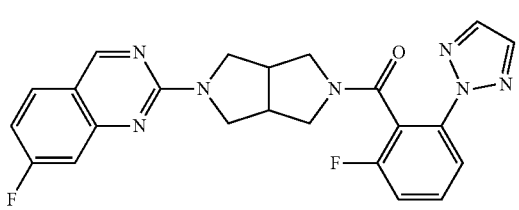 [SMILES: O=C(c1c(F)cccc1-n1nccn1)N1CC2CN(c3ncc4ccc(F)cc4n3)CC2C1]

MS (ESI, pos. ion) m/z: 448.6 [M+H]$^+$.

Example 39

(5-(7-methoxyquinazolin-2-yl)hexahydropyrrolo[3,4-c]pyrrol-2(1H)-yl)(5-methyl-2-(2H-1,2,3-triazol-2-yl)phenyl)methanone

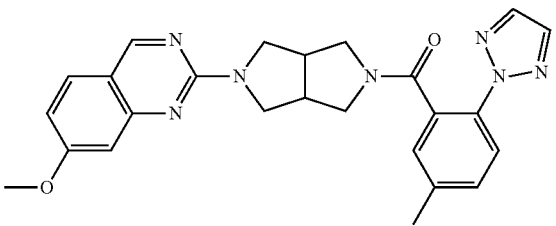 [SMILES: COc1ccc2cnc(N3CC4CN(C(=O)c5cc(C)ccc5-n5nccn5)CC4C3)nc2c1]

MS (ESI, pos. ion) m/z: 456.6 [M+H]$^+$.

Example 40

(2-(2H-1,2,3-triazol-2-yl)phenyl)(5-(7-methoxyquinazolin-2-yl) hexahydropyrrolo[3,4-c]pyrrol-2(1H)-yl)methanone

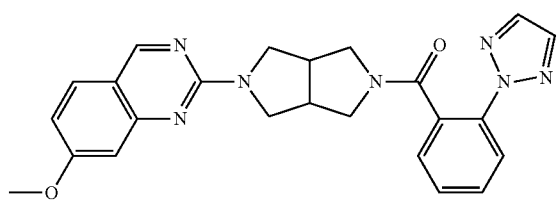 [SMILES: COc1ccc2cnc(N3CC4CN(C(=O)c5ccccc5-n5nccn5)CC4C3)nc2c1]

MS (ESI, pos. ion) m/z: 442.2 [M+H]+.

Example 41

(2-fluoro-6-(2H-1,2,3-triazol-2-yl)phenyl)(5-(7-methoxyquinazolin-2-yl) hexahydropyrrolo[3,4-c]pyrrol-2(1H)-yl)methanone

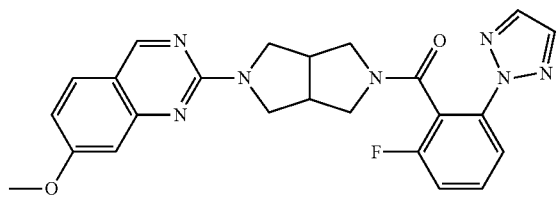 [SMILES: COc1ccc2cnc(N3CC4CN(C(=O)c5c(F)cccc5-n5nccn5)CC4C3)nc2c1]

MS (ESI, pos. ion) m/z: 460.8 [M+H]+.

Example 42

(5-(5-methoxyquinazolin-2-yl)hexahydropyrrolo[3,4-c]pyrrol-2(1H)-yl)(5-methyl-2-(2H-1,2,3-triazol-2-yl)phenyl)methanone

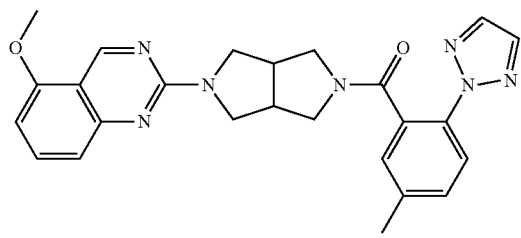 [SMILES: COc1cccc2nc(N3CC4CN(C(=O)c5cc(C)ccc5-n5nccn5)CC4C3)ncc12]

MS (ESI, pos. ion) m/z: 456.5 [M+H]+.

Example 43

(2-(2H-1,2,3-triazol-2-yl)phenyl)(5-(5-methoxyquinazolin-2-yl) hexahydropyrrolo[3,4-c]pyrrol-2(1H)-yl)methanone

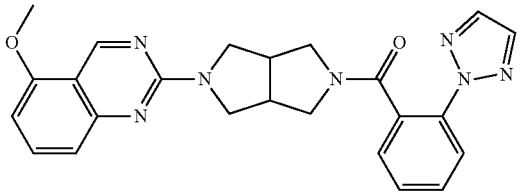 [SMILES: COc1cccc2nc(N3CC4CN(C(=O)c5ccccc5-n5nccn5)CC4C3)ncc12]

MS (ESI, pos. ion) m/z: 442.4 [M+H]+

Example 44

(2-fluoro-6-(2H-1,2,3-triazol-2-yl)phenyl)(5-(5-methoxyquinazolin-2-yl) hexahydropyrrolo[3,4-c]pyrrol-2(1H)-yl)methanone

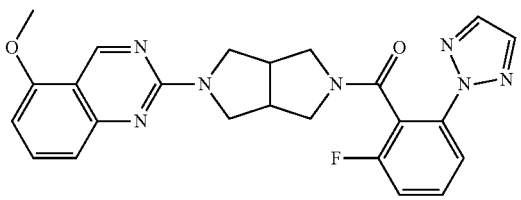 [SMILES: COc1cccc2nc(N3CC4CN(C(=O)c5c(F)cccc5-n5nccn5)CC4C3)ncc12]

MS (ESI, pos. ion) m/z: 460.3 [M+H]+.

Example 45

(2-fluoro-6-(2H-1,2,3-triazol-2-yl)phenyl)(5-(6-methoxyquinolin-2-yl) hexahydropyrrolo[3,4-c]pyrrol-2(1H)-yl)methanone

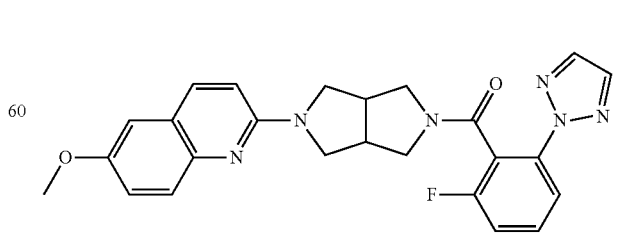

MS (ESI, pos. ion) m/z: 459.3 [M+H]+.

Example 46

(2-fluoro-6-(2H-1,2,3-triazol-2-yl)phenyl)(5-(5-fluorobenzo[d]thiazol-2-yl) hexahydropyrrolo[3,4-c]pyrrol-2(1H)-yl)methanone

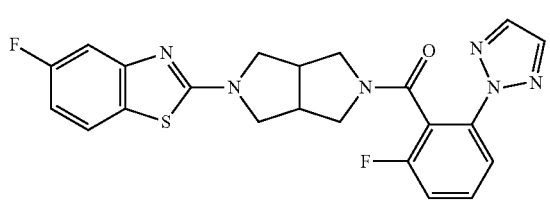 [SMILES: O=C(c1c(F)cccc1-n1nccn1)N1CC2CN(c3nc4cc(F)ccc4s3)CC2C1]

Step 1) Synthesis of 5-fluorobenzo[d]thiazole-2-thiol 2,5-Difluoroaniline (1.00 g, 7.75 mmol) and potassium ethylxanthate (2.73 g, 17.05 mmol) were added into N,N-dimethylformamide (50 mL) in turn, the mixture was heated at 120° C. for 10 h. After the reaction is complete, the mixture was cooled to rt and diluted with water (100 mL). The resulting mixture was adjusted with hydrochloric acid (1 M) to pH 4 to 5. Some solid precipitated, the mixture was filtered by suction. The solid was dried at 50° C. under a vacuum to give the title compound as a white solid (1.11 g, 76.5%).

MS (ESI, pos. ion) m/z: 185.00 [M+H]$^+$; and $^1$H NMR (DMSO-d$_6$, 600 MHz) δ (ppm): 13.98 (s, 1H), 7.55 (d, J=8.2 Hz, 1H), 7.36--7.31 (m, 2H).

Step 2) Synthesis of 2-chloro-5-fluorobenzo[d]thiazole

To a 50 mL of reaction flask were added 5-fluorobenzo[d]thiazole-2-thiol (1.00 g, 5.40 mmol), thionyl chloride (5 mL) and N,N-dimethylformamide (0.10 mL). The mixture was refluxed for 3 h and cooled to rt. The mixture was concentrated in vacuo to give a product, which was used directly in the next step.

Step 3) Synthesis of (2-fluoro-6-(2H-1,2,3-triazol-2-yl)phenyl)(5 (5-fluorobenzo[d]thiazol-2-yl) hexahydropyrrolo[3,4-c]pyrrol-2(1H)-yl)methanone 2-Chloro-5-fluorobenzo[d]thiazole (0.56 g, 2.99 mmol) was reacted with (2-fluoro-6-(2H-1,2,3-triazol-2-yl)phenyl)(hexahydropyrrolo[3,4-c]pyrrol-2(1H)-yl)methanone (0.60 g, 1.99 mmol) and potassium carbonate (1.242 g, 9.0 mmol) in acetonitrile (30 mL) according to the procedure as described in step 7 of example 1, and the crude product was purified by silica gel chromatography (PE/EtOAc (v/v)=1/2) to give the title compound as a yellow solid (0.55 g, 63.5%).

MS (ESI, pos. ion) m/z: 453.15 [M+H]$^+$; and $^1$H NMR (CDCl$_3$, 600 MHz) δ (ppm): 7.86-7.72 (m, 3H), 7.55-7.49 (m, 1H), 7.31-7.29 (m, 1H), 7.18-7.15 (m, 2H), 7.01-6.98 (m, 1H), 4.02-3.85 (m, 2H), 3.84-3.76 (m, 2H), 3.72-3.69 (m, 1H), 3.63-3.59 (m, 2H), 3.21-3.18 (m, 1H), 3.15-3.03 (m, 2H).

Example 47

(5-(5-fluoro-1H-benzo[d]imidazol-2-yl)hexahydropyrrolo[3,4-c]pyrrol-2(1H)-yl) (2-fluoro-6-(2H-1,2,3-triazol-2-yl)phenyl)methanone

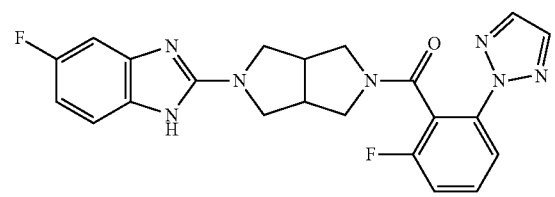 [SMILES: O=C(c1c(F)cccc1-n1nccn1)N1CC2CN(c3nc4cc(F)ccc4[nH]3)CC2C1]

Step 1) Synthesis of 5-fluoro-1H-benzo[d]imidazole-2-thiol

4-Fluorobenzene-1,2-diamine (1.26 g, 10.0 mmol), 1,1'-carbonyldiimidazole (1.78 g, 10.99 mmol) and tetrahydrofuran (30 mL) were added into a 100 mL of reaction flask. The mixture was stirred at rt overnight. After the reaction is complete, concentrated ammonia water (2 mL) was added to the mixture, and the mixture was stirred for 30 min and diluted with water (100 mL). Some solid precipitated, the mixture was filtered by suction. The solid was dried at 50° C. under a vacuum to give the title compound as a pale yellow solid (1.00 g, 65.8%).

MS (ESI, pos. ion) m/z: 169.05 [M+H]$^+$; and $^1$H NMR (DMSO-d$_6$, 600 MHz) δ (ppm): 13.99 (s, 1H), 7.52 (d, J=8.2 Hz, 1H), 7.39-7.33 (m, 2H), 5.10 (s, 1H).

Step 2) Synthesis of 2-chloro-5-fluoro-1H-benzo[d]imidazole

To a 50 mL of reaction flask were added 5-fluoro-1H-benzo[d]imidazole-2-thiol (1.00 g, 6.57 mmol) and phosphorus oxychloride (25 mL). The mixture was refluxed for 13 h. After the reaction is complete, the mixture was concentrated to remove excess phosphorus oxychloride. The resulting mixture was quenched with saturated sodium bicarbonate solution (15 mL), and extracted with ethyl acetate (10 mL×3). The combined organic layers were dried over anhydrous sodium sulfate and concentrated in vacuo to give the title compound as a pale yellow solid (1.03 g, 92.0%).

MS (ESI, pos. ion) m/z: 171.05 [M+H]$^+$.

Step 3) (5-(5-fluoro-1H-benzo[d]imidazol-2-yl) hexahydropyrrolo[3,4-c]pyrrol-2(1H)-yl)(2-fluoro-6-(2H-1,2,3-triazol-2-yl)phenyl)methanone 2-Chloro-5-fluoro-1H-benzo[d]imidazole (0.51 g, 2.99 mmol) was reacted with (2-fluoro-6-(2H-1,2,3-triazol-2-yl)phenyl)(hexahydropyrrolo[3,4-c]pyrrol-2(1H)-yl)methanone (0.60 g, 1.99 mmol) and potassium carbonate (1.242 g, 9.0 mmol) in acetonitrile (30 mL) according to the procedure as described in step 7 of example 1, and the crude product was purified by silica gel chromatography (PE/EtOAc (v/v)=1/2) to give the title compound as a yellow solid (0.58 g, 66.8%).

MS (ESI, pos. ion) m/z: 436.15 [M+H]$^+$; and $^1$H NMR (CDCl$_3$, 600 MHz) δ (ppm): 7.83-7.75 (m, 3H), 7.52-7.49 (m, 1H), 7.31-7.27 (m, 1H), 7.19-7.14 (m, 2H), 7.05-6.99 (m, 1H), 4.03-3.87 (m, 2H), 3.88-3.78 (m, 2H), 3.73-3.68 (m, 1H), 3.66-3.59 (m, 2H), 3.23-3.17 (m, 1H), 3.11-2.99 (m, 2H).

Example 48

(2-fluoro-6-(2H-1,2,3-triazol-2-yl)phenyl)(5-(8-fluoroquinolin-2-yl) hexahydropyrrolo[3,4-c]pyrrol-2 (1H)-yl)methanone

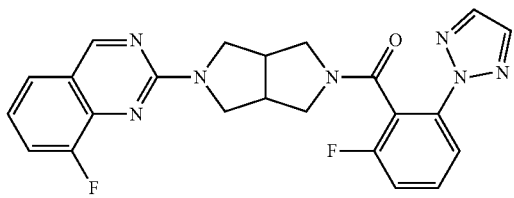 [SMILES: O=C(c1c(F)cccc1-n1nccn1)N1CC2CN(c3ncc4cccc(F)c4n3)CC2C1]

2-Chloro-8-fluoroquinoline (0.54 g, 2.99 mmol), (2-fluoro-6-(2H-1,2,3-triazol-2-yl) phenyl)(hexahydropyrrolo[3,4-c]pyrrol-2(1H)-yl)methanone (0.60 g, 1.99 mmol) and potassium carbonate (1.39 g, 9.98 mmol) were added into 40 mL of acetonitrile in turn. The mixture was refluxed under $N_2$ for 10 h and cooled to rt. The mixture was concentrated in vacuo, the obtained thick oil was dissolved in dichloromethane (30 mL). The resulting mixture was washed with water (30 mL) and saturated brines (30 mL) successively. The organic layer was dried over anhydrous sodium sulfate and concentrated in vacuo. The residue was purified by silica gel chromatography (PE/EtOAc (v/v)=1/2) to give the title compound as a yellow solid (0.52 g, 58.5%).

MS (ESI, pos. ion) m/z: 447.25 $[M+H]^+$; and $^1$H NMR (CDCl$_3$, 600 MHz) δ (ppm): 8.98 (d, J=1.8 Hz, 1H), 7.85 (s, 2H), 7.69-7.63 (m, 2H), 7.59 (d, J=4.3 Hz, 1H), 7.53-7.39 (m, 2H), 7.25 (dd, J=7.6 Hz, 2.5 Hz, 1H), 7.15 (dd, J=17.8 Hz, 8.8 Hz, 1H), 4.03-3.95 (m 2H), 3.89-3.81 (m, 2H), 3.78-3.68 (m, 2H), 3.63-3.57 (m, 1H), 3.35-3.29 (m, 1H), 3.21-3.03 (m, 2H)

Biological Assay

Example A

Test of Antagonistic Effect of Compounds Disclosed Herein on Humanized OX$_1$ Receptor Test Method The capability of the compounds provided herein to antagonize humanized OX$_1$ receptor expressed in Chinese hamster ovary (CHO) cells was evaluated by the influence of the compounds disclosed herein on calcium flux in cells induced by agonist detected by a method of fluorescence detection. The cells were suspended in DMEM culture medium (invitrogen), and then added to a microplate with an average density of $2\times10^4$ cells/well. The Hank's balanced salt solution (pH 7.4) containing fluorescent probes (Fluo4 NW, Invitrogen), probenecid (invitrogen), 20 mM hydroxyethyl piperazine acetic sulfuric acid (invitrogen) was added to the above microplate, and then incubated together with the cells at 37° C. for 60 min, further incubated at 22° C. for 15 min. The microplate was placed in a microplate reader (CellLux, PerkinElmer), and to which was added the test compound or reference antagonist or Hank's balanced salt solution, 5 min later, 3 nM of orexin A or Hank's balanced salt solution (as a blank contrast) was added. The changes of fluorescence intensity were measured, which showed a positive correlation with the changes of the concentration of intracellular free calcium ions. The experimental results were expressed as an inhibition percentage relative to a control group (the group with 3 nM of orexin A).

The standard reference antagonist is SB334867, and IC$_{50}$ values were calculated by the dose-effect curve obtained from a series of concentrations of the experimental test.

The positive control is suvorexant.

The experimental results showed that the compounds disclosed herein shows antagonistic effect on OX$_1$ receptor.

Taking a part of compounds provided herein as an example and the antagonistic effects of the compounds on OX$_1$ receptors were obtained. The results were shown in Table 1, which are the experimental results of antagonistic effect of a part of compounds provided herein on OX$_1$ receptor.

TABLE 1

The experimental results of antagonistic effect of compounds disclosed herein on OX$_1$ receptor.

| Test compound | OX$_1$ IC$_{50}$ (nM) |
|---|---|
| Example 1: | 604 |
| Example 4: | 611 |
| Example 5 | 642 |
| Example 6 | 589 |
| Example 12 | 347 |
| suvorexant | 341 |

Example B

Test of Antagonistic Effect of Compounds Disclosed Herein to Humanized OX$_2$ Receptor Test Method The capability of the compounds provided herein to antagonize humanized OX$_2$ receptors expressed in HEK-293 cells was evaluated by the influence of the compounds disclosed herein on calcium flux in cells induced by agonist detected by a method of fluorescence detection. The cells were suspended in DMEM culture medium (invitrogen), and then added to a microplate with an average density of $3\times10^4$ cells/well. The Hank's balanced salt solution (pH 7.4) containing fluorescent probes (Fluo4 NW, Invitrogen), probenecid (invitrogen), 20 mM hydroxyethyl piperazine acetic sulfuric acid (invitrogen) was added to the above microplate, and then incubated together with the cells at 37° C. for 60 min, further incubated at 22° C. for 15 min. The microplate was placed in a microplate reader (CellLux, PerkinElmer), and to which was added the test compound or reference antagonist or Hank's balanced salt solution, 5 min later, 10 nM of orexin B or Hank's balanced salt solution (as a blank contrast) was added. The changes of fluorescence intensity were measured, which showed a positive correlation with the changes of the concentration of intracellular free calcium ions. The experimental results were expressed as an inhibition percentage relative to a control group (the group with 10 nM of orexin B).

The standard reference antagonist is JNJ10397049, and IC$_{50}$ values were calculated by the dose-effect curve obtained from a series of concentrations of the experimental test.

The positive control is suvorexant.

The experimental results showed that the compounds disclosed herein shows better antagonistic effect on OX$_2$ receptor than suvorexant.

Taking a part of compounds provided herein as an example and the antagonistic effects of the compounds on $OX_2$ receptors were obtained.

The results were shown in Table 2, which are the experimental results of antagonistic effect of a part of compounds provided herein on $OX_2$ receptor.

TABLE 2

The experimental results of antagonistic effect of compounds disclosed herein on $OX_2$ receptor.

| Test compound | $OX_2$ $IC_{50}$ (nM) |
| --- | --- |
| Example 1: | 308 |
| Example 2: | 221 |
| Example 3: | 147 |
| Example 4 | 342 |
| Example 5 | 235 |
| Example 6 | 201 |
| Example 12 | 140 |
| suvorexant | 327 |

Example C

Pharmacokinetic Evaluation after Administering a Certain Amount of the Compounds of the Invention by Intravenous or Gavage to Rats, Dogs and Monkeys The pharmacokinetic evaluation of the compound disclosed herein in rats, dogs and monkeys was carried out in the invention, and animal information showed as described in table A.

TABLE A

Information of subject animals of the present invention

| genus | classification | gender | weight | age | source |
| --- | --- | --- | --- | --- | --- |
| SD rats | SPF | Male | 170-250 g | 6-9 weeks old | Hunan SJA Laboratory Animal Co., Ltd |
| Beagle dogs | clean grade | Male | 8~10 kg | 6-7 weeks old | Hunan SJA Laboratory Animal Co., Ltd |
| Cynomolgus monkeys | SPF | Male | 3~5 kg | 4 years old | Guangdong Landau Biotechnology Co., Ltd |

Test Method

The compounds disclosed herein were administered in form of a saline solution containing 5% DMSO, 5% Kolliphor HS 15, 2% (2% HCl) and 88% Saline, or a solution containing 10% DMSO, 10% Kolliphor HS 15 and 80% physiological saline to the subject animals. For intravenous administration, the animals were administered with a dose of 1 mg/kg or 2 mg/kg, and vein blood samples (0.3 mL) were collected at the time points of 0.083, 0.25, 0.5, 1.0, 2.0, 4.0, 6.0, 8.0 and 24 h after drug administration; plasma samples were collected by centrifugation of the vein blood samples at 3000 rpm or 4000 rpm for 10 minutes, and stored at −20° C. or −70° C. For gavage administration, the animals were administered with a dose of 2.5 mg/kg or 5 mg/kg, and vein blood samples (0.3 mL) were collected at the time points of 0.25, 0.5, 1.0, 2.0, 4.0, 6.0, 8.0 and 24 h after drug administration; plasma samples were collected by centrifugation at 3000 rpm or 4000 rpm for 10 minutes, and stored at −20° C. or −70° C. The positive control is suvorexant.

The above plasma samples were analyzed by the LC-MS/MS system. The analytic results showed that the compounds of the invention have good pharmacokinetic properties and oral bioavailability in rats, dogs and monkeys, wherein the pharmacokinetic parameters of compounds provided in Example 1, 2, 3, 12 and 13 in rats are shown in Table 3, the pharmacokinetic parameters of compounds provided in Example 1, 3 and 12 in dogs are shown in Table 4.

TABLE 3

Pharmacokinetic parameters of compounds disclosed herein in rats.

| Group | Test compound | Dose (mg/kg) | $C_{max}$ (ng/mL) | $AUC_{last}$ (h*ng/mL) | $AUC_{INF}$ (h*ng/mL) | $MRT_{INF}$ (h) | $T_{1/2}$ (h) | Cl (mL/min/kg) | $V_{ss}$ (L/kg) | F (%) |
| --- | --- | --- | --- | --- | --- | --- | --- | --- | --- | --- |
| iv | Example 1 | 1 | 646 | 415 | 417 | 0.638 | 0.676 | 40 | 1.53 | ND |
|  | Example 2 | 1 | 639 | 549 | 551 | 0.787 | 0.602 | 30.4 | 1.42 | ND |
|  | Example 3 | 1 | 760 | 624 | 626 | 0.759 | 0.577 | 26.7 | 1.21 | ND |
|  | Example 12 | 1 | 749 | 460 | 460 | 0.427 | 0.405 | 40.1 | 0.987 | ND |
|  | Example 13 | 1 | 1270 | 864 | 865 | 0.549 | 0.501 | 20.1 | 0.648 | ND |
|  | suvorexant | 2 | 784 | 655 | 655 | 0.708 | 0.569 | 51.2 | 2.17 | ND |
| po | Example 1 | 2.5 | 181 | 482 | 659 | 3.03 | 2.21 | ND | ND | 50.1 |
|  | Example 2 | 2.5 | 485 | 783 | 790 | 1.48 | 1.03 | ND | ND | 57.3 |
|  | Example 3 | 2.5 | 567 | 904 | 907 | 1.37 | 0.874 | ND | ND | 57.9 |
|  | Example 12 | 2.5 | 340 | 452 | 454 | 1.28 | 0.837 | ND | ND | 39.3 |
|  | Example 13 | 2.5 | 537 | 750 | 752 | 1.17 | 0.683 | ND | ND | 34.7 |
|  | suvorexant | 5 | 249 | 528 | 530 | 1.95 | 0.99 | ND | ND | 32.4 |

ND: means no detection data

As can be seen from the results of Table 3, the compounds disclosed herein has better pharmacokinetic properties in rats than suvorexant.

TABLE 4

Pharmacokinetic parameters of compounds disclosed herein in dogs

| Group | Test compound | Dose (mg/kg) | $C_{max}$ (ng/mL) | $AUC_{last}$ (h*ng/mL) | $AUC_{INF}$ (h*ng/mL) | $MRT_{INF}$ (h) | $T_{1/2}$ (h) | Cl (mL/min/kg) | $V_{ss}$ (L/kg) | F (%) |
|---|---|---|---|---|---|---|---|---|---|---|
| iv | Example 1 | 1 | 821 | 2150 | 2710 | 4.97 | 3.73 | 6.14 | 1.83 | ND |
|    | Example 3 | 1 | 3830 | 8320 | 8330 | 2.91 | 2.40 | 10.00 | 1.75 | ND |
|    | Example 12 | 1 | 1390 | 1130 | 1140 | 0.97 | 0.70 | 14.70 | 0.85 | ND |
|    | suvorexant | 1 | 2100 | 5750 | 5960 | 5.39 | 5.79 | 2.82 | 0.919 | ND |
| po | Example 1 | 5 | 1410 | 15900 | 16300 | 6.84 | 4.41 | ND | ND | 147.6 |
|    | Example 3 | 5 | 5640 | 35000 | 351000 | 4.59 | 2.93 | ND | ND | 84.0 |
|    | Example 12 | 5 | 2310 | 7310 | 7880 | 3.11 | 1.99 | ND | ND | 129.4 |
|    | suvorexant | 5 | 1640 | 13600 | 14300 | 7.2 | 5.71 | ND | ND | 48 |

ND: means no detection data

As can be seen from the results of Table 4, the compounds disclosed herein has better oral bioavailability in dogs than suvorexant.

Example D

Evaluation of the Potential of the Compound Disclosed Herein Inducing Prolongation of QT Interval Test Method The potential of the compound disclosed herein inducing QT interval prolongation was evaluated by detecting if the compound would block the hERG channel. The specific test method is as follows:

Precisely weighed compound disclosed herein was dissolved in DMSO to formulate a solution at the highest concentration of 10.0 mM, and then the solution was diluted to a initial concentration of 120.0 µM with hERG FP Assay Buffer (Invitrogen); the hERG Tracer Red stock solution (Invitrogen) and the positive control E-4031 stock solution (Invitrogen) were respectively diluted to initial concentrations of 4.0 nM and 120.0 µM with hERG FP Assay Buffer (Invitrogen). 2.5 µL of the compound disclosed herein at a initial concentration or the positive control E-4031 at a initial concentration (positive control group) or hERG FP Assay Buffer (negative control group), 5 µL of hERG Membrane and 2.5 µL of hERG Tracer Red were added into a 384-well plate, and 5 µL of hERG FP Assay Buffer and 5 µL of hERG Membrane were added as a blank control group, and the test final concentration of the compound disclosed herein, E-4031 and hERG Tracer Red were respectively 30.0 µM, 30.0 µM and 1.0 nM. Four duplicated wells per group were established. After that, the 384-well plate was put in to an oscillator (PHMP-4, Grant-sio), in 25° C., 250 rpm, to incubate for 4 hours, and the fluorescence polarization values were measured by multi-function microplate reader (PHERAStarFS, BMG LABTECH), and the relative inhibition rate and 50% inhibition concentration ($IC_{50}$) of the compound disclosed herein to hERG channel were calculated.

In the case of E-4031 as a positive control, if the relative inhibition rate of 30.0 µM of the compound disclosed herein to hERG was less than 50%, the $IC_{50}$ of the compound disclosed herein to hERG channel was more than 30.0 µM. If the relative inhibition rate of 30.0 µM of the compound disclosed herein to hERG was more than 50%, the dose titration curve of the compound of this invention is necessary, and the specific method is as follows:

The above-mentioned solution of the compound disclosed herein and E-4031 at the initial concentration of 120 µM were respectively diluted with hERG FP Assay Buffer 5-fold in series to provide 8 concentration of 120.0 µM, 24.0 µM, 4.8 µM, 960.0 nM, 192.0 nM, 38.4 nM, 7.7 nM and 1.5 nM. Two duplicated wells per concentration were established. 2.5 µL of the compound disclosed herein or the positive control E-4031 (positive control group) or hERG FP Assay Buffer (negative control group) at the indicated concentrations, 5 µL of hERG FP Membrane and 2.5 µL of hERG Tracer Red were added into a 384-well plate, and 5 µL of hERG FP Assay Buffer and 5 µL of hERG Membrane were added as a blank control group. After that, the 384-well plate was put into an oscillator (PHMP-4, Grant-sio), in 25° C., 250 rpm, to incubate for 4 hours, and the fluorescence polarization values were measured by multi-function microplate reader (PHERAStarFS, BMG LABTECH) and corrected with the minimum and maximum fluorescence polarization values of E-4031, and the $IC_{50}$ of the compound disclosed herein was calculated by GraphPad software.

The positive control is suvorexant.

The experimental results show that the compound of Example 1 of the invention and the positive control, i.e. suvorexant, have 50% inhibition concentration of 3.28 µM and 1.79 µM respectively against to hERG, it can be seen that the compound of Example 1 of this invention has a weaker inhibitory activity to hERG channel compared to suvorexant, which prompts a lesser risk to cause QT interval elongation compared to suvorexant.

Example E

Evaluation of the Stability of the Compounds Disclosed Herein in Human Liver Microsome A mixture of the compound of the invention and human liver microsome in 0.1 M potassium phosphate buffer (containing 1.0 mM EDTA, pH=4) was incubated at 37° C., the sample concentrations at different incubation times were measured, and then the half life of the compound was calculated by plotting "the relative amount of the compound" against "incubation time" by using software Graph-Pad Prism 5.01, and intrinsic clearance was calculated. The experiment system shown as table 5:

TABLE 5

| experiment system | |
|---|---|
| Test subject | The compound of the invention (dissolved in DMSO and diluted with acetonitrile) |
| Human liver microsome | Pooled Human Liver Microsomes, the test final concentration is 0.5 mg/mL |
| Buffer | 0.1M potassium phosphate buffer (containing 1.0 mM EDTA, pH = 4) |
| Test final concentration of test subject | 1 µM |

TABLE 5-continued

| experiment system | |
| --- | --- |
| Final content of organic solvent | 0.2% |
| Final reaction system | 30 μL of buffer solution containing human liver microsome and compound; 15 μL of NADPH buffer solution (the concentration is 6 mM) |
| Test conditions | Time point: 0 min, 15 min, 30 min, 60 min; Temperature: 37° C.; pH: 7.4 |
| Duplicate sample number | 2 |
| Analytical method | LC/MS/MS, the internal standard is propranolol |

The sample was analyzed by LC/MS/MS (ESI radioactive source and waters xbridge C18 EB-A-1420 chromatographic column were adopted), the mobile phases were an aqueous solution with 2 mM ammonium formate and 0.1% formic acid (mobile phase A) and an methanol solution with 2 mM ammonium formate and 0.1% formic acid (mobile phase B), the flow rate was 0.4 mL/min; the column temperature was 40° C. The ratio of the sample peak area to the internal standard peak area was obtained through LC/MS/MS analysis, the content of the compound at 0 time point was as 100%, the relative content of the compound at each time point was calculated. The half life of the compound was calculated by plotting "the relative amount of the compound" against "incubation time", and intrinsic clearance was calculated.

The positive control is suvorexant.

The experimental results show that the compounds of this invention have higher stability in human liver microsome than suvorexant.

Taking the compound of example 1 as an example and the half life and intrinsic clearance of the compound in human liver microsome were obtained.

The results were shown in Table 6.

TABLE 6

| the stability in human liver microsome of the compound of example 1 | | |
| --- | --- | --- |
| sample | Half life (min) | intrinsic clearance (mL/min/kg) |
| Example1 | 49.52 | 35.10 |
| suvorexant | 9.85 | 176.46 |

As can be seen from the results of Table 6, the compound of example 1 has higher stability in human liver microsome than suvorexant.

Reference throughout this specification to "an embodiment", "some embodiments", "one embodiment", "another example", "an example", "a specific examples" or "some examples" means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific example" or "in some examples" in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. The compound having Formula (III), or a stereoisomer, a tautomer, an N-oxide, a solvate, a pharmaceutically acceptable salt or a prodrug thereof,

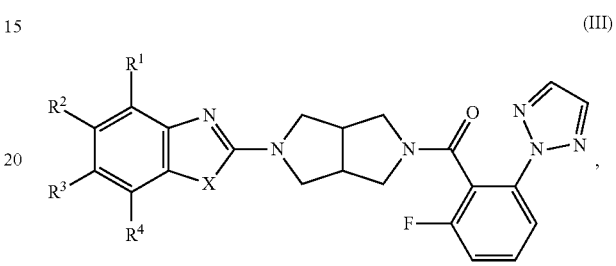

(III)

wherein X is —O—, —S—, —NH—, or *—CR$^9$=CR$^{9a}$—, wherein * refers to an end attached to the benzene ring; and each R$^1$, R$^2$, R$^3$, R$^4$, R$^9$ and R$^{9a}$ is independently H, D, —CD$_3$, —CN, —NH$_2$, —OH, —NO$_2$, —COOH, —C(=O)NH$_2$, halogen, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, C$_{1-6}$ alkylamino, C$_{1-6}$ hydroxy-substituted alkyl, (C$_{1-6}$ alkyl)—C(=O)—, (C$_{1-6}$ alkoxy)—C(=O)—, (C$_{1-6}$ alkylamino)—C(=O)—, cycloalkyl, heterocyclyl, aryl or heteroaryl.

2. The compound of claim 1, wherein each R$^1$, R$^2$, R$^3$, R$^4$, R$^9$ and R$^{9a}$ is independently H, D, —CD$_3$, —CN, —NH$_2$, —OH, —NO$_2$, —COOH, —C(=O)NH$_2$, halogen, C$_{1-4}$ alkyl, C$_{2-4}$ alkenyl, C$_{2-4}$ alkynyl, C$_{1-4}$ haloalkyl, C$_{1-4}$ alkoxy, C$_{1-4}$ haloalkoxy, C$_{1-4}$ alkylamino, C$_{1-4}$ hydroxy-substituted alkyl, (C$_{1-4}$ alkyl)—C(=O)—, (C$_{1-4}$ alkoxy)—C(=O)— or (C$_{1-4}$ alkylamino)—C(=O)—.

3. The compound of claim 1, wherein each R$^1$, R$^2$, R$^3$, R$^4$, R$^9$ and R$^{9a}$ is independently H, D, —CD$_3$, —CN, —NH$_2$, —OH, —NO$_2$, —COOH, —C(=O)NH$_2$, F, Cl, Br, I, methyl, ethyl, n-propyl, isopropyl, —CF$_3$, —CH$_2$CF$_3$, —CF$_2$CF$_3$, methoxy, ethoxy, n-propyloxy, isopropyloxy, —NHCH$_3$, —N(CH$_3$)$_2$ or —CH$_2$OH.

4. A compound having one of the following structures or a stereoisomer, a tautomer, an N-oxide, a solvate, a pharmaceutically acceptable salt or a prodrug thereof,

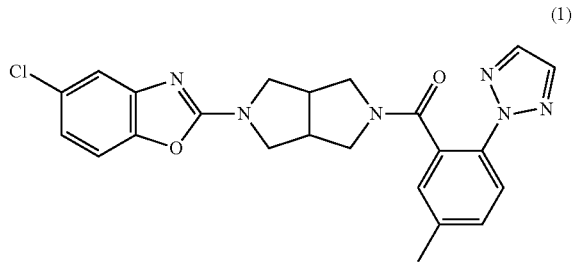

(1)

-continued
(2)
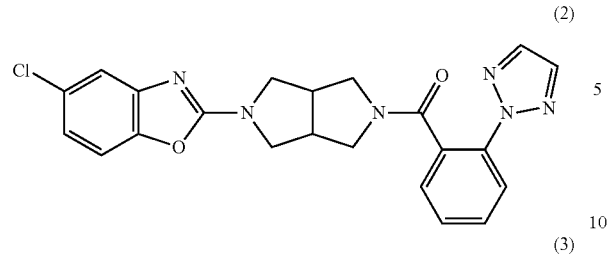
(3)
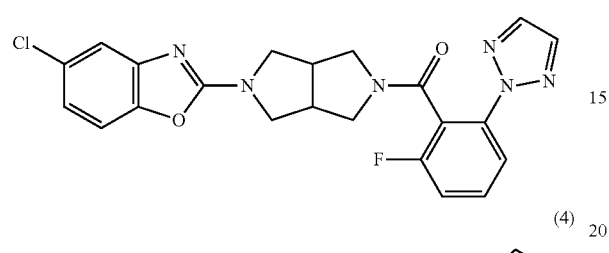
(4)
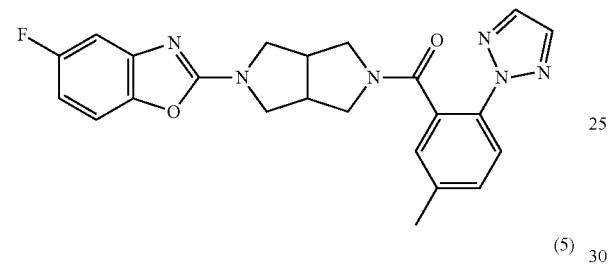
(5)
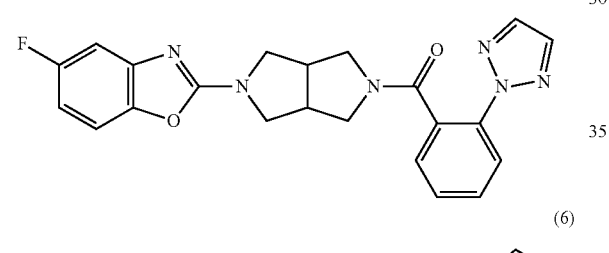
(6)
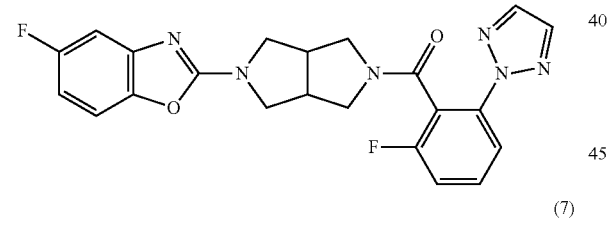
(7)
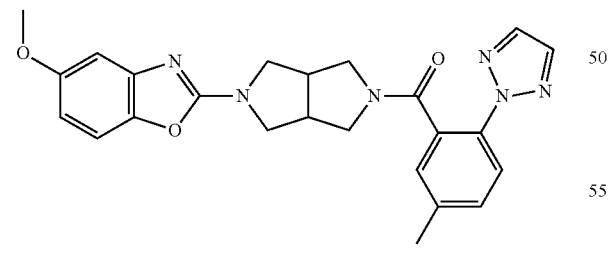
(8)
-continued
(9)
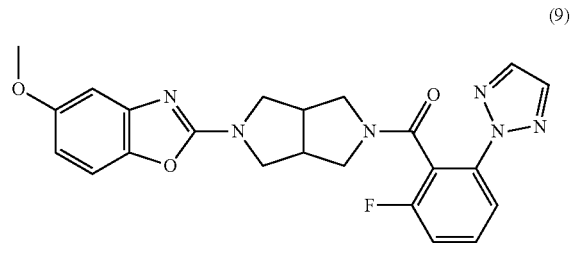
(10)
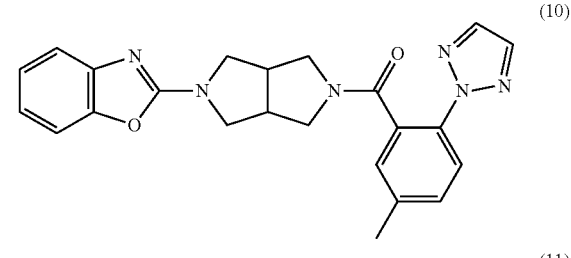
(11)
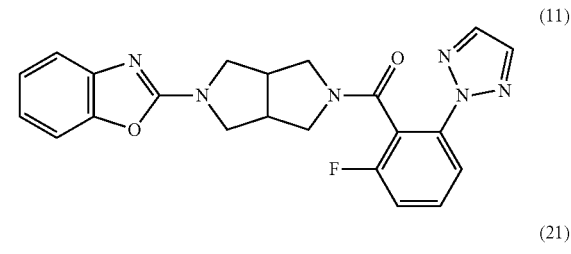
(21)
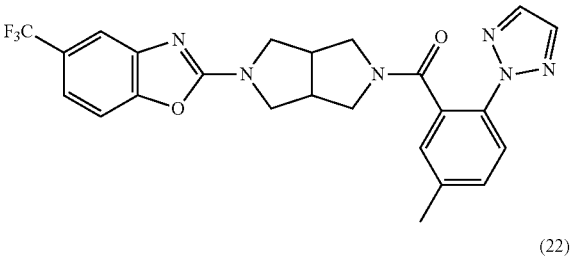
(22)
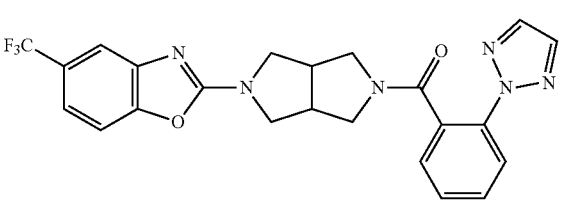
(23)
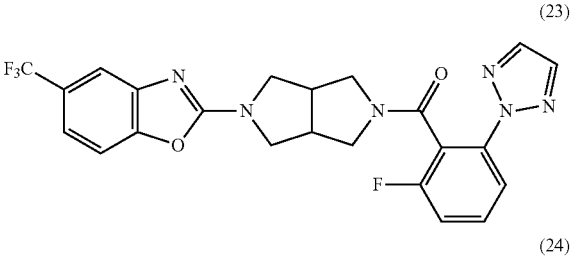
(24)
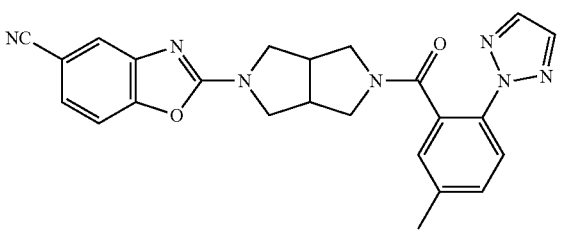

(25)
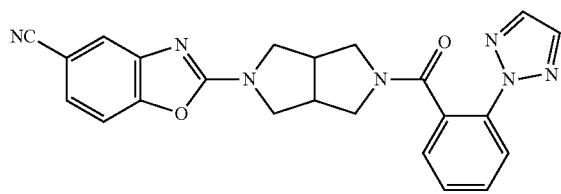
(26)
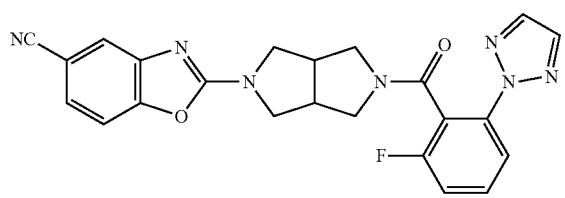
(27)
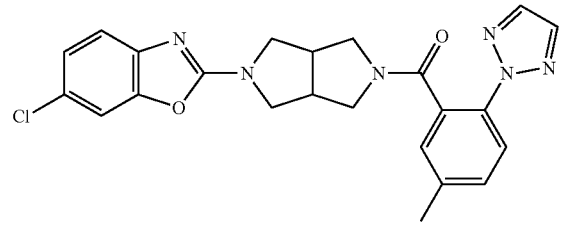
(28)
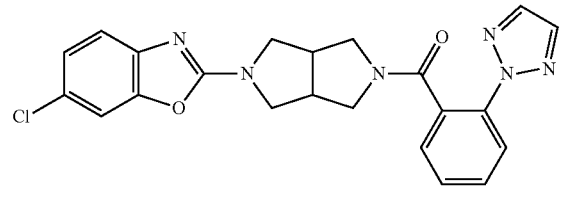
(29)
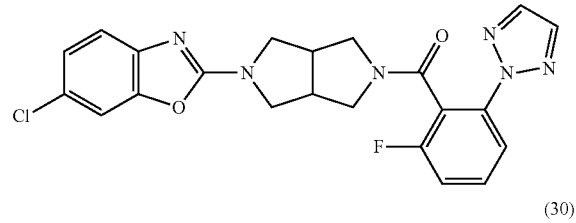
(30)
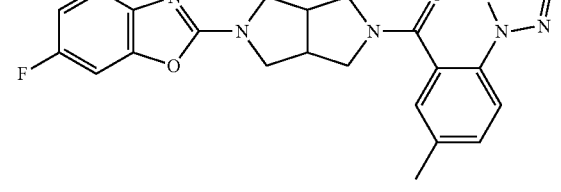
(31)
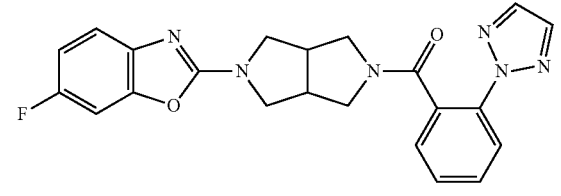
(32)
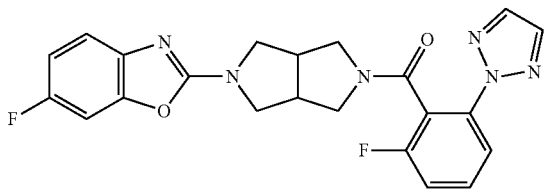
(33)
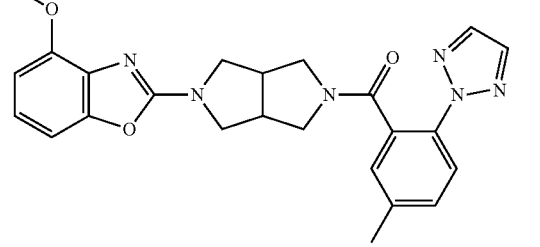
(34)
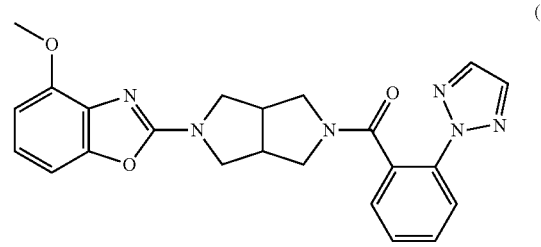
(35)
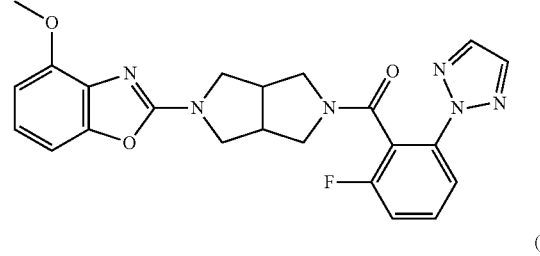
(45)
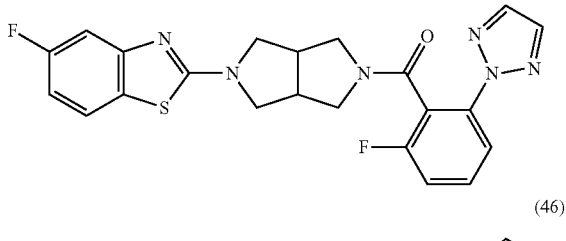
(46)
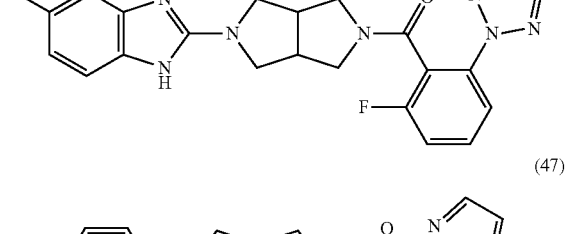
(47)
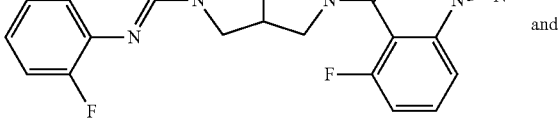
and -continued (48)

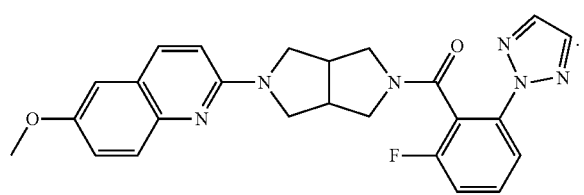

5. A pharmaceutical composition comprising the compound of claim 1 and optionally, wherein the pharmaceutical composition further comprising a pharmaceutically acceptable carrier, excipient, adjuvant or a combination thereof.

6. A pharmaceutical combination for use in treating or lessening a disease related to one or more orexin receptors, wherein the pharmaceutical combination comprising the compound of claim 1 as a first active agent; and a medicament different from the compound of claim 1 as the second active agent, wherein the medicament different from the compound of claim 1 is for use in preventing, treating or lessening a disease related to one or more orexin receptors.

7. A kit for use in treating or lessening a disease related to one or more orexin receptors, wherein the kit comprises:
a first container, wherein the first container is provided with the compound of claim 1 and
optionally, a second container, wherein the second container is provided with a medicament different from the compound of claim 1, wherein the medicament different from the compound of claim 1 is for use in preventing, treating or lessening a disease related to one or more orexin receptors.

* * * * *